(12) United States Patent
Case et al.

(10) Patent No.: US 10,169,865 B2
(45) Date of Patent: Jan. 1, 2019

(54) MULTI ENERGY X-RAY MICROSCOPE DATA ACQUISITION AND IMAGE RECONSTRUCTION SYSTEM AND METHOD

(71) Applicant: Carl Zeiss X-ray Microscopy, Inc., Pleasanton, CA (US)

(72) Inventors: Thomas A. Case, Walnut Creek, CA (US); Susan Candell, Lafayette, CA (US); Srivatsan Seshadri, San Ramon, CA (US); Naomi Kotwal, Fremont, CA (US)

(73) Assignee: Carl Zeiss X-Ray Microscopy, Inc., Pleasanton, CA (US)

( * ) Notice: Subject to any disclaimer, the term of this patent is extended or adjusted under 35 U.S.C. 154(b) by 54 days.

(21) Appl. No.: 15/295,071

(22) Filed: Oct. 17, 2016

(65) Prior Publication Data

US 2017/0109882 A1    Apr. 20, 2017

Related U.S. Application Data

(60) Provisional application No. 62/243,102, filed on Oct. 18, 2015.

(51) Int. Cl.
*G06T 7/00* (2017.01)
*A61B 6/03* (2006.01)
(Continued)

(52) U.S. Cl.
CPC ............. *G06T 7/0012* (2013.01); *A61B 6/03* (2013.01); *G01N 23/046* (2013.01);
(Continued)

(58) Field of Classification Search
CPC .... A61B 6/03; G01N 23/046; G06F 3/04842; G06K 9/6212; G06T 11/003; G06T 15/08;
(Continued)

(56) References Cited

U.S. PATENT DOCUMENTS 6,418,189 B1    7/2002  Schafer
9,128,584 B2    9/2015  Case et al.
(Continued)

FOREIGN PATENT DOCUMENTS

DE    100 63 290 A1    9/2001
EP      0 614 153 A2    9/1994
(Continued)

OTHER PUBLICATIONS

Cesareo, R. et al. "Material analysis with a multiple X-ray tomography scanner using transmitted and scattered radiation," Nuclear Instruments and Methods in Physics Research, Section A, 525 (2004): pp. 336-341. Six pages.
(Continued)

*Primary Examiner* — Siamak Harandi
(74) *Attorney, Agent, or Firm* — HoustonHogle LLP

(57) ABSTRACT

An x-ray imaging system data acquisition and image reconstruction system and method are disclosed which enable optimizing the image parameters based on multiple tomographic volumes of the sample that have been captured using an x-ray microscopy system. This enables the operator to control the image contrast, for example, of selected slices, and apply the information associated with optimizing the contrast of the selected slice to all slices in two or more tomographic volume data sets. This creates a combined volume with optimized image contrast throughout. Also, the system enables navigation within the volumes through functional annotation, improvements in volume registration and improvements in noise suppression both within the volumes and within slice histograms of the sample.

3 Claims, 42 Drawing Sheets

(51) Int. Cl.

| | |
|---|---|
| G01N 23/046 | (2018.01) |
| G06K 9/62 | (2006.01) |
| G21K 7/00 | (2006.01) |
| G06T 15/08 | (2011.01) |
| G06F 3/0484 | (2013.01) |
| G06T 5/00 | (2006.01) |
| G06T 11/00 | (2006.01) |
| G06T 7/33 | (2017.01) |

(52) U.S. Cl.
CPC ....... *G06F 3/04842* (2013.01); *G06K 9/6212* (2013.01); *G06T 5/002* (2013.01); *G06T 7/33* (2017.01); *G06T 11/003* (2013.01); *G06T 15/08* (2013.01); *G21K 7/00* (2013.01); *G06T 2207/10056* (2013.01); *G06T 2207/10081* (2013.01); *G06T 2207/10141* (2013.01); *G06T 2207/20104* (2013.01); *G06T 2207/20108* (2013.01); *G06T 2207/20221* (2013.01); *G06T 2210/41* (2013.01)

(58) Field of Classification Search
CPC . G06T 2207/10056; G06T 2207/10081; G06T 2207/10141; G06T 2207/20104; G06T 2207/20108; G06T 2207/20221; G06T 2210/41; G06T 5/002; G06T 7/0012; G06T 7/33; G21K 7/00
See application file for complete search history.

(56) References Cited

U.S. PATENT DOCUMENTS

| | | |
|---|---|---|
| 2004/0076260 A1 | 4/2004 | Charles, Jr. et al. |
| 2004/0264626 A1 | 12/2004 | Besson |
| 2007/0280417 A1 | 12/2007 | Kang et al. |
| 2008/0100612 A1 | 5/2008 | Dastmalchi et al. |
| 2008/0260092 A1 | 10/2008 | Imai et al. |
| 2009/0028287 A1 | 1/2009 | Krauss et al. |
| 2010/0246754 A1 | 9/2010 | Morton |
| 2012/0087564 A1 | 4/2012 | Tsujita |
| 2013/0301794 A1 | 11/2013 | Grader et al. |
| 2014/0086381 A1 | 3/2014 | Grader et al. |
| 2014/0233692 A1 | 8/2014 | Case et al. |
| 2015/0323474 A1 | 11/2015 | Case et al. |

FOREIGN PATENT DOCUMENTS

| | | |
|---|---|---|
| EP | 2 437 050 A1 | 4/2012 |
| WO | 2015153505 A1 | 10/2015 |
| WO | 2015153506 A1 | 10/2015 |

OTHER PUBLICATIONS

Cesareo, Roberto. "Principles and Applications of Differential Tomography," Nuclear Instruments and Methods in Physics Research, Section A, 270 (1988): pp. 572-577. Six pages.

Depypere, M. et al., An iterative dual energy CT reconstruction method for a K-edge contrast material, SPIE Medical Imaging, International Society for Optics and Photonics, Mar. 2011. Seven pages.

Pelc, Norbert J., Sc.D., "Dual Energy CT: Physics Principles," slide show presentation, Departments of Radiology and Bioengineering, Stanford University, 2008. Eleven pages.

Wang, Jun et al. "Automated markerless full field hard x-ray microscopic tomography at sub-50 nm 3-dimension spatial resolution," Applied Physics Letters 100, 143107 (2012). Four pages.

International Search Report and Written Opinion of the International Searching Authority, dated Oct. 20, 2014, from counterpart International Application No. PCT/US2014/011689, filed on Jan. 15, 2014. Twenty-three pages.

International Preliminary Report on Patentability, dated Aug. 27, 2015 from International Application No. PCT/US2014/011689, filed on Jan. 15, 2014. Fifteen pages.

Extended European Search Report, dated Mar. 21, 2017, from European Application No. 16 194 240.4. Seven pages.

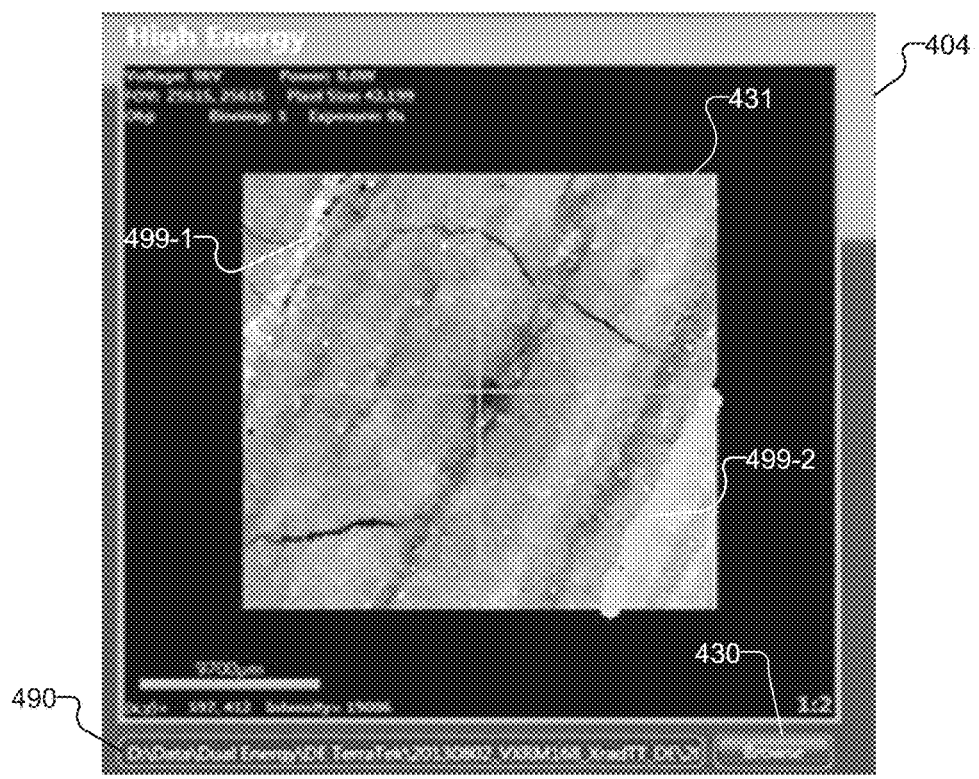
Fig. 20B-1
Fig. 20B-2          Copyright 2015 Carl Zeiss X-ray Microscopy, Inc.

MULTI ENERGY X-RAY MICROSCOPE DATA ACQUISITION AND IMAGE RECONSTRUCTION SYSTEM AND METHOD

RELATED APPLICATIONS

This application claims the benefit under 35 USC 119(e) of U.S. Provisional Application No. 62/243,102, filed on Oct. 18, 2015, which is incorporated herein by reference in its entirety.

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

High resolution x-ray imaging systems, also known as X-ray imaging microscopes ("XRM"), provide high-resolution/high magnification, non-destructive imaging of internal structures in samples for a variety of industrial and research applications, such as materials science, clinical research, and failure analysis to list a few examples. XRMs provide the ability to visualize features in samples without the need to cut and slice the samples.

XRMs are often used to perform computed tomography ("CT") scans of samples. CT scanning is the process of generating three dimensional tomographic volumes of the samples from a series of projections at different angles. XRMs often present these tomographic volumes in two-dimensional, cross-sectional images or "slices" of the three dimensional tomographic volume data set. The tomographic volumes are generated from the projection data using software reconstruction algorithms based on back-projection and other image processing techniques to reveal and analyze features within the samples. U.S. Pat. No. 9,128,584, entitled Multi Energy X-Ray Microscope Data Acquisition and Image Reconstruction System and Method, discloses such an XRM system for optimizing the image contrast of a sample and is incorporated herein by reference in its entirety.

Dual energy contrast tuning tools have been developed for XRMs. One such example is described in U.S. Pat. Appl. Pub. No. US 2014/0233692 A1, which is incorporated herein in its entirety by this reference.

SUMMARY OF THE INVENTION

The present invention concerns a multi energy, such as dual-energy, x-ray imaging data acquisition and image reconstruction system and method for combining separate reconstructed volumes taken under different conditions such as at different energies and allowing the operator to manipulate and optimize the image display parameters. Operators use the system and method to improve image quality and contrast over current XRM data acquisition and image reconstruction systems and methods and facilitate image analysis.

Moreover, the system can be extended to other situations in which the volumes were captured under differing conditions, beyond multi energy imaging. For example, the system and method can be employed to compare volumes and optimize image display parameters for volumes that were captured with absorption contrast tomography against volumes captured with phase contrast tomography, or to compare volumes of a wet sample against the sample when it was dry, or compare volumes of a sample with a contrast agent against volumes that were taken when the sample had no contrast agent. Other examples include volumes captured with different mixes of x-ray energy other than simply high and low energy. Further, the system can compare volumes reconstructed using different reconstruction methods since different reconstruction methods can give rise to different artifacts. Thus, the system can be used to view different parts of the sample using different reconstruction methods or a blend of the methods.

The x-ray imaging system includes an image tuning tool application, or tuning tool. The tuning tool is an image analysis tool that executes on a computer system such as an embedded system, workstation or server that enables operators to interact with the x-ray imaging system to create, display, and analyze images of a sample. Image display parameters are tuned to create different representations of the sample for revealing information about elements of interest within the sample based on volumes captured under different conditions. In one example, image display parameters are optimized in the creation of synthetic two dimensional images and three dimensional volumes of the sample to enable the determination of the spatial distribution of elements of interest within the sample, for example. In another example, image display parameters are controlled by reference to statistical information generated or extracted from the two dimensional images and three dimensional volumes, the contents and/or contrast of which can be enhanced to reveal elements of interest and/or relationships among elements in the sample.

In general, according to one aspect, the invention features an image analysis tool of an x-ray microscopy system that provides the ability to create, display, and analyze images of a sample. The image analysis tool comprising or generating a user interface that comprises a first window for displaying slices from a first reconstructed tomographic volume data set, a second window for displaying slices from a second reconstructed tomographic volume data set, and a noise reduction filter window that enables application of noise reduction filters to the first reconstructed tomographic volume data set and/or the second reconstructed tomographic volume data set.

In general, according to another aspect, the invention features an image analysis tool of an x-ray imaging microscopy system that provides the ability to create, display, and analyze image of a sample. The image analysis tool comprising a user interface that includes windows that display the images of the sample, wherein the user interface additionally includes an animation tool that enables the display of the images within the windows of the user interface in a sequence and possibly for a selected range of slices.

In general, according to still another aspect, the invention features a method for registering a first reconstructed tomographic volume data set of a sample with a second tomographic volume data set of the sample. The method comprises a user interface of a computer system detecting user selection of a range of slices of the first and the second tomographic volume data sets to register with one another and finding fractional offsets of pixels in the first and the second tomographic volume data sets and further aligning the tomographic volume data sets such that the slices within the selected range of slices are now aligned with sub pixel accuracy.

In general, according to still another aspect, the invention features a user interface of an x-ray imaging microscopy system that enables creation of two-dimensional histograms of energy pixel intensity values for a first reconstructed tomographic volume data set and a second reconstructed tomographic volume data set of a sample. These histograms include: a slice histogram rendered from a common slice selected among slices of the first reconstructed tomographic volume data set and of the second reconstructed tomographic volume data set, a sum histogram, where values of points plotted on the sum histogram are the resulting sum of the corresponding points across a user-specified slice selection of the slices, and/or an average histogram, where values of points on the average histogram are the average of the corresponding points across a user-specified slice selection of the slices.

In general, according to still another aspect, the invention features an image analysis tool of an x-ray imaging microscopy system that enables an operator to annotate images displayed within the windows.

In general, according to still another aspect, the invention features a user interface of an x-ray imaging microscopy system that includes windows that display images of a sample. In response to user operations upon pixels within an image displayed in a current window, the user interface renders the pixels subject to the user operations to be visually distinct from pixels not subject to the user operations, and simultaneously renders visually distinct versions of corresponding pixels associated with the user operations within the images displayed in the other windows.

In general, according to still another aspect, the invention features an image analysis tool of an x-ray imaging microscopy system. This image analysis tool displays slices from a first reconstructed tomographic volume data set and displays slices from a second reconstructed tomographic volume data set for the same region of the sample, presents a histogram of pixel intensity values based on the selected slice, enables definition of one or more regions of interest (ROI) within the histogram, and provides the ROI pixels to the computer system for creation of a synthetic slice for the selected slice using the ROI pixels.

In general, according to still another aspect, the invention features an image analysis tool of an x-ray imaging system that enables gradient suppression of pixels in a histogram to eliminate pixel artifacts in the histogram caused by edges of elements.

In general, according to still another aspect, the invention features an image analysis tool of an x-ray imaging system that enables a region integration function upon histograms to plot points where the values of the points in the histogram are the average values for each labeled region.

In general, according to still another aspect, the invention features an image analysis tool executing within a computer system of an x-ray imaging microscopy system. This image analysis tool generates a first set of x-ray projections of a sample under a first set of conditions and a second set of x-ray projections of the sample under a second set of conditions, generates a first reconstructed tomographic volume data set from the first set of x-ray projections and a second reconstructed tomographic volume data set from the second set of x-ray projections, enables selection of a common slice from the first reconstructed tomographic volume data set and the second reconstructed tomographic volume data set, renders and displays intermediate image representations of the sample that provide x-ray absorption intensities of elements within the sample for the selected common slice, enables selection of pixels of a region of interest (ROI) within the intermediate image representations of the sample.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS in the accompanying drawings, reference characters refer to the same parts throughout the different views. The drawings are not necessarily to scale; emphasis has instead been placed upon illustrating the principles of the invention. Of the drawings.

Figure 1:
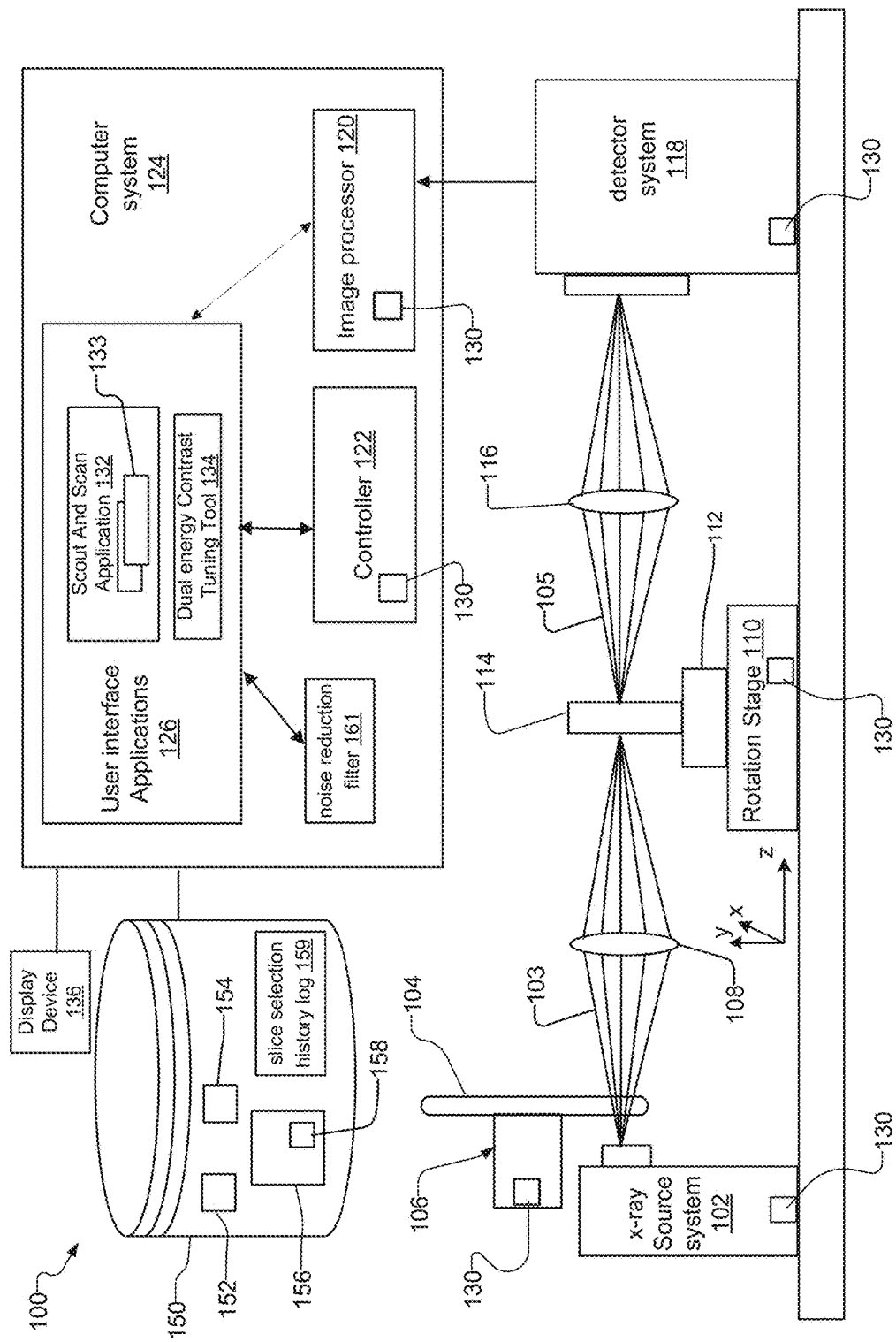
FIG. 1 is a schematic diagram of a lens-based x-ray imaging microscopy system that is used in connection with the present invention, in one example.
Figure 2:
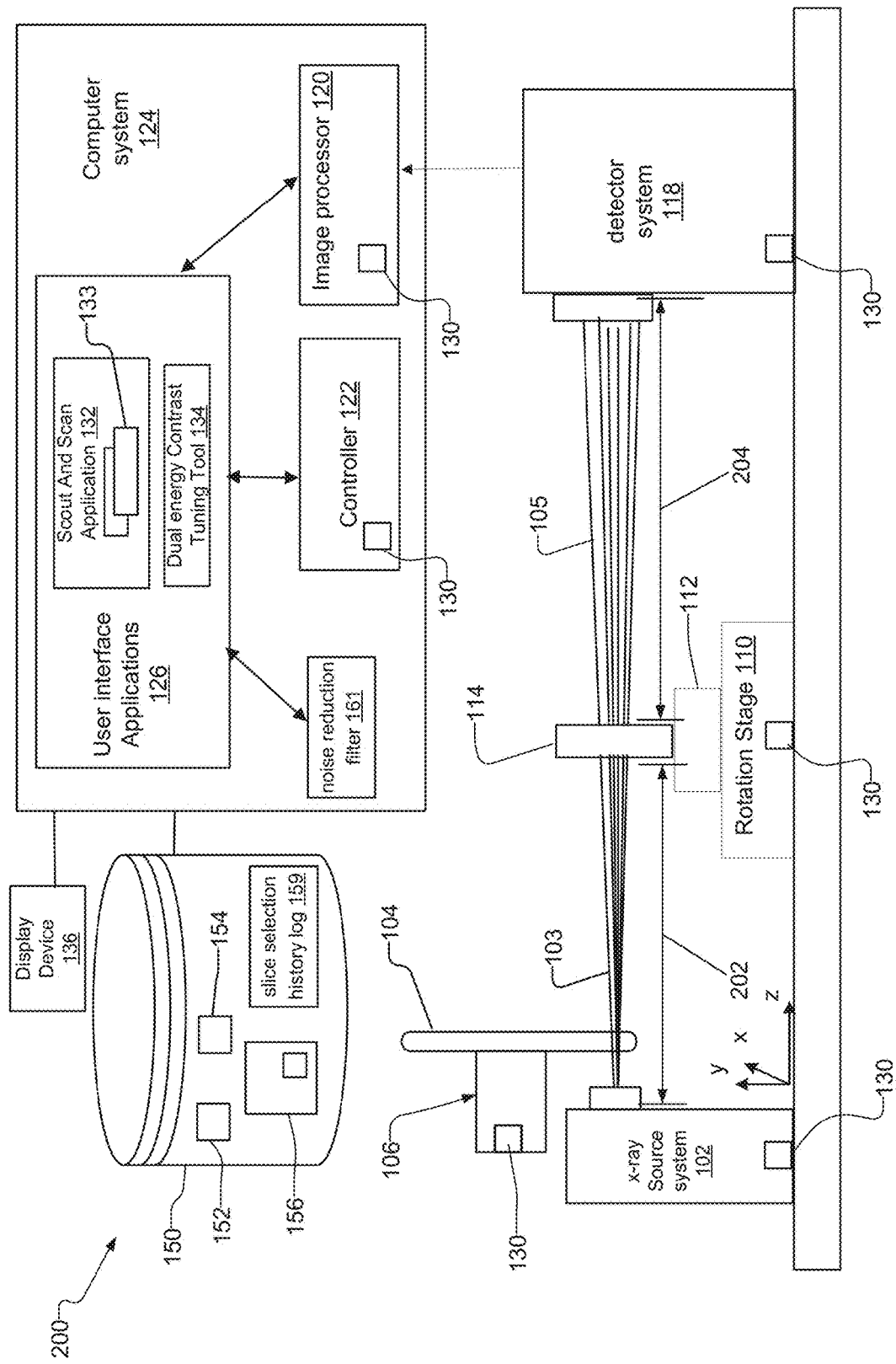
FIG. 2 is a schematic diagram of a projection-based x-ray imaging microscopy system that is used in connection with the present invention, in another example.
Figure 4:
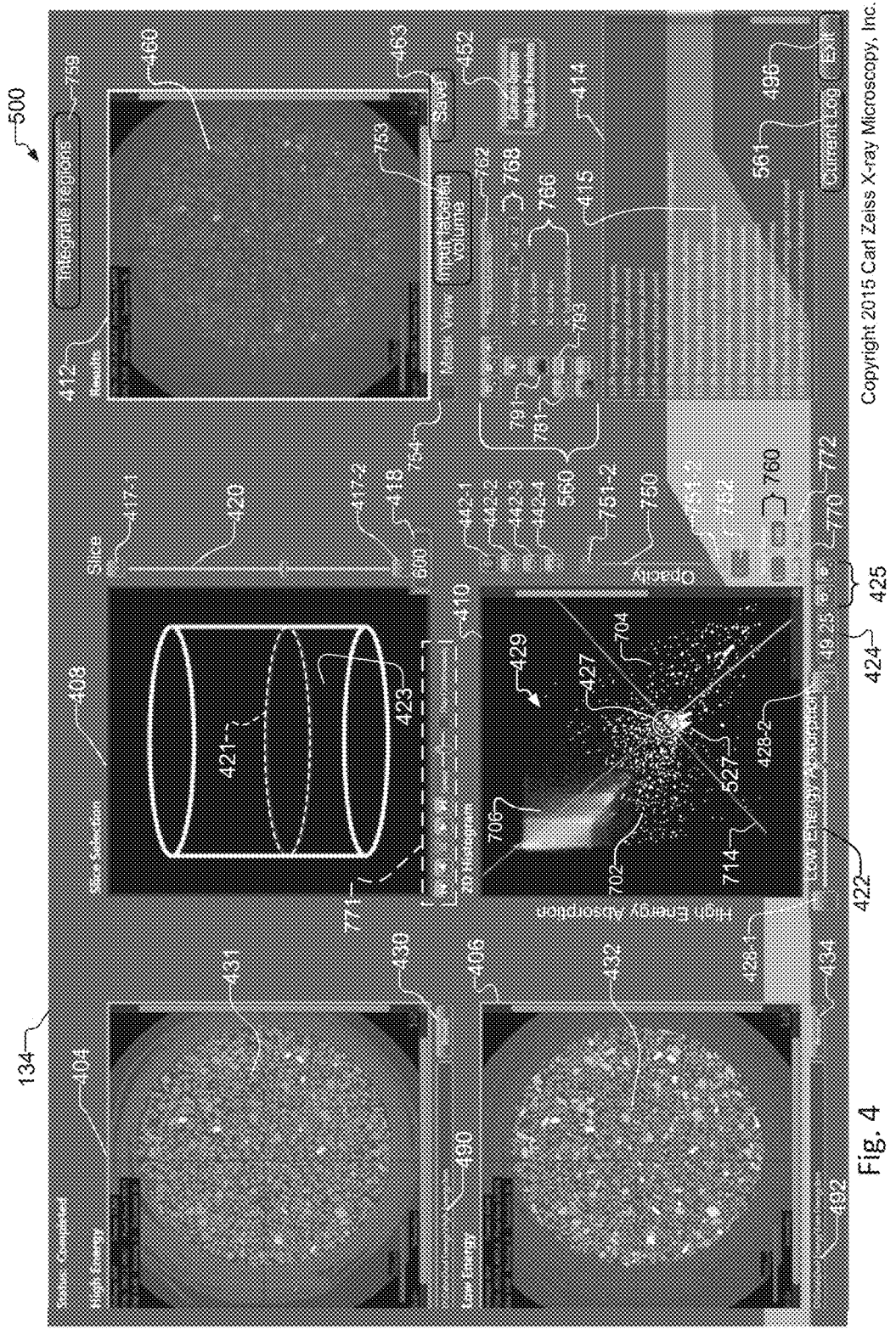
FIG. 4 illustrates a graphical user interface of a dual energy (DE) tuning tool application, or tuning tool, displaying exemplary images of a sample, a slice histogram, and a synthetic slice of the sample rendered in the Results window.
Figure 6A:
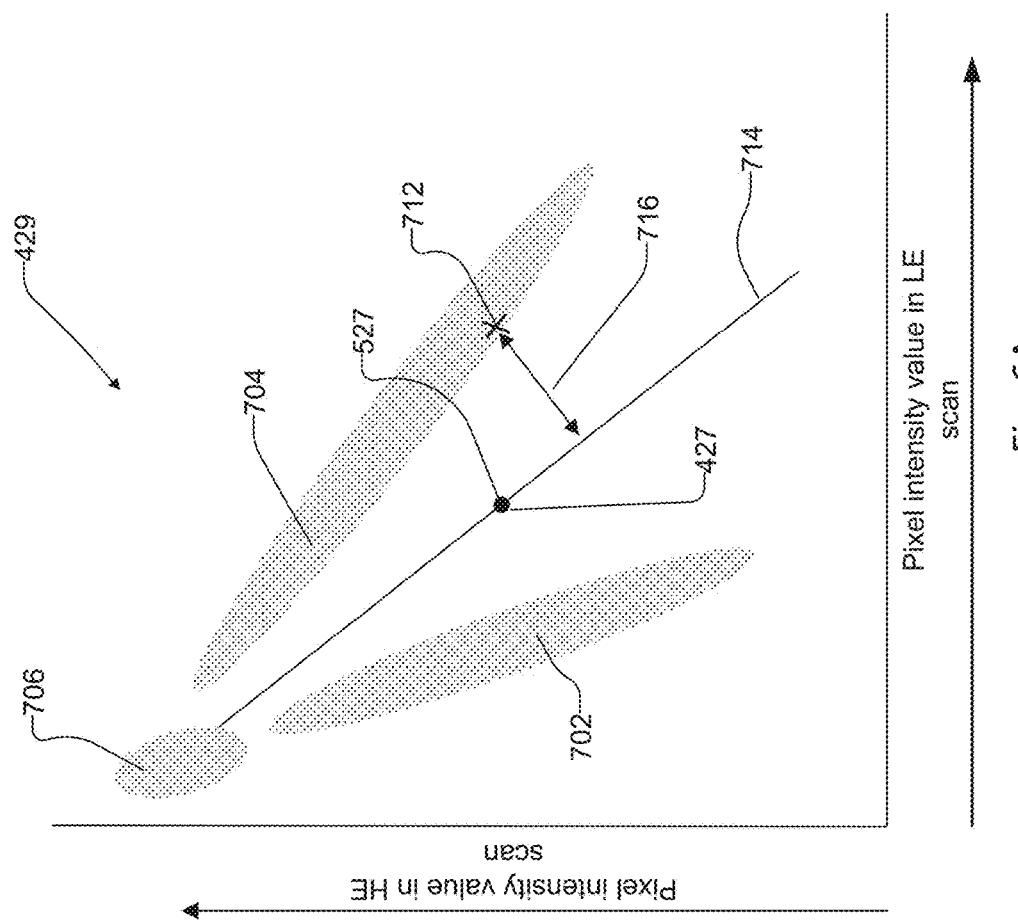
Figure 6B:
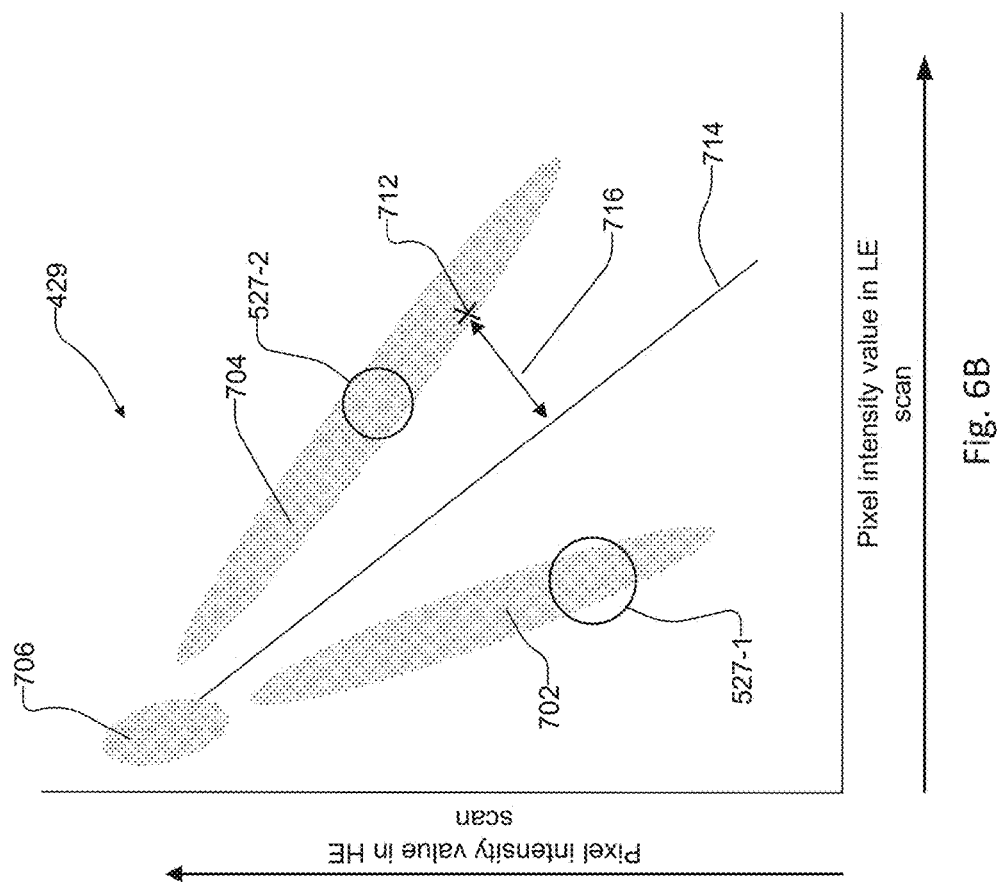
Figure 7A:
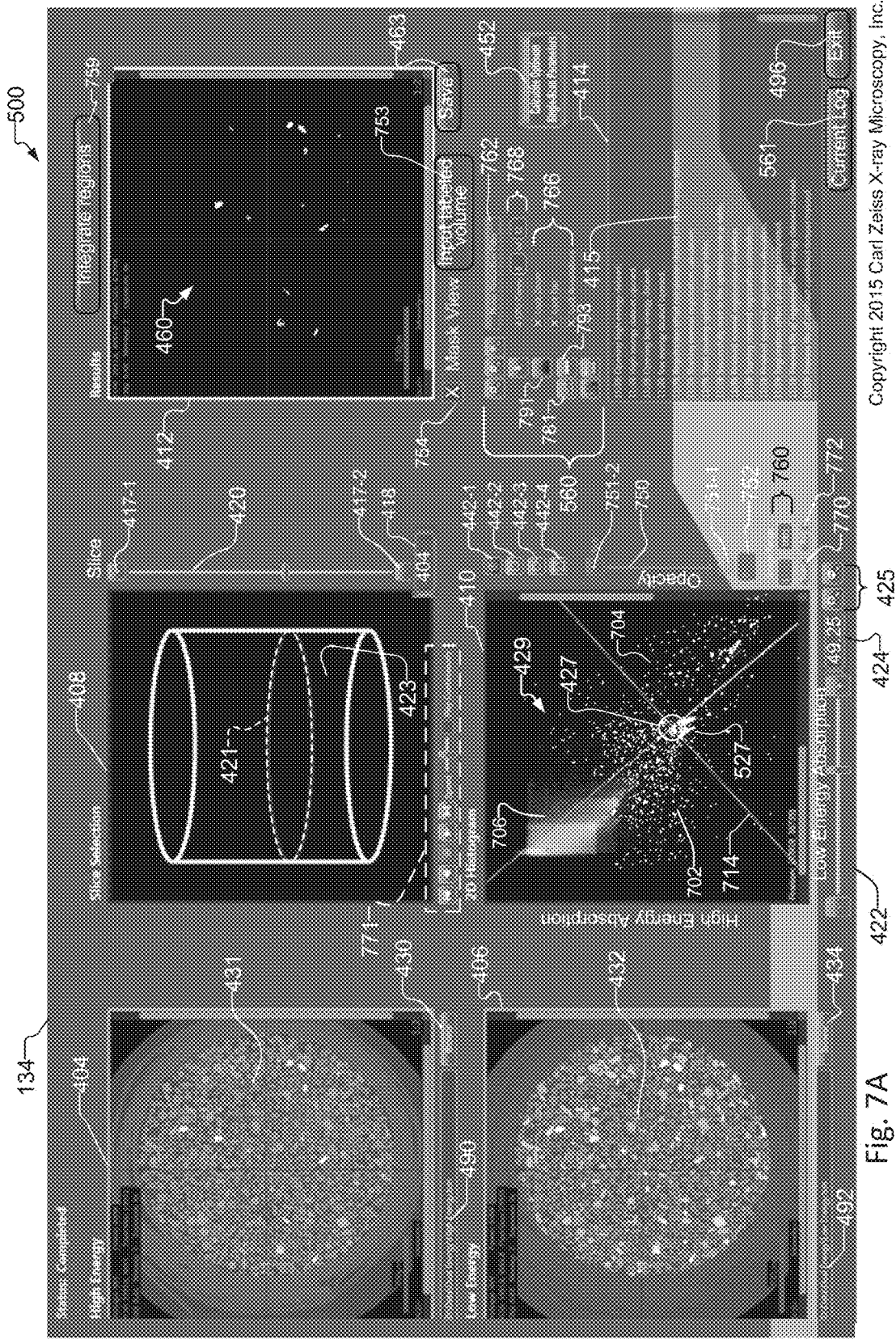
Figure 7B:
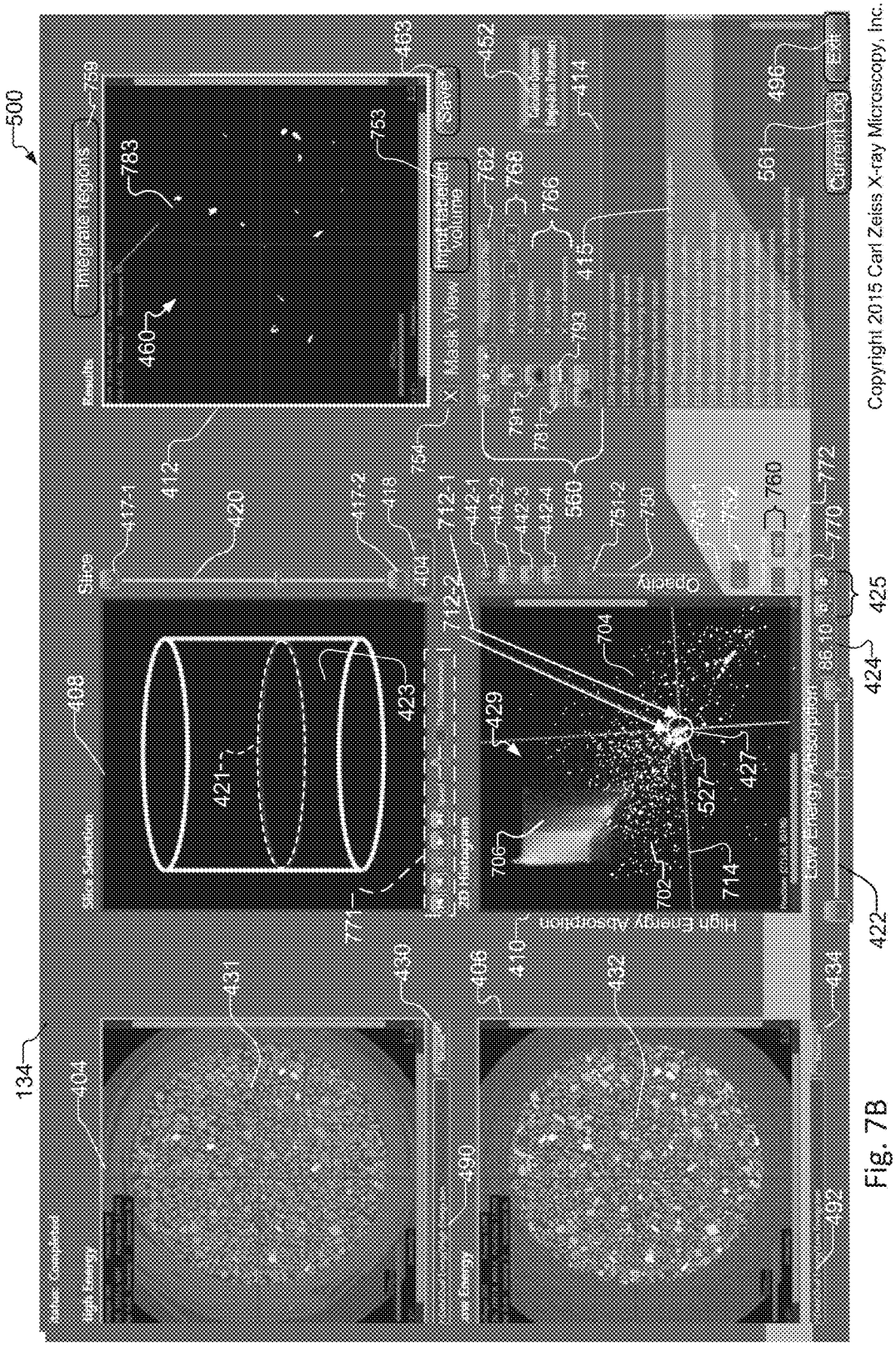
Figure 7C:
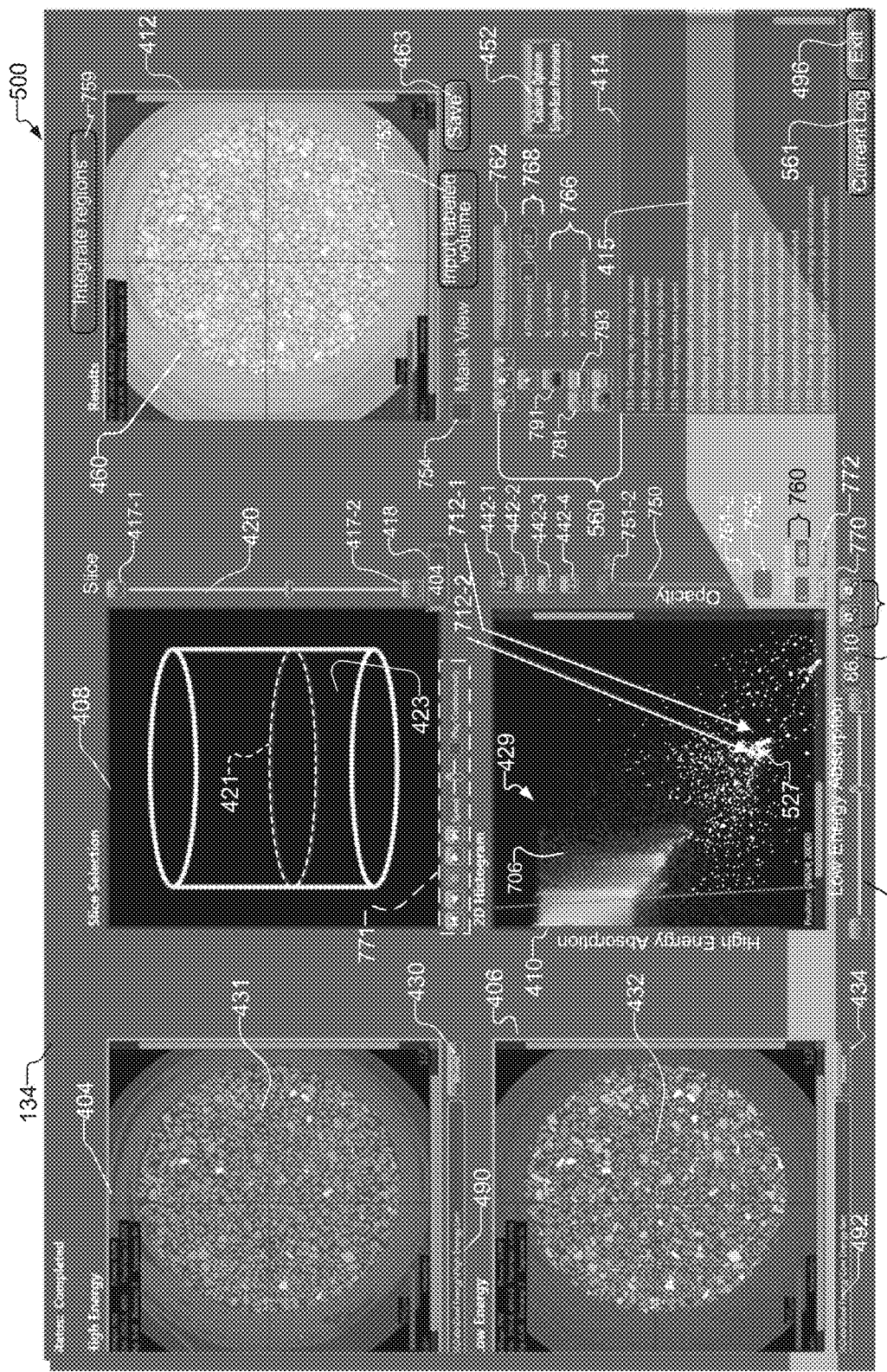
Figure 7D:
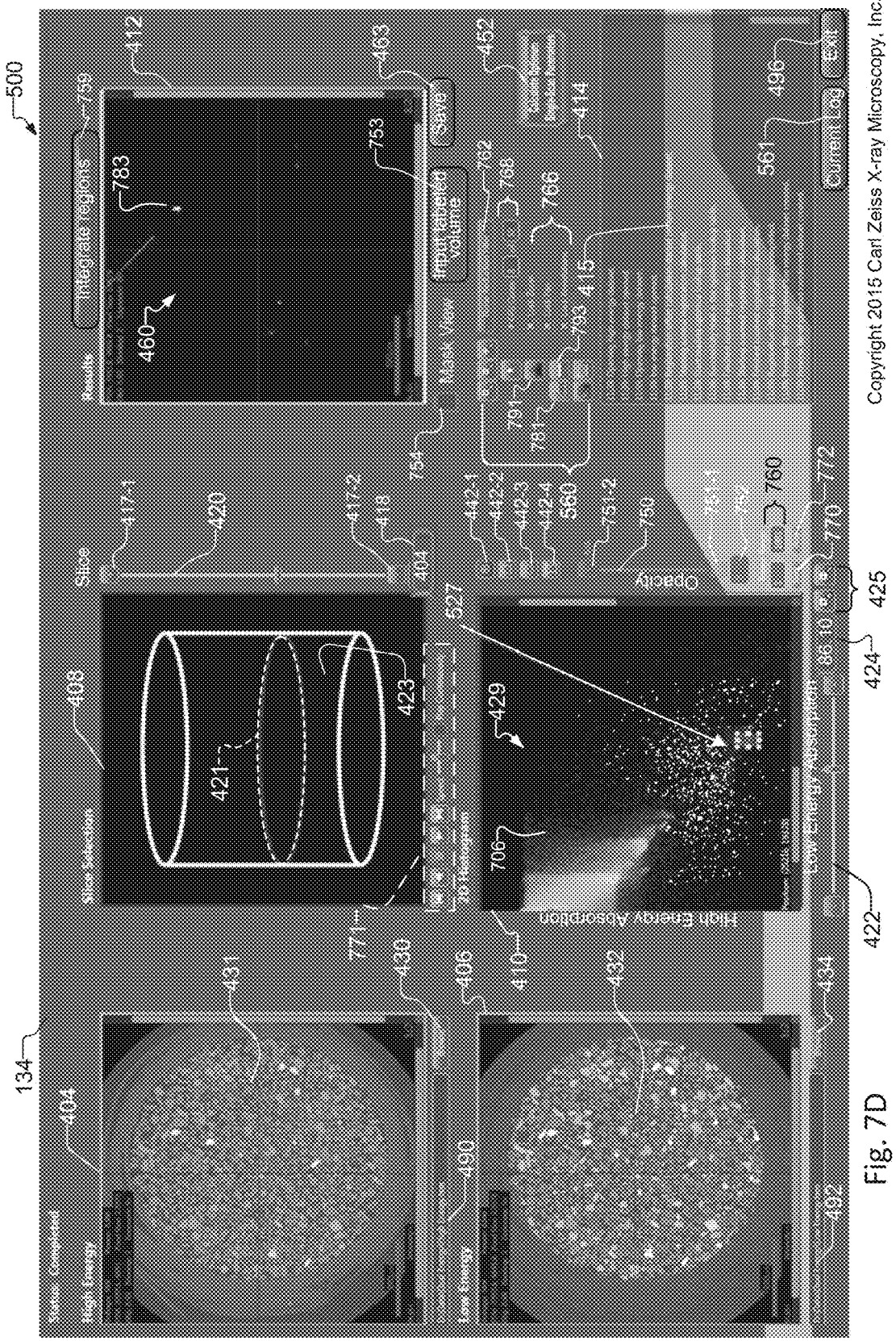
Figure 7E:
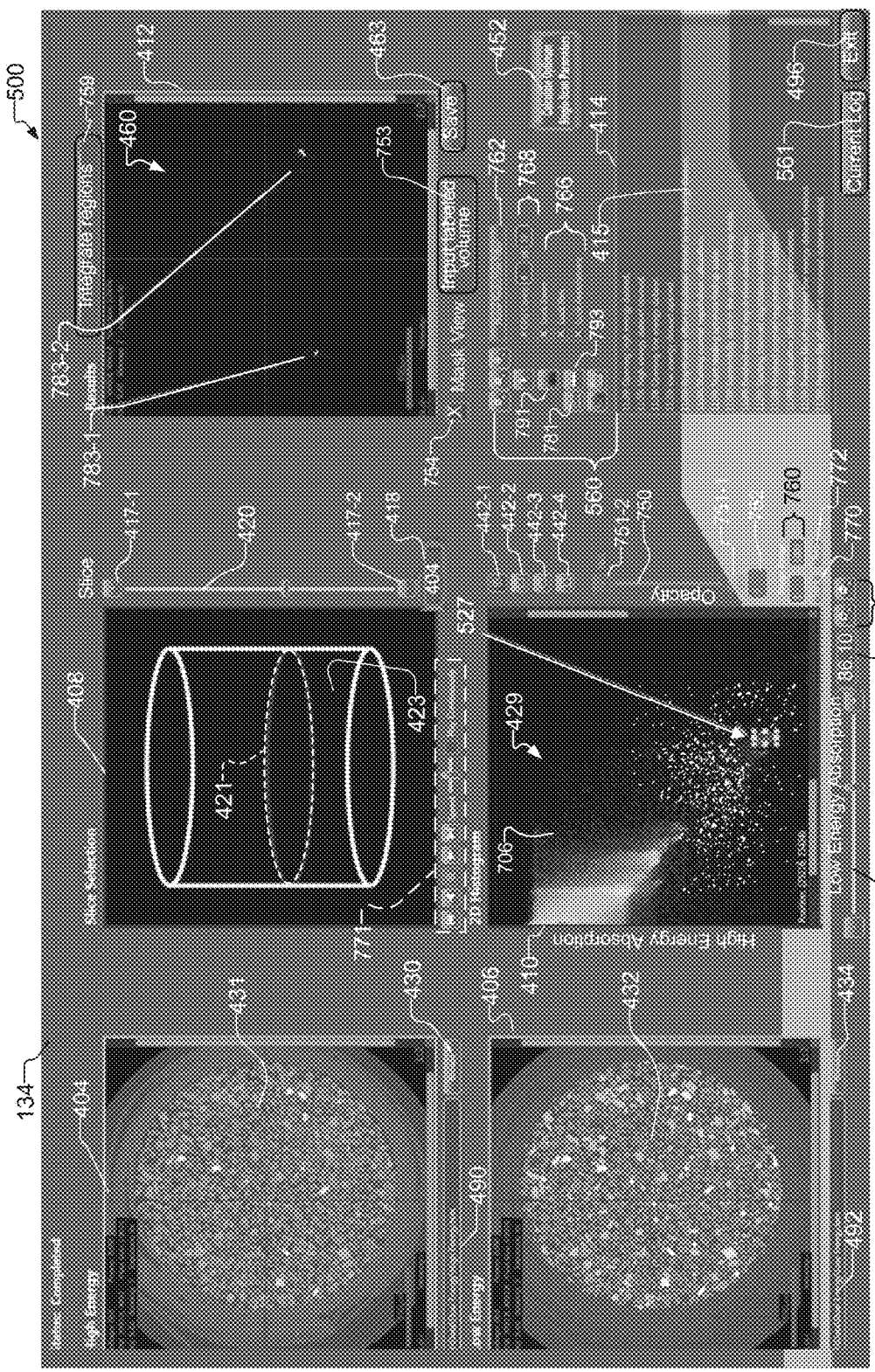
Figure 8:
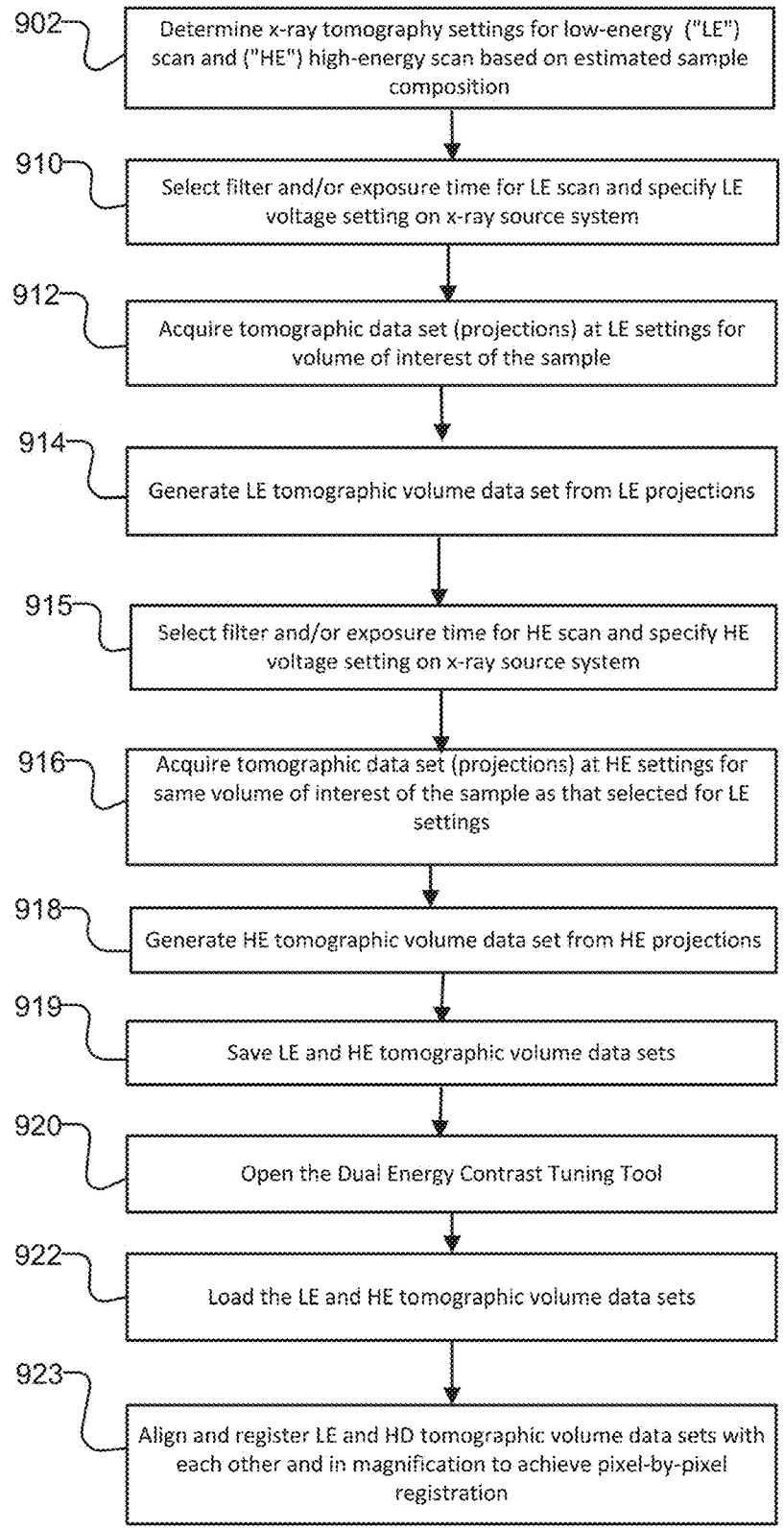
Figure 9:
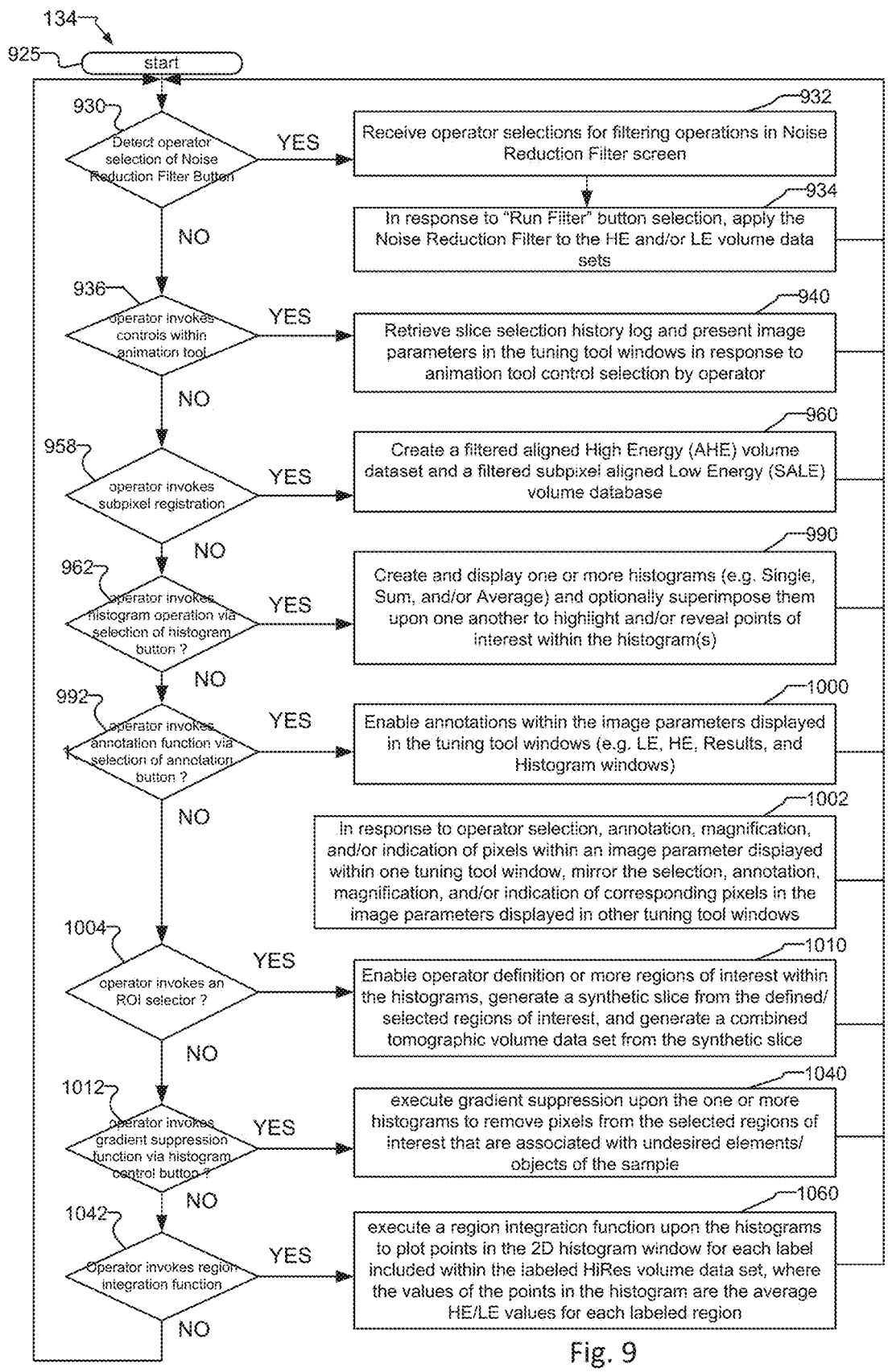
Figure 10:
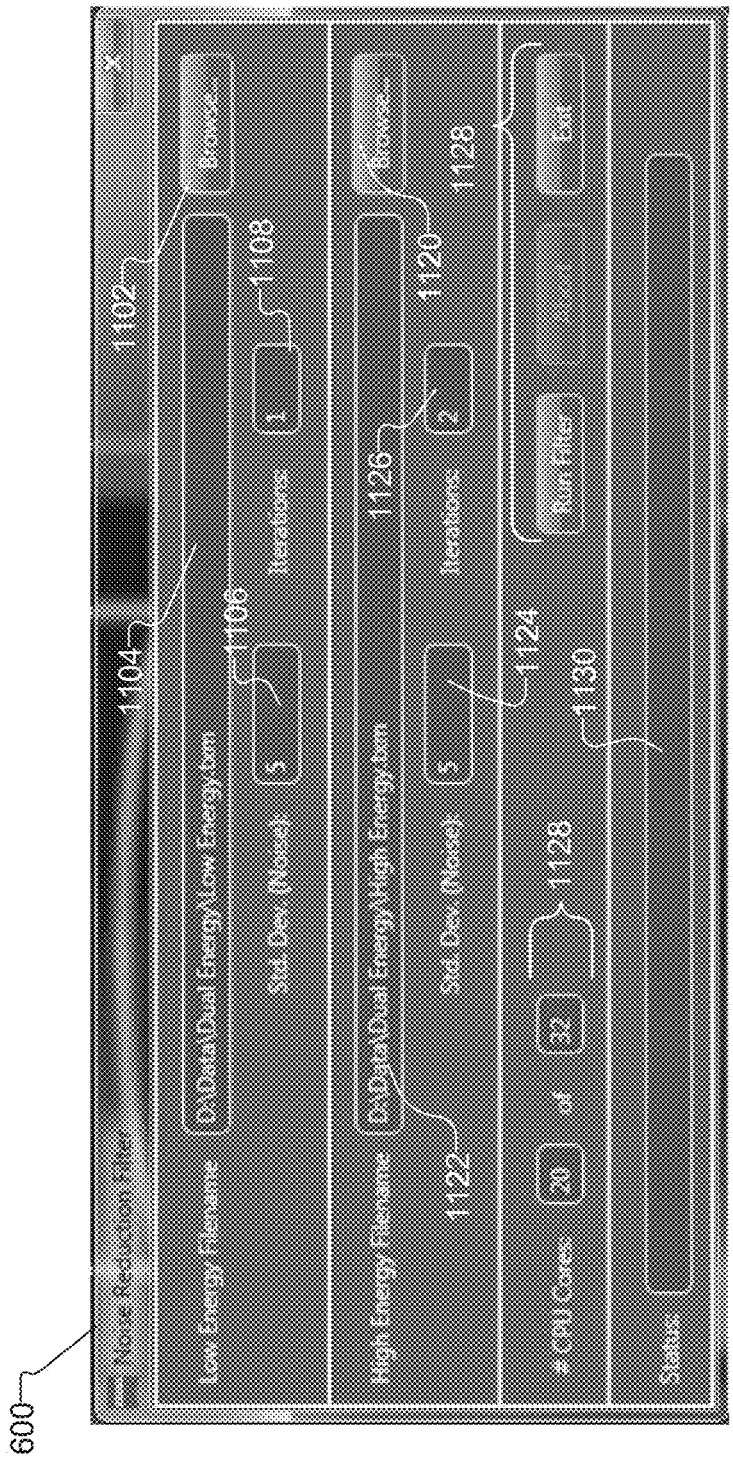
Figure 11:
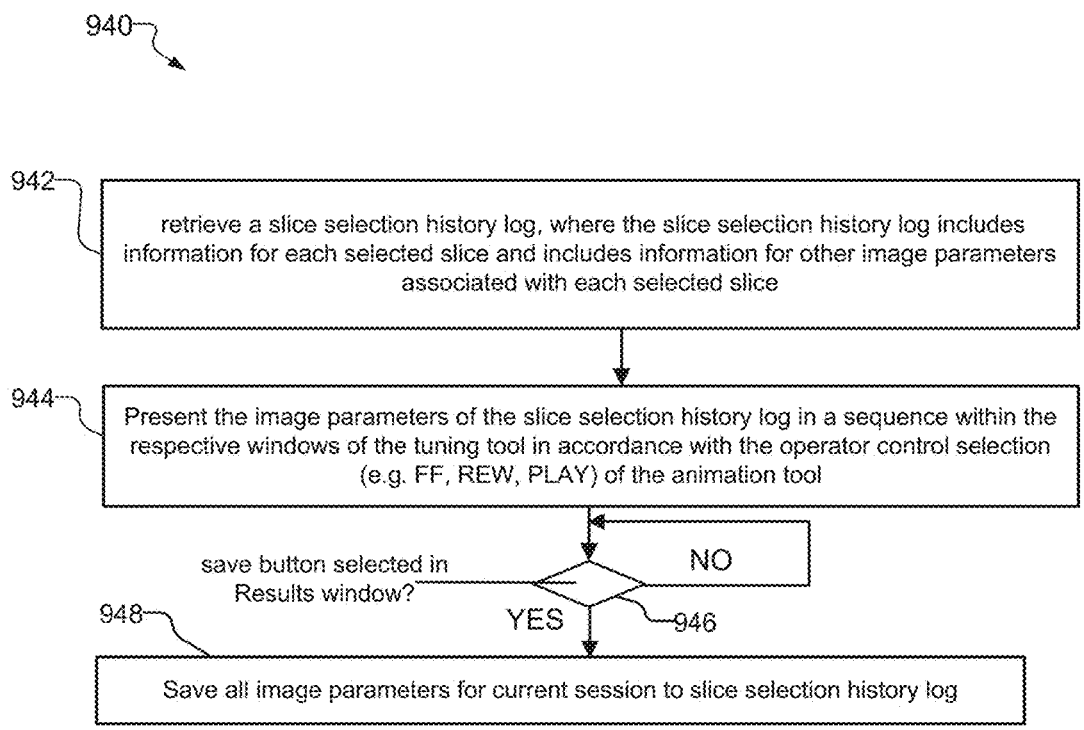
Figure 12:
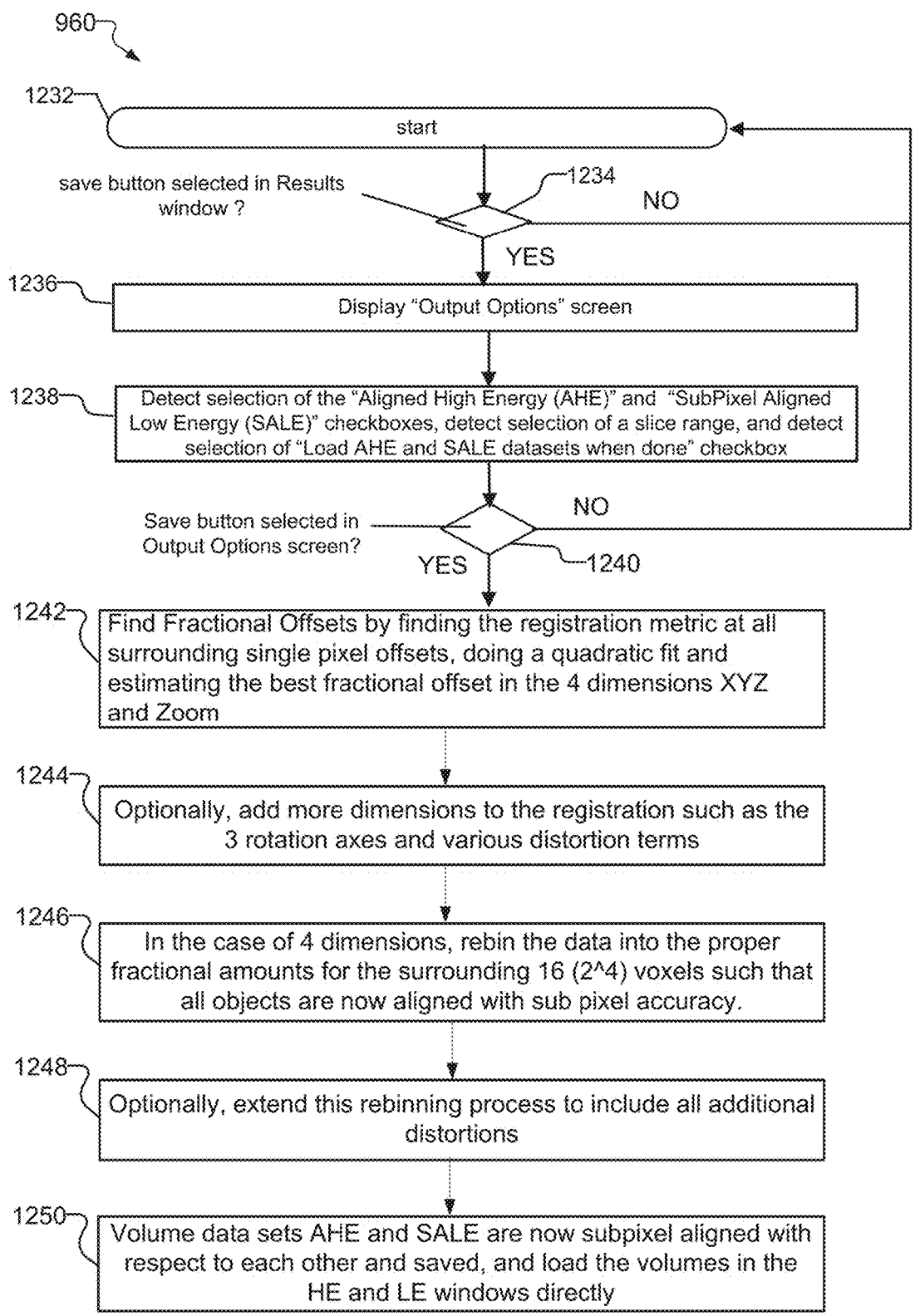
Figure 13:
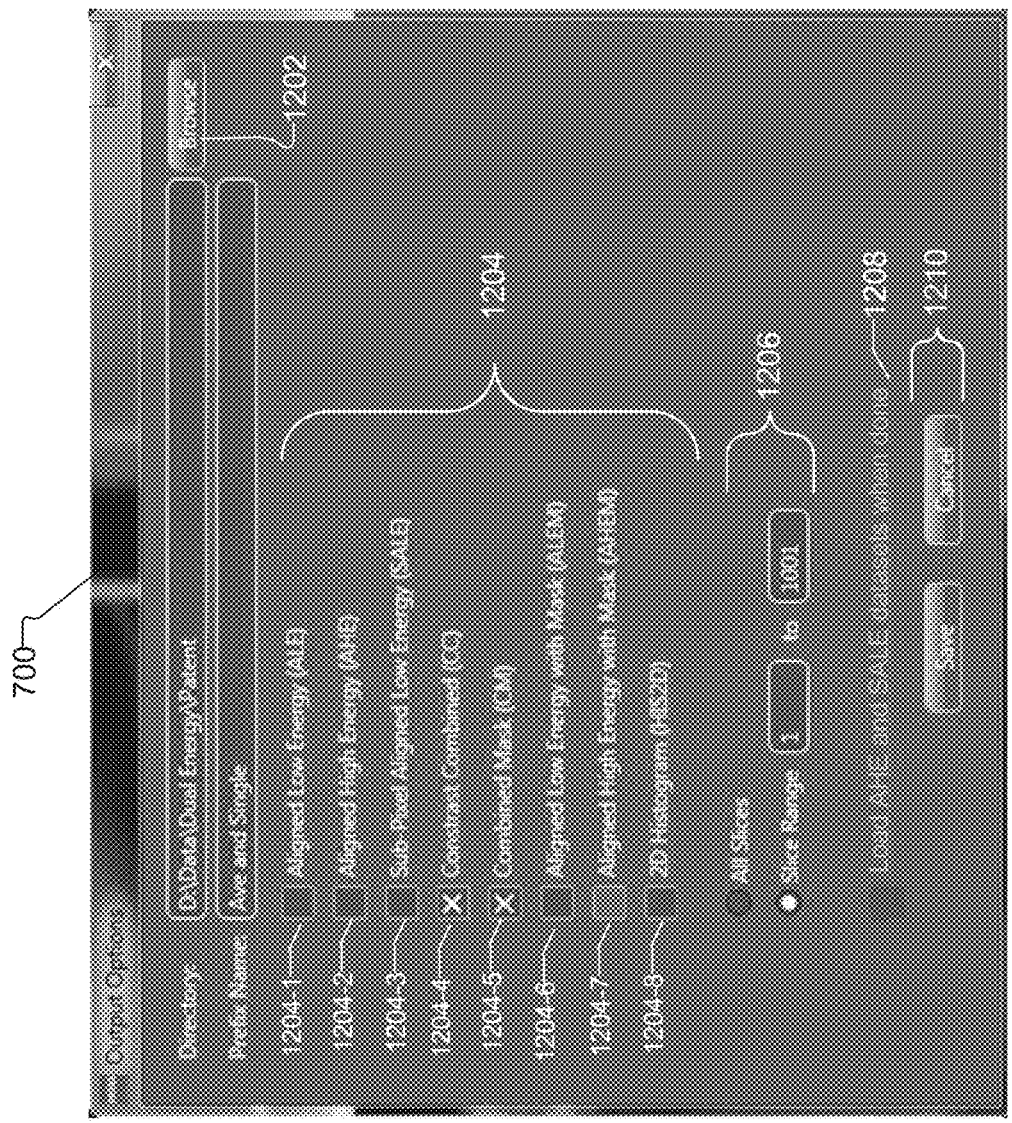
Figure 14A:
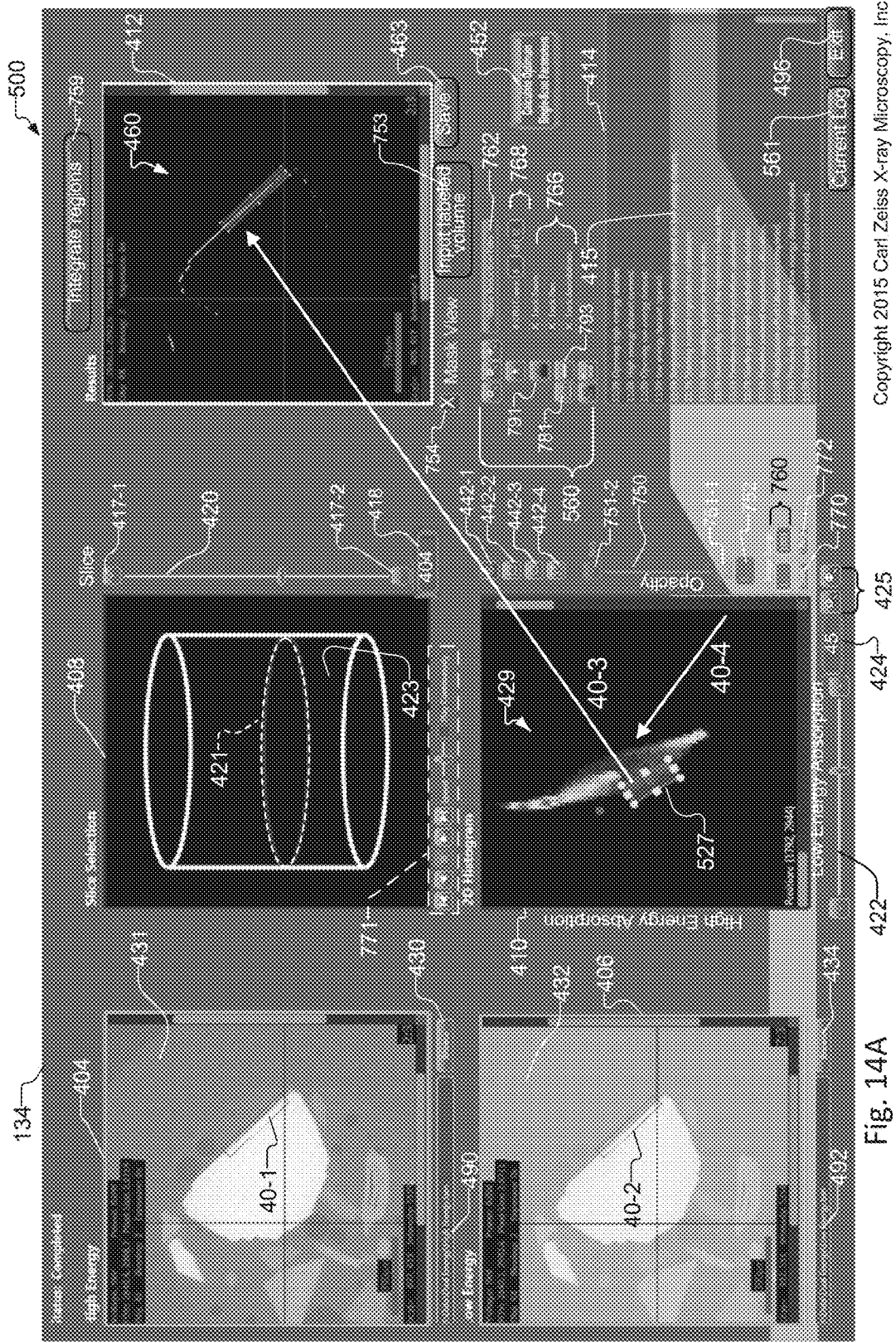
Figure 14B:
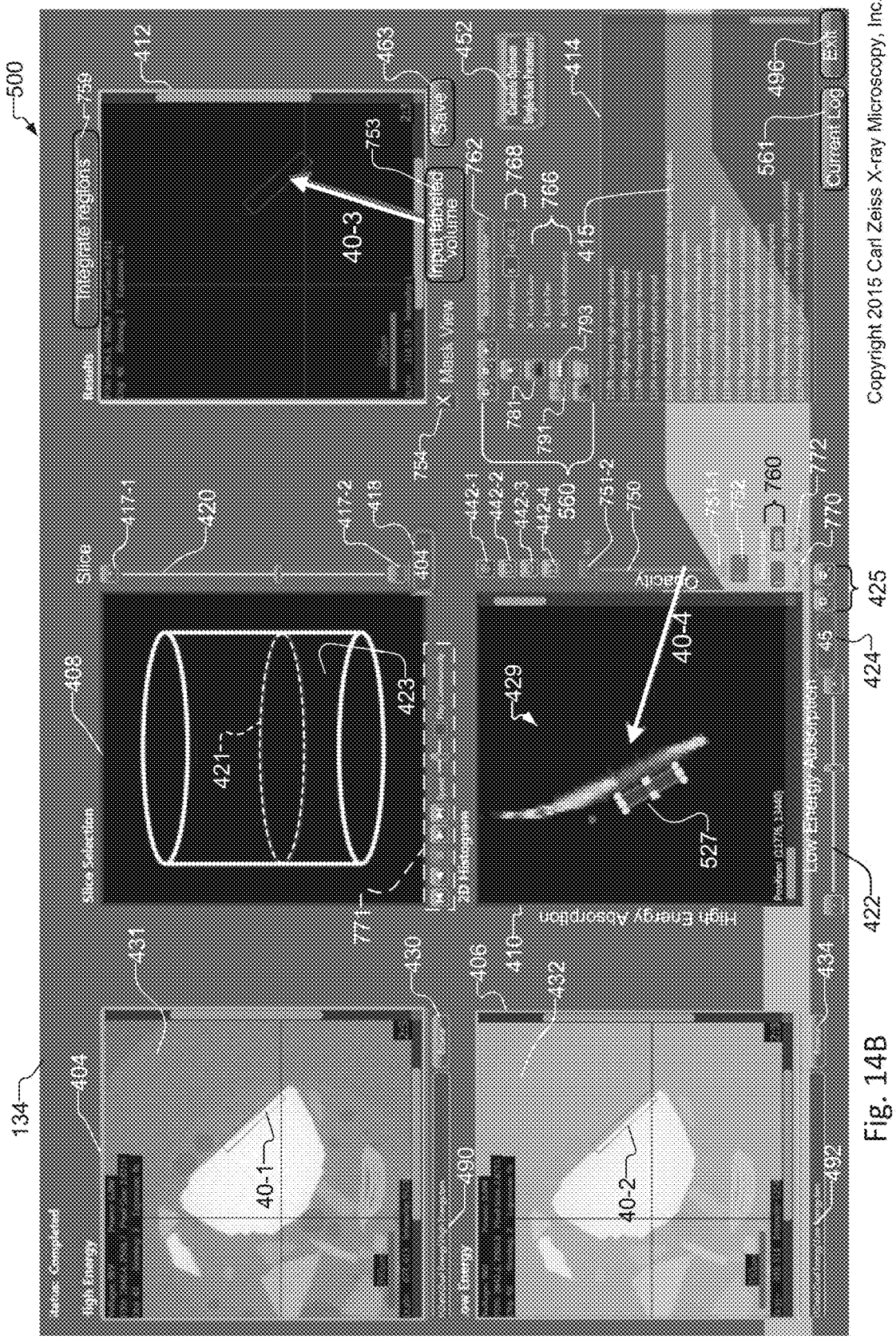
Figure 15:
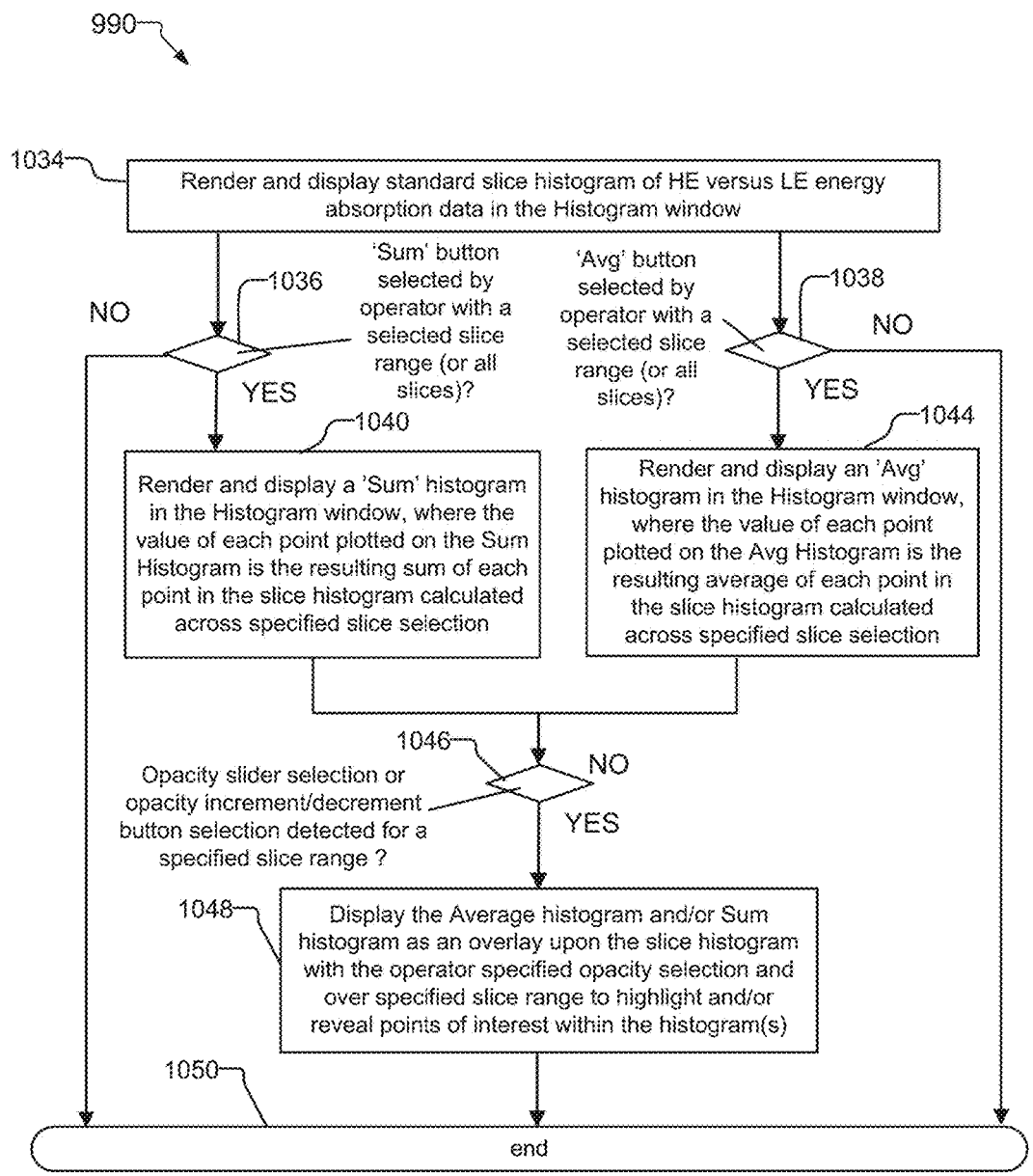
Figure 16A:
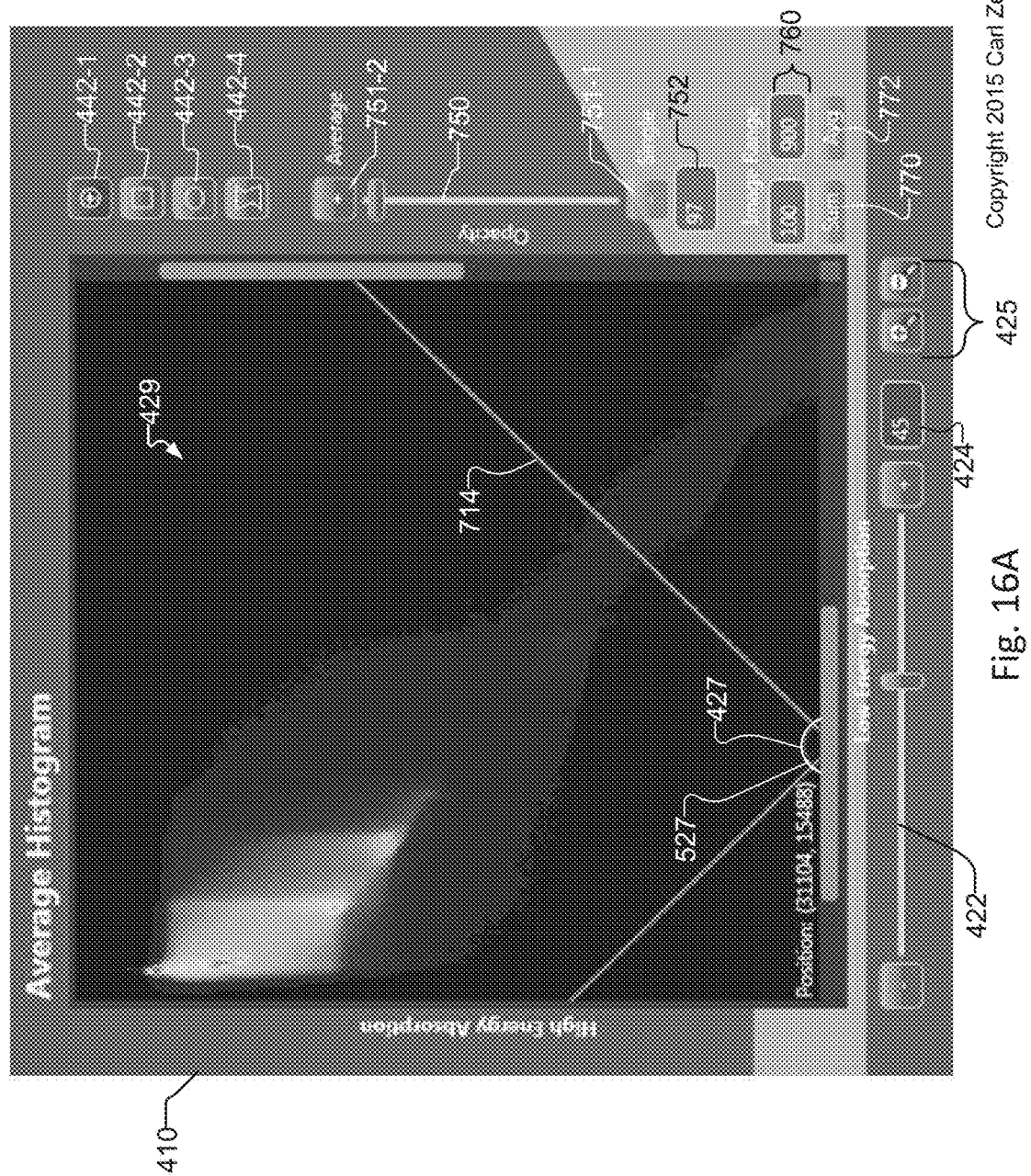
Figure 16B:
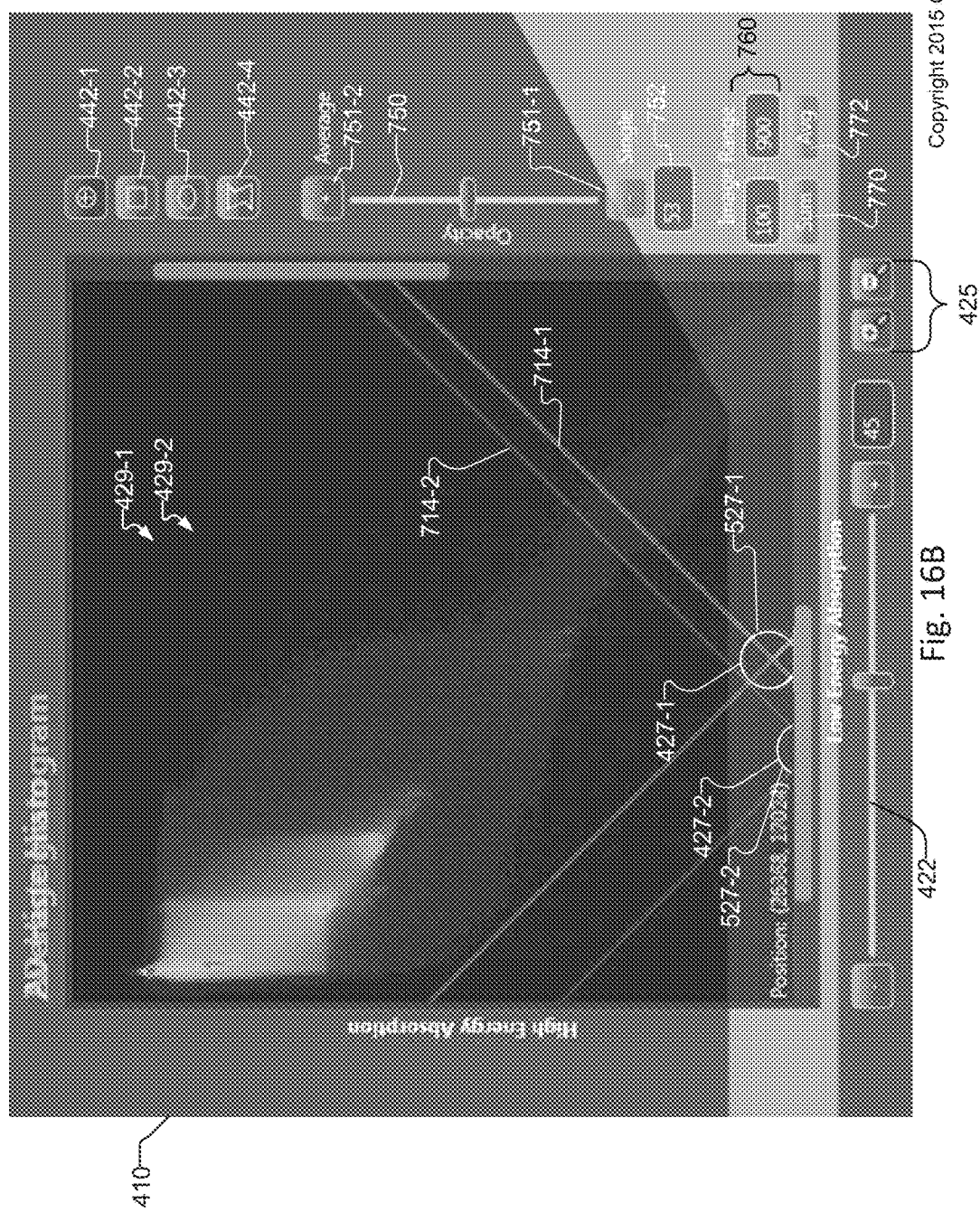
Figure 16C:
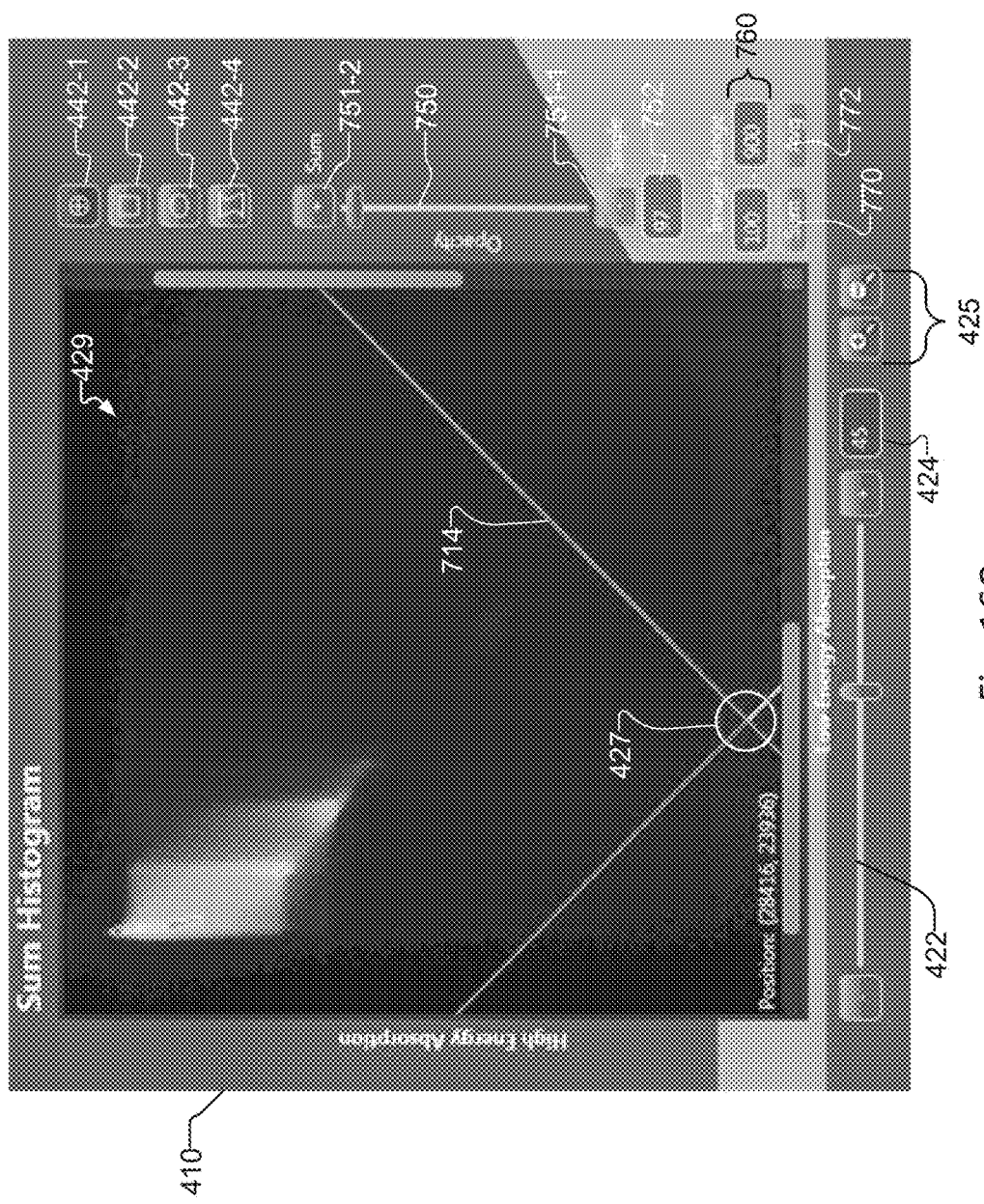
Figure 16D:
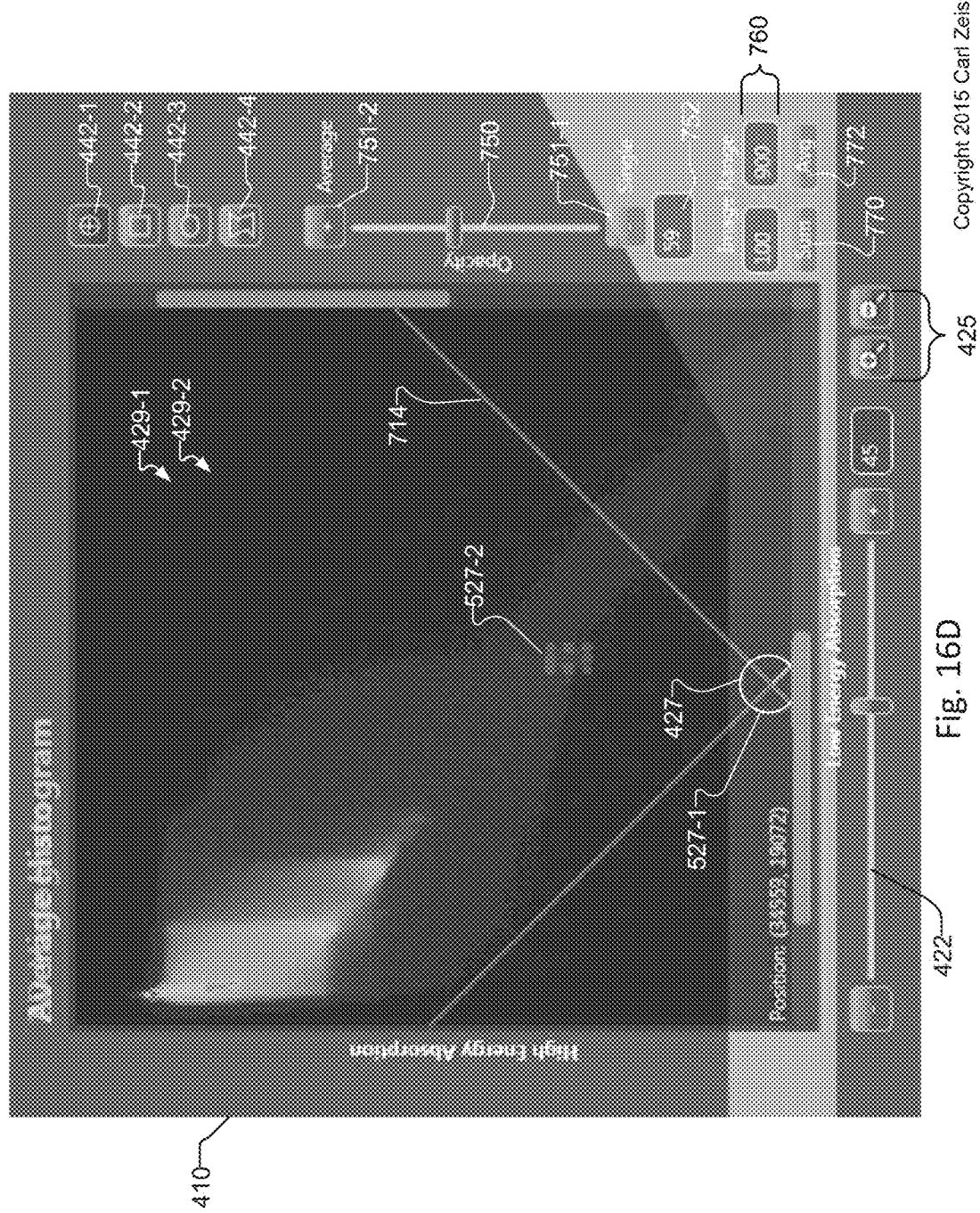
Figure 16E:
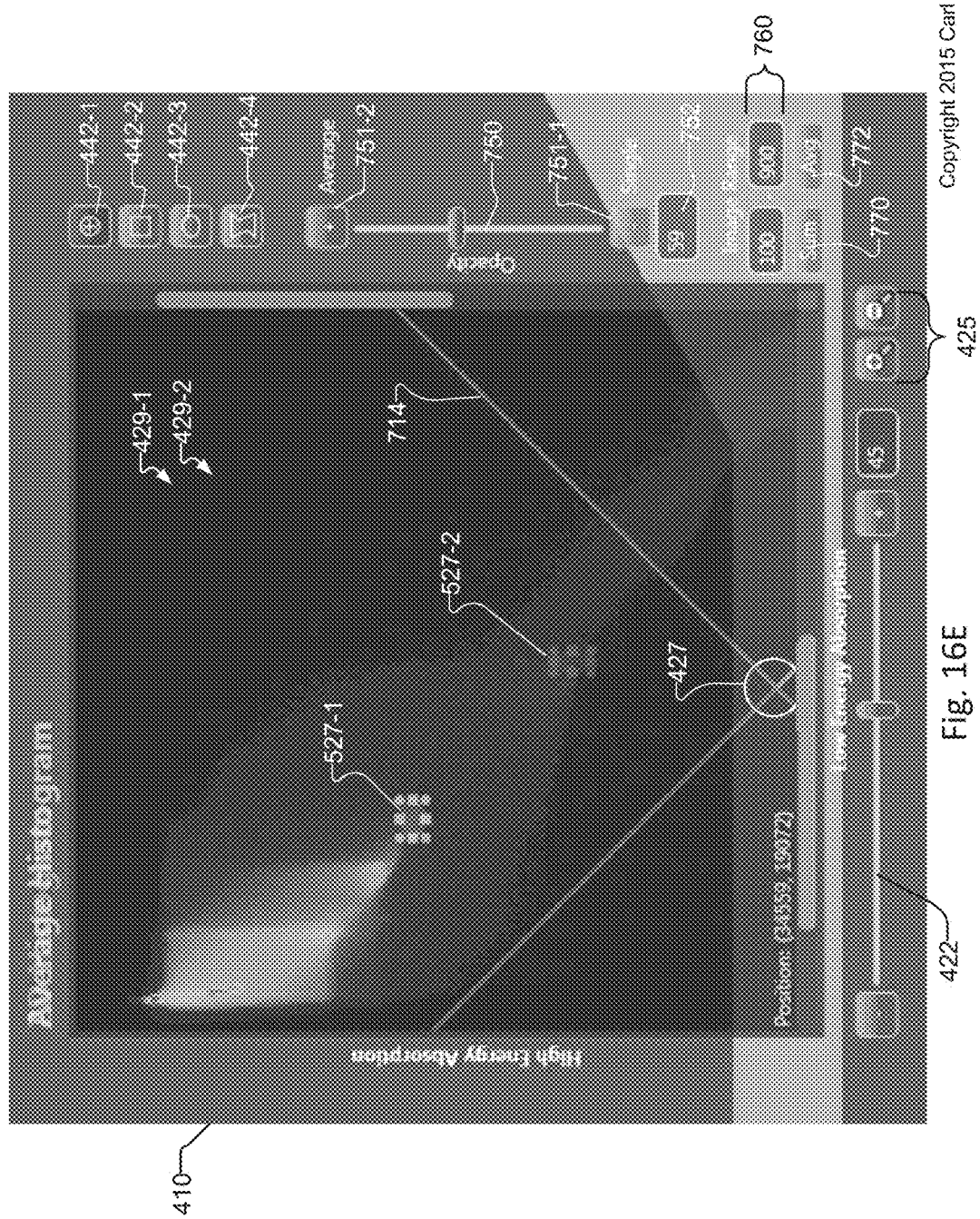
Figure 17:
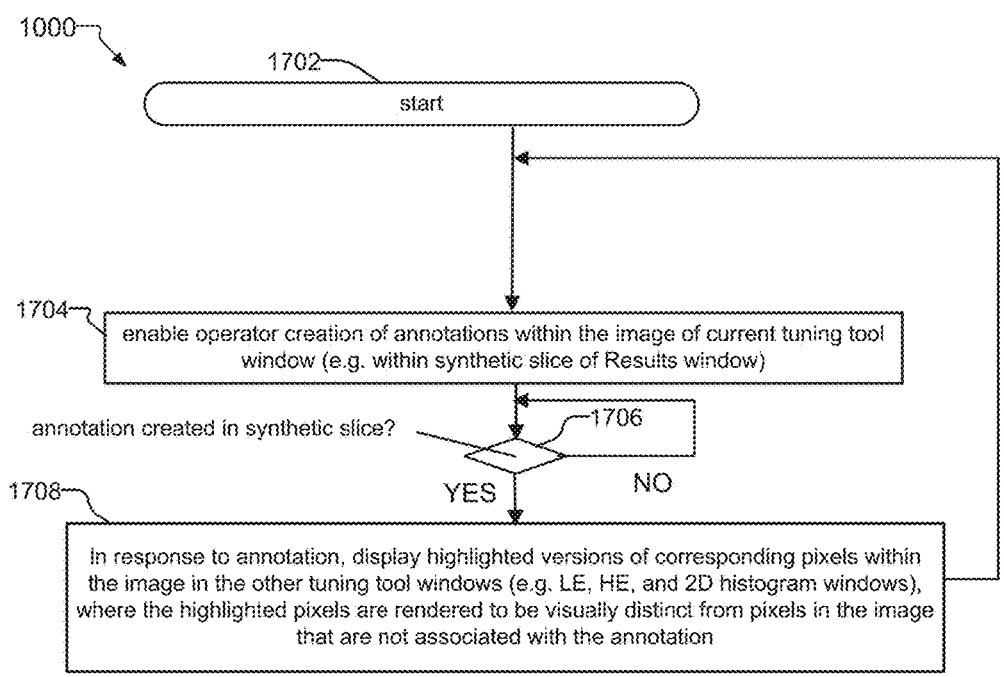
Figure 18:
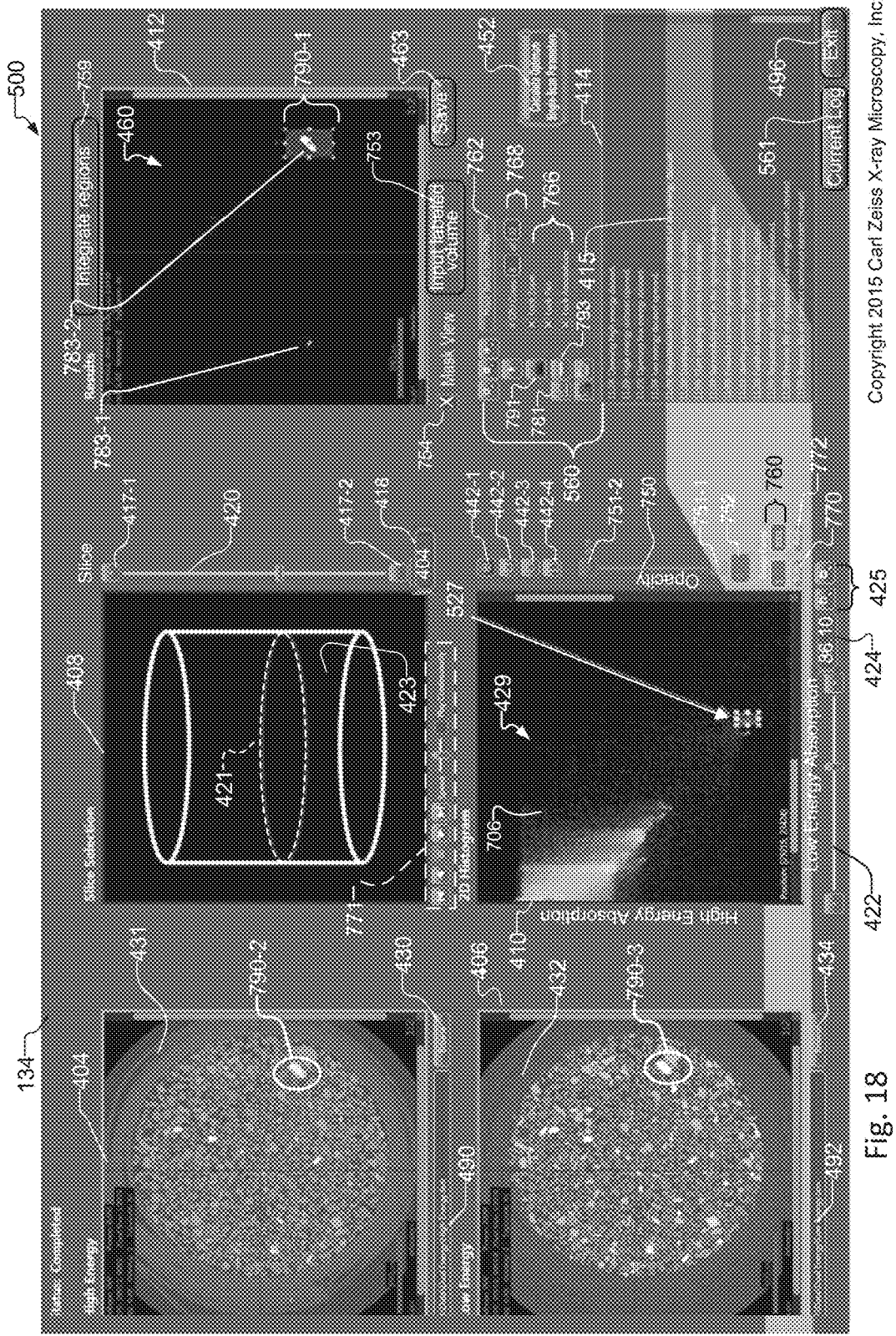
Figure 19A:
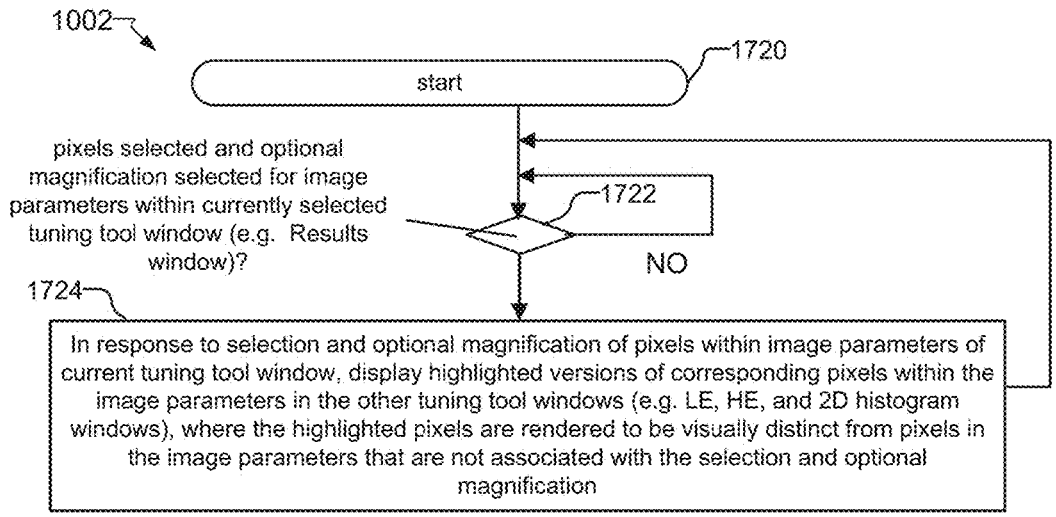
Figure 19B:
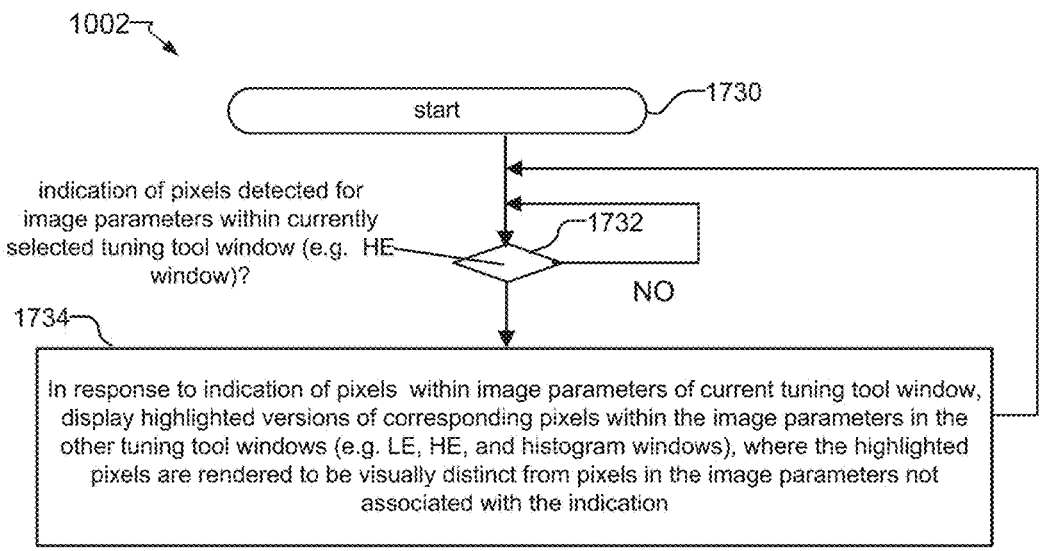
Figure 20A:
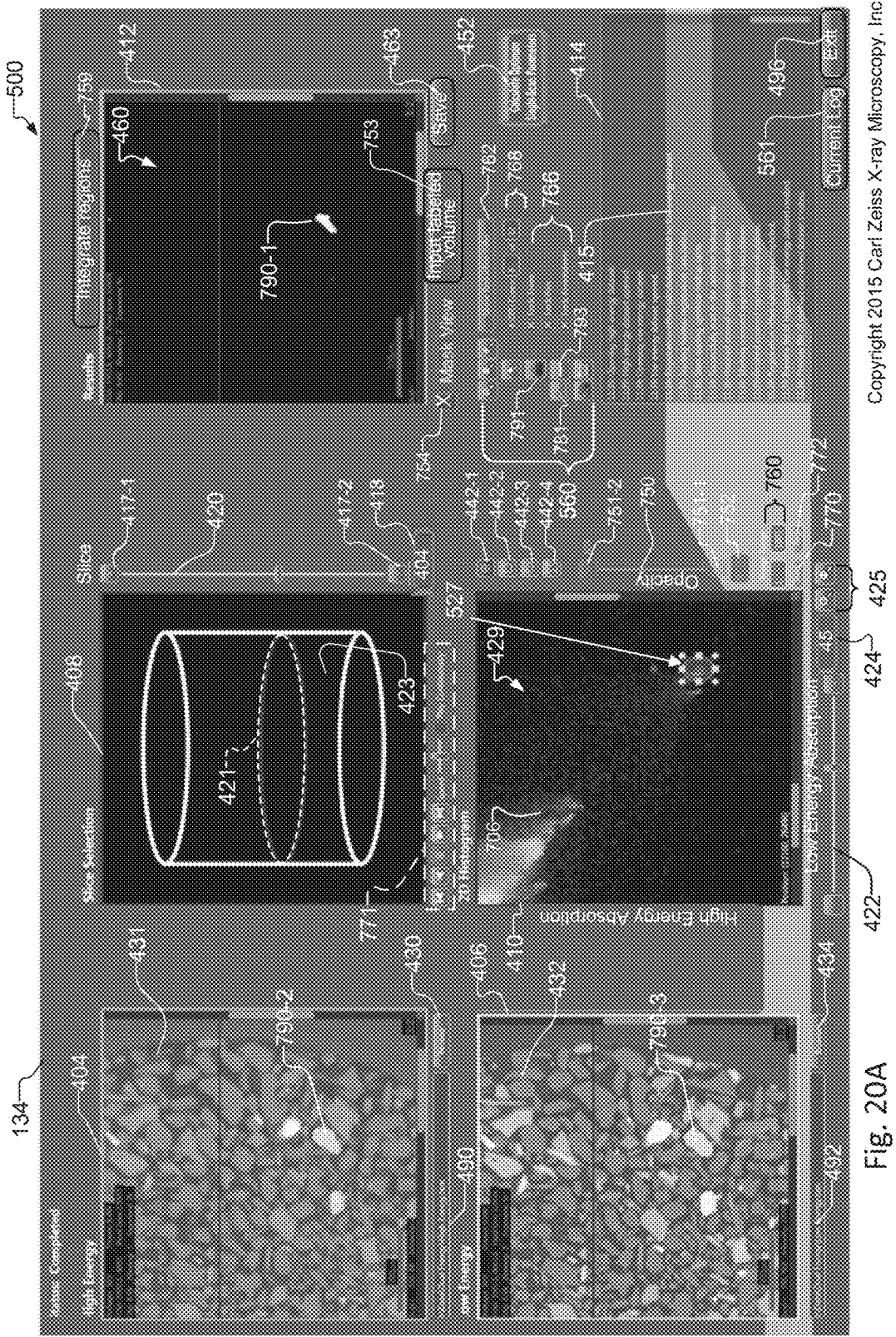
Figure 21:
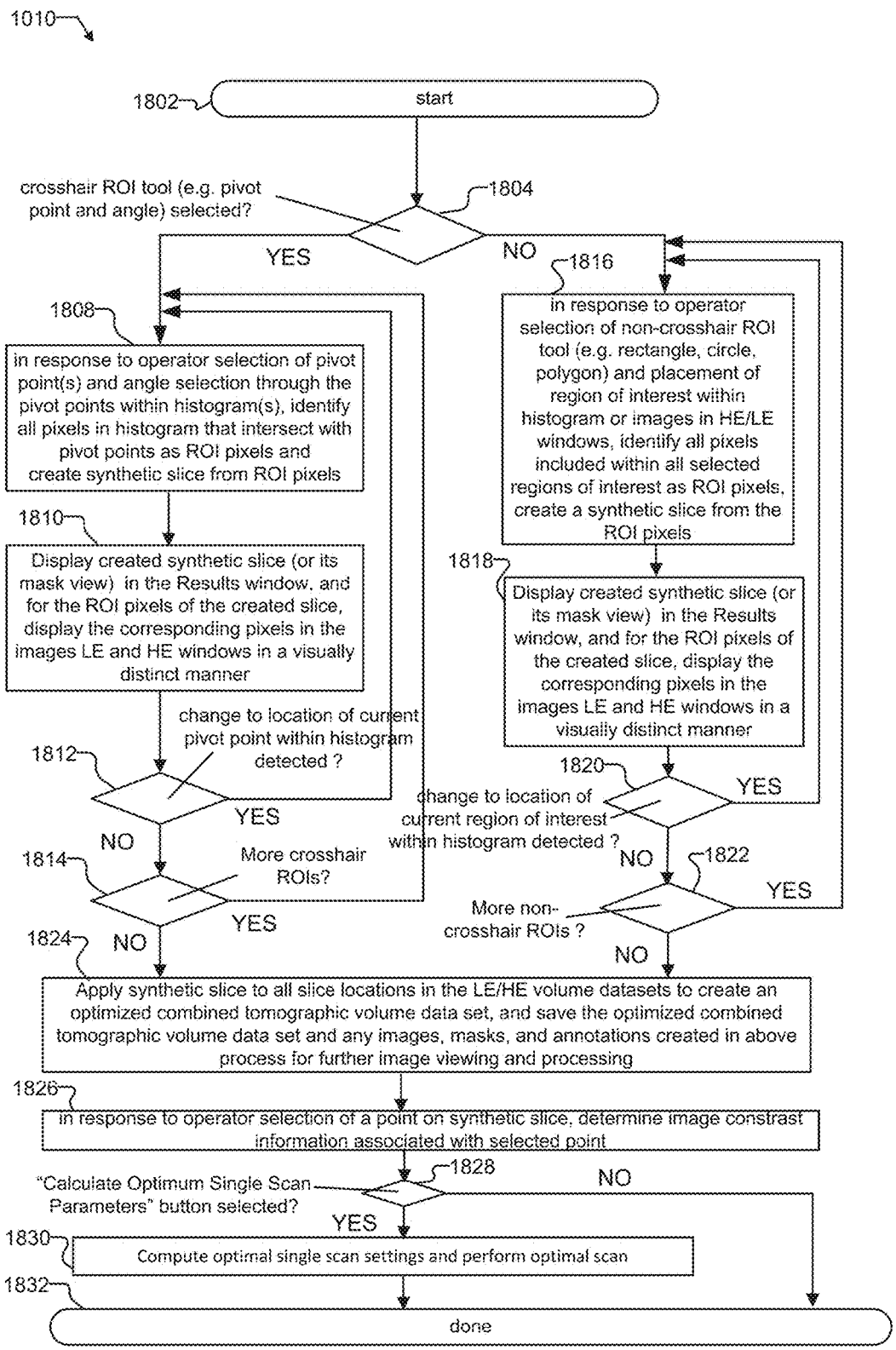
Figure 22A:
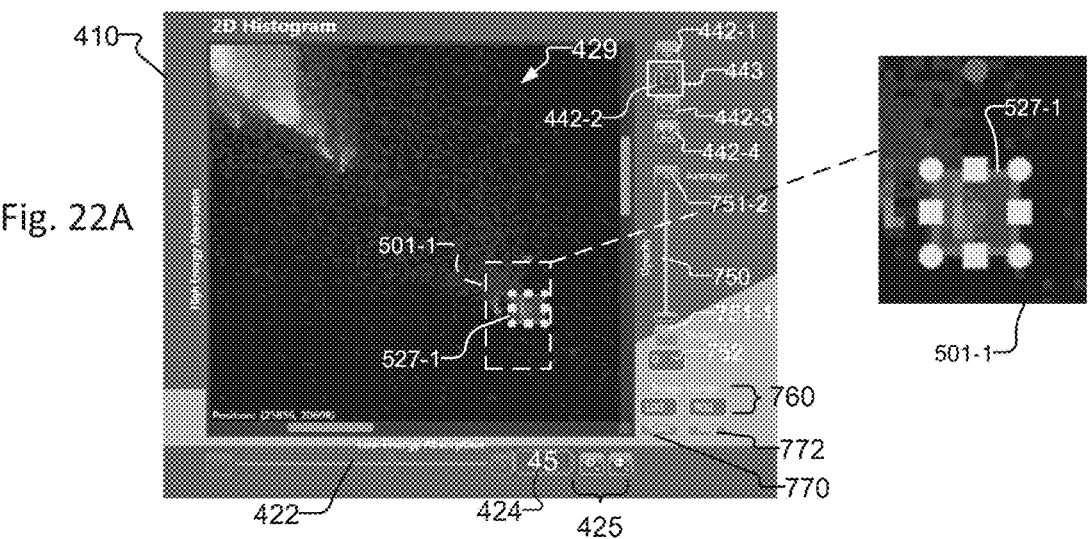
Figure 22B:
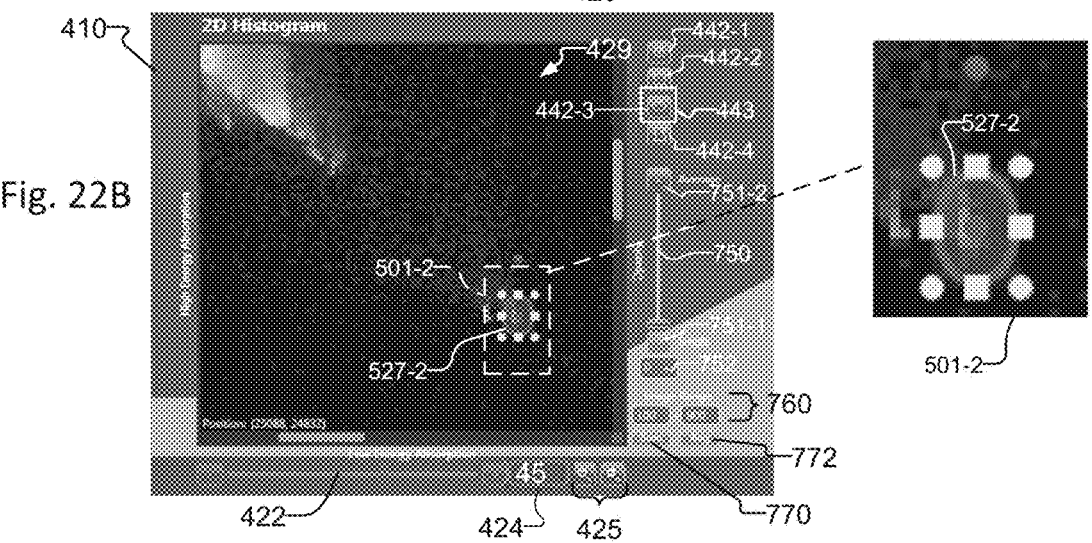
Figure 22C:
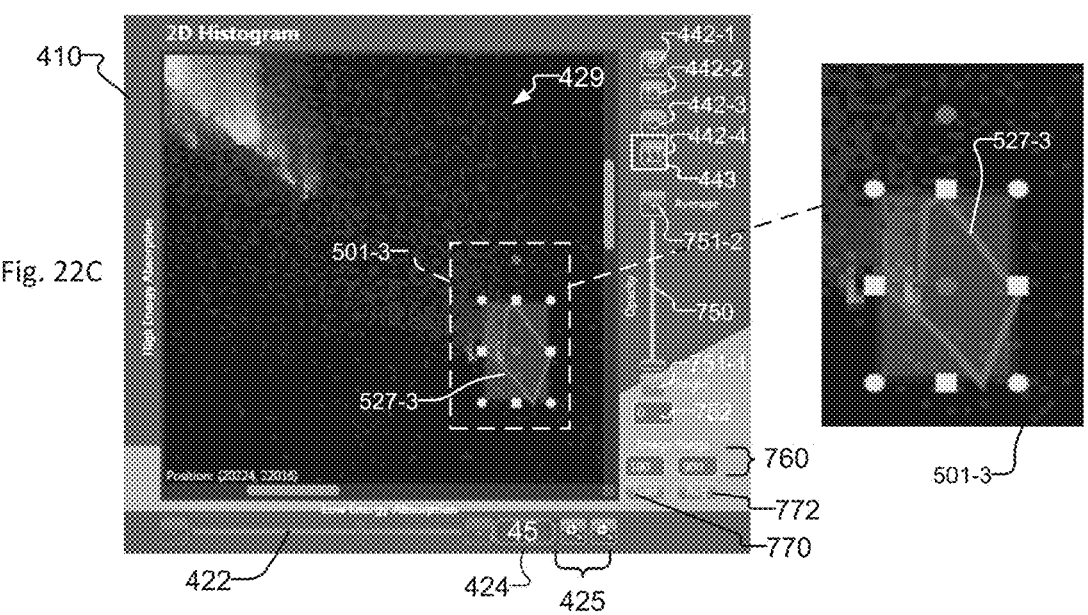
Figure 23:
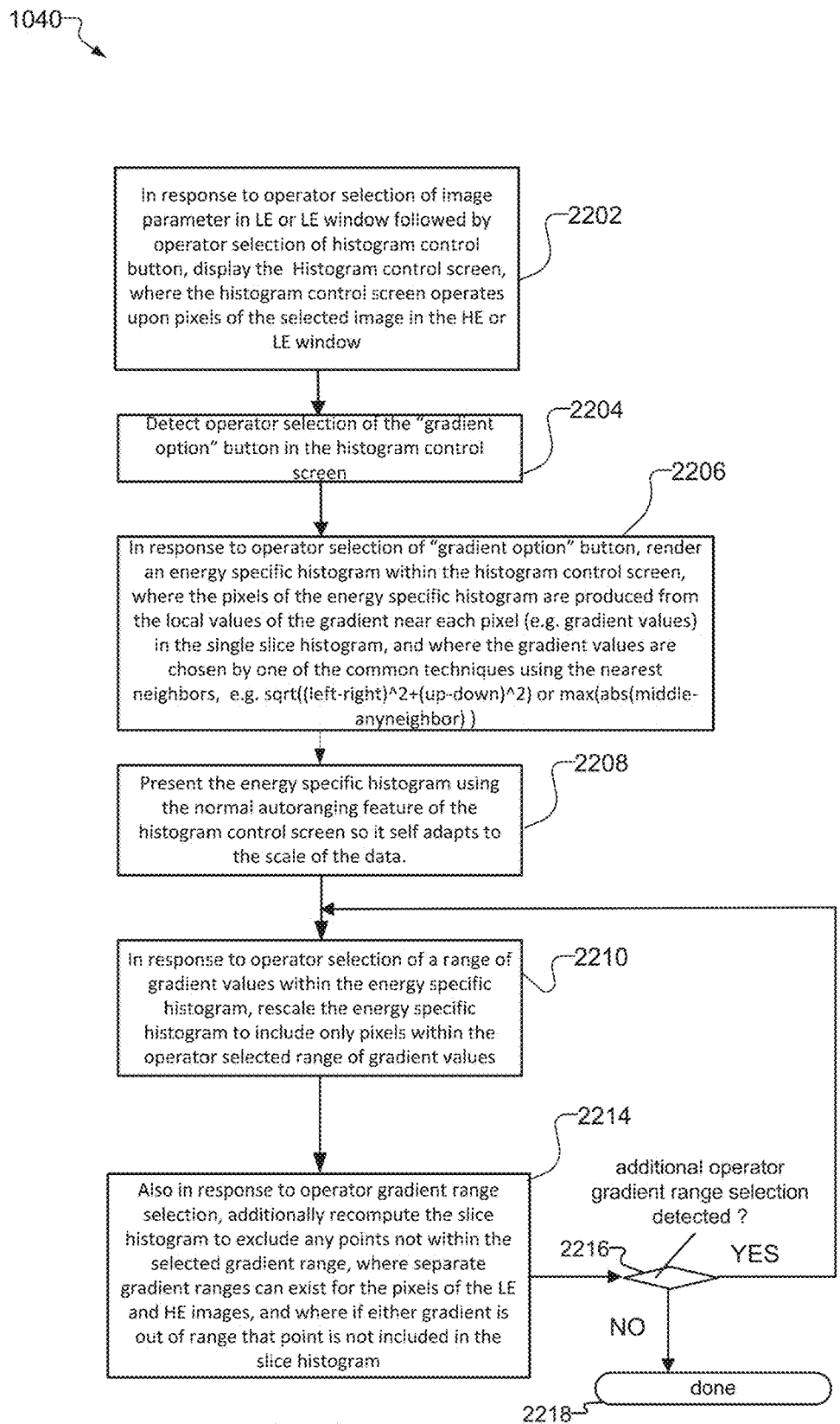
Figure 24A:
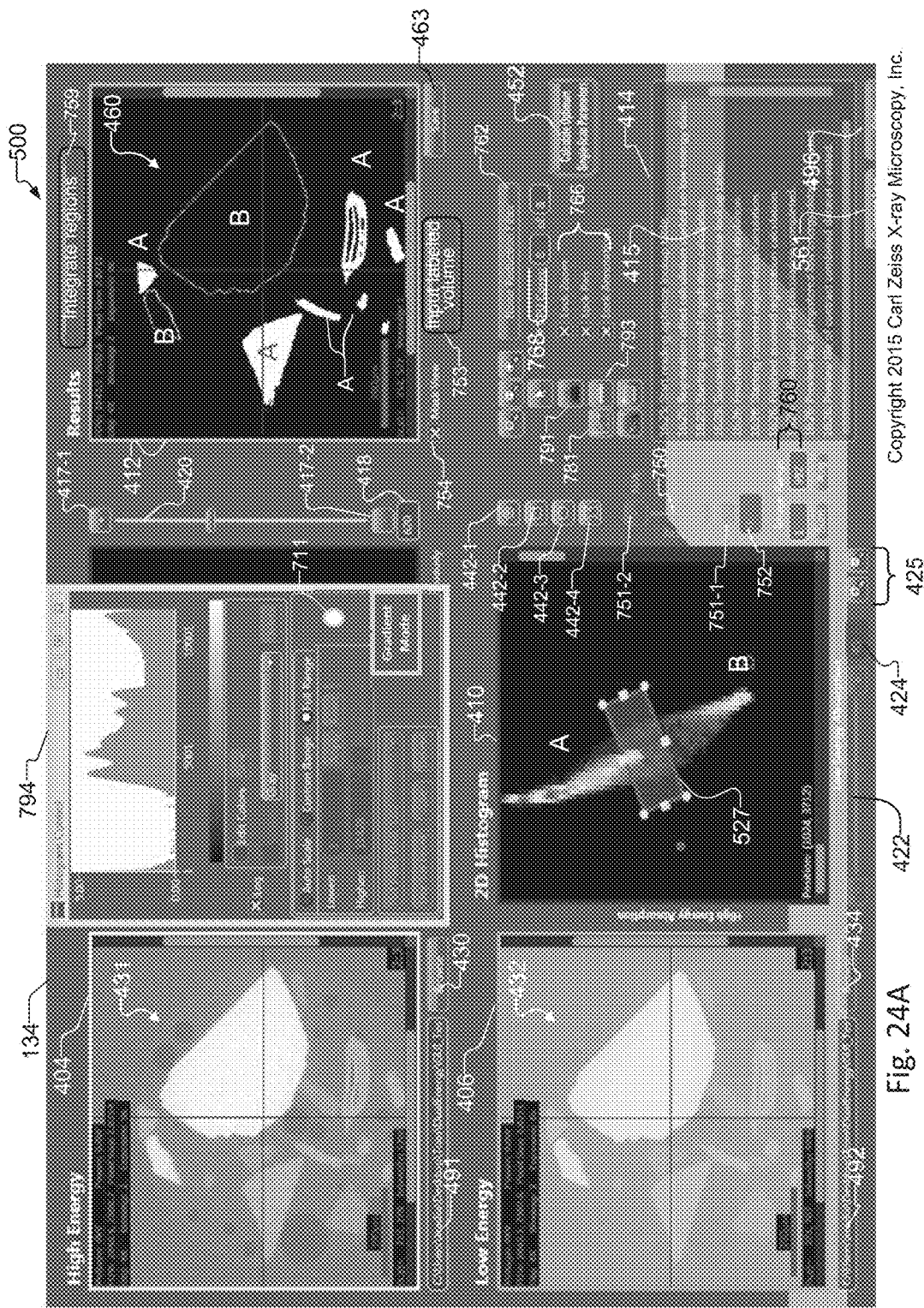
Figure 24B:
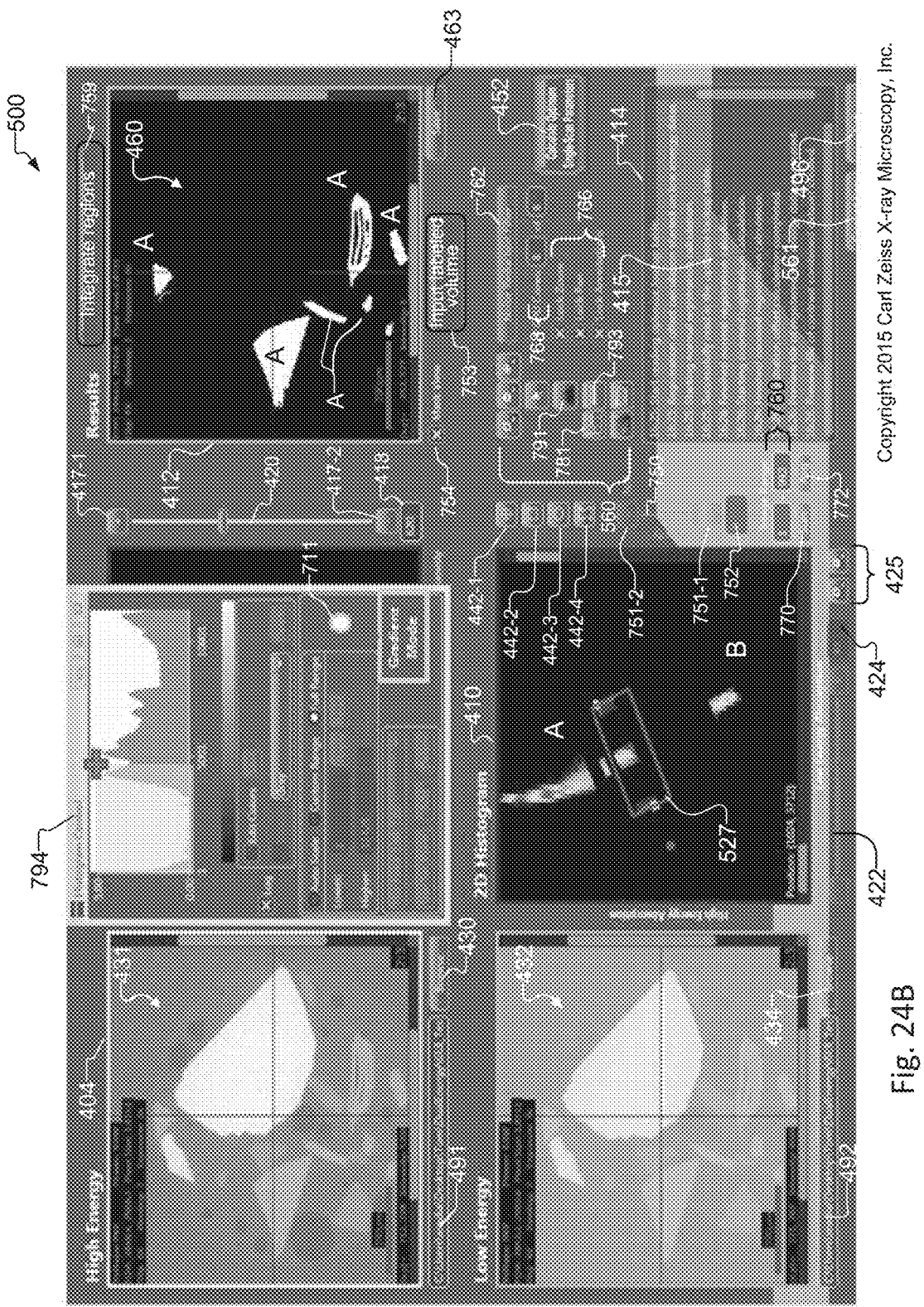
Figure 25:
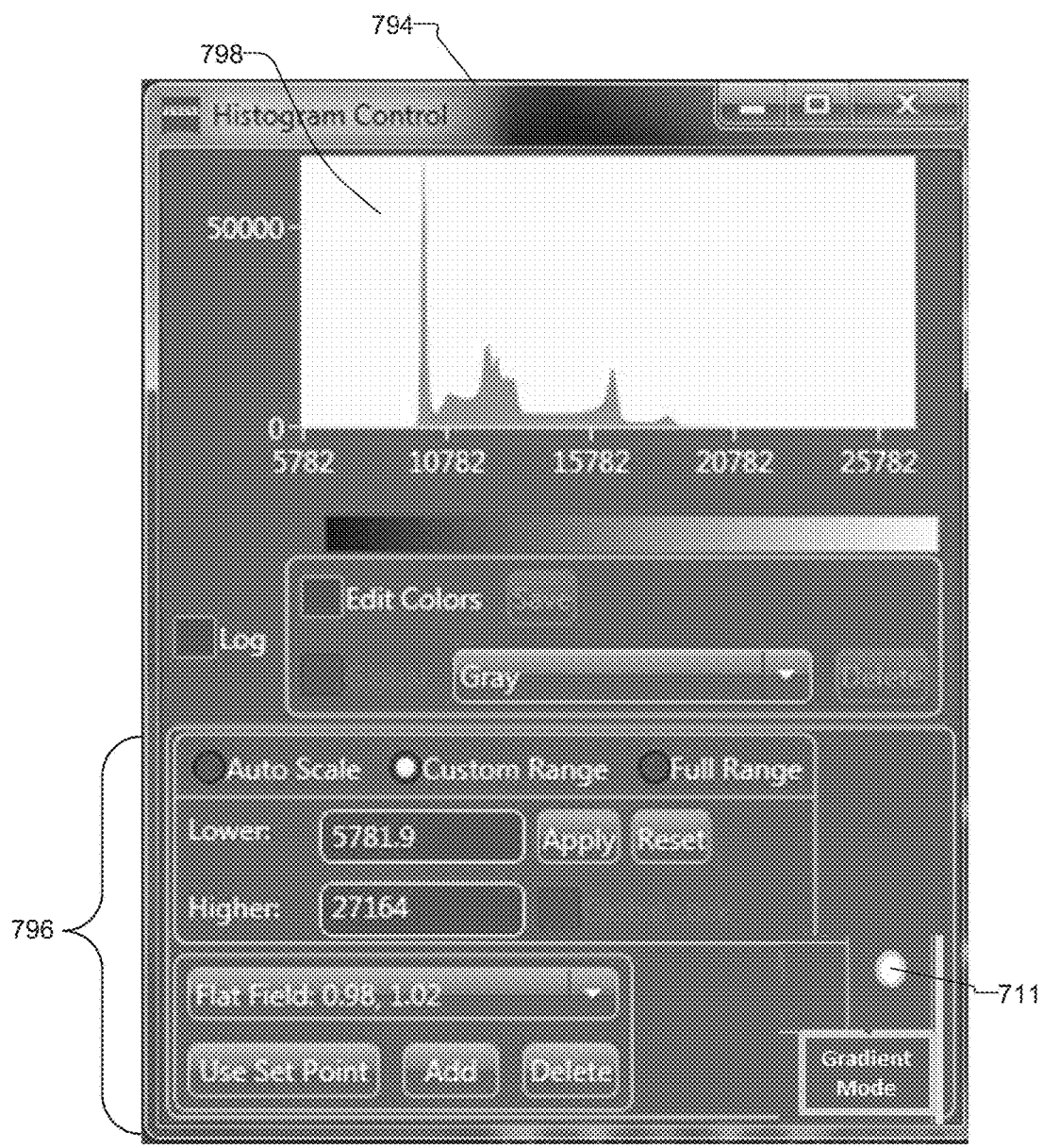
Figure 26:
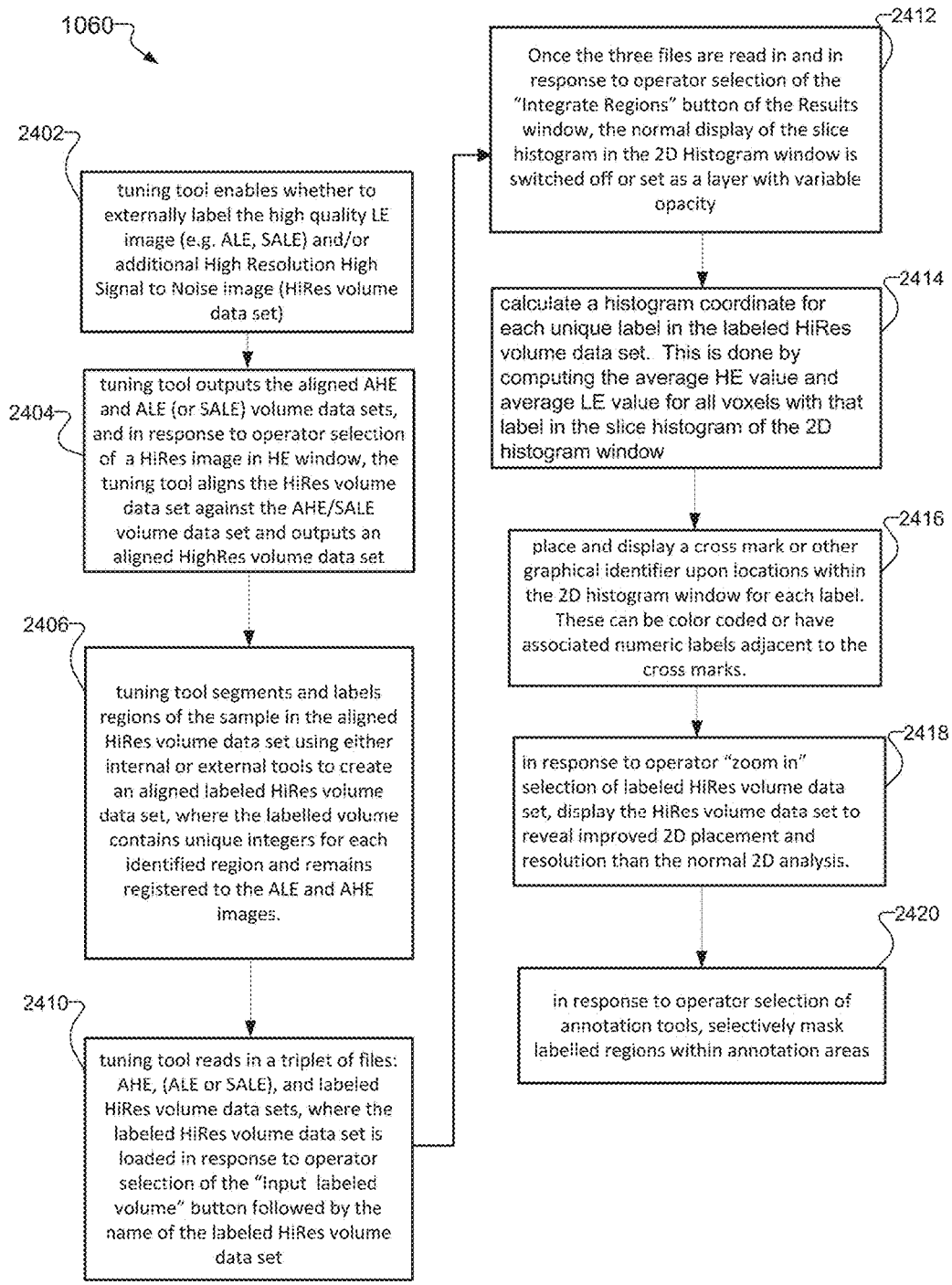
Figure 27A:
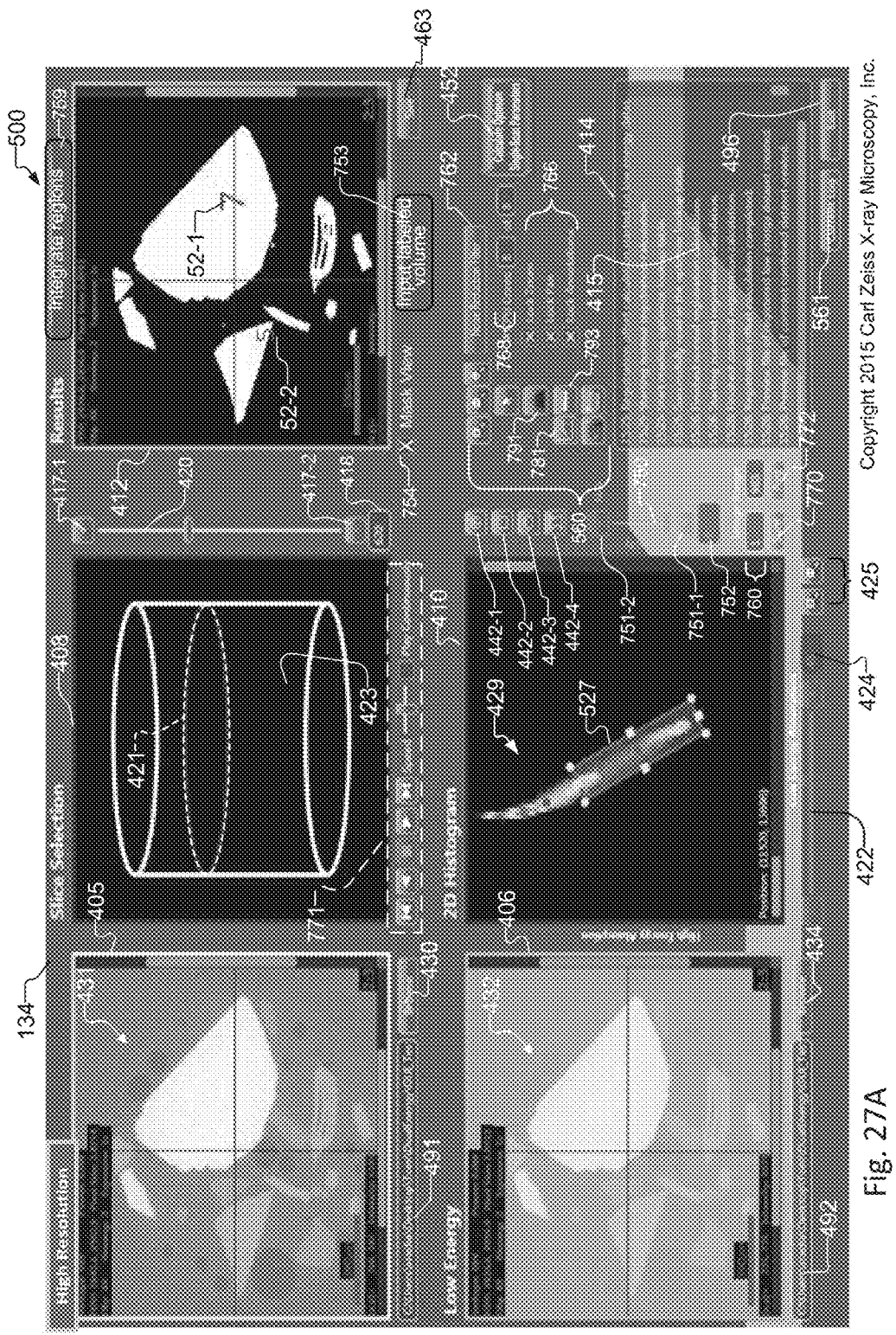
Figure 27B:
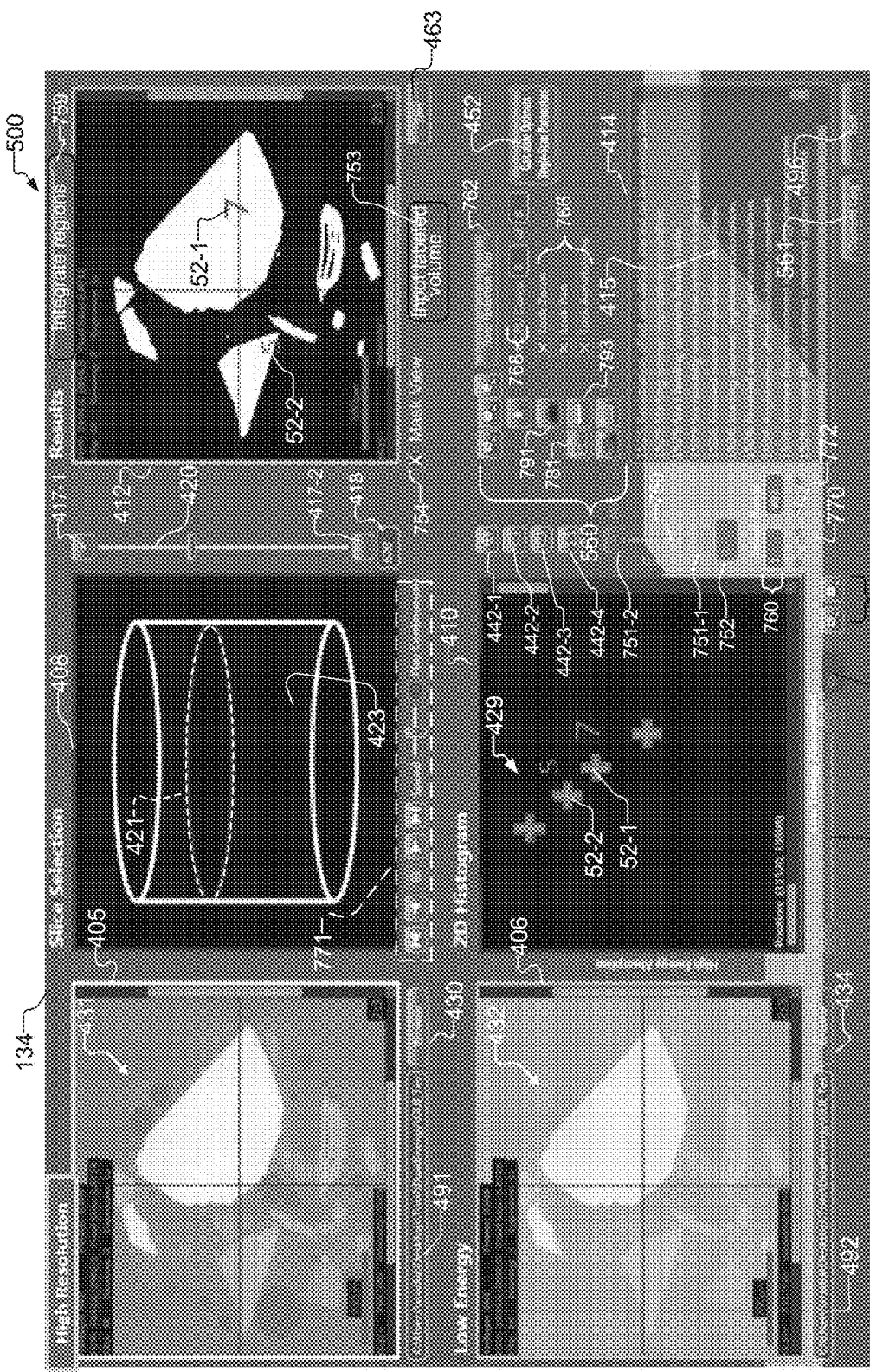

FIG. 6A schematically shows an exemplary histogram of high-energy x-ray absorption versus low-energy x-ray absorption for a sample having two elements, where an operator has selected a single crosshair region of interest within the histogram, and where pixel(s) in the histogram that are included within (i.e. intersect with) the selected region of interest, also known as ROI pixels, are identified for further analysis of the sample;

FIG. 6B also shows the absorption histogram of FIG. 6A, where the operator has instead selected two circular regions of interest within the histogram, and where the pixels included within the selected regions of interest are identified for further analysis of the sample;

FIG. 7A shows the tuning tool as in FIG. 4, where a mask view of the synthetic slice of the sample is displayed within the Results window;

FIG. 7B shows the tuning tool as in FIG. 7A, where a different crosshair region of interest is selected within the histogram than that selected in FIG. 7A, and where the selected region of interest intersects two pixels along a horizontal line within the histogram, causing a new region associated with a different element of the sample to appear within the synthetic mask slice displayed in the Results window;

FIG. 7C shows the tuning tool as in FIG. 4, where instead no regions of interest are selected within the histogram, and where the displayed histogram indicates physical differences in separate elements and not just differences in density of the same element;

FIG. 7D shows the tuning tool as in FIG. 4, where instead a circular or elliptical region of interest is selected within the histogram;

FIG. 7E shows the tuning tool as in FIG. 7D, where instead a different circular or elliptical region of interest is selected within the histogram;

FIG. 8 is a flow diagram showing a method for data acquisition and preprocessing tomographic volume data sets of the sample created by the x-ray imaging system;

FIG. 9 is a flow diagram showing the operation of the user interface of the tuning tool and the processing of the tomographic volume data sets created according to the method of FIG. 8;

FIG. 10 shows the Noise Filter Reduction screen for filtering the LE and HE volume data sets created by the acquisition and preprocessing method of FIG. 8 and/or enhanced LE and HE volume data sets created by the image optimization;

FIG. 11 is a flow diagram that provides more detail for the flow diagram of FIG. 9, where FIG. 11 shows a method for an animation tool that enables historical display of images created by the tuning tool;

FIG. 12 is a flow chart that describes more detail for the flow chart of FIG. 9, for creating an aligned high energy data set (AHE) and a subpixel-aligned low energy dataset (SALE) of the sample as enhanced versions of the original LE and HE volume data sets, where the AHE and SALE volume data sets typically exhibit fewer registration errors as compared to registration errors that occur during alignment of the original LE and HE volume data sets;

FIG. 13 shows the Output Options screen of the tuning tool for creating and saving different volume data sets, such as the AHE and SALE volume data sets, from one or more selected synthetic slices;

FIG. 14A-14B show operation of the subpixel registration method of FIG. 12, where FIG. 14A shows images of the sample when using default "nearest neighbor" registration of the LE and HE volume data sets, showing estimation errors in the histogram and errors in the combined tomographic image, and where FIG. 14B shows improvements to the images of the sample in response to replacing the LE and HE volume data sets utilized in FIG. 14A with AHE and SALE volume data sets of the sample created according to the method of FIG. 12;

FIG. 15 is a flow diagram that provides more detail for the flow diagram of FIG. 9, where FIG. 15 shows a method for generating different statistical versions of histograms (e.g. single/slice, sum, and average) of HE versus LE absorption energies of the sample;

FIG. 16A is a cropped image of the graphical user interface of the tuning tool that shows a magnified view of the 2D Histogram window displaying an Average histogram, which is displayed when an operator specifies an Average histogram in accordance with the method of FIG. 15;

FIG. 16B is a cropped image of the graphical user interface of the tuning tool that shows a magnified view of the 2D Histogram window displaying an overlay image, where the overlay image is created by overlaying the Average histogram for an average slice upon the slice histogram via an Opacity slider;

FIG. 16C is a cropped image of the graphical user interface of the tuning tool that includes a magnified view of the 2D Histogram window displaying a Sum histogram, which is displayed when an operator specifies a Sum slice in accordance with the method of FIG. 15;

FIG. 16D is a cropped image of the graphical user interface of the tuning tool that shows a magnified view of the 2D histogram window displaying an overlay image, where the overlay image is created by overlaying a Sum Histogram for a summed slice upon the slice histogram of a single slice via an Opacity slider;

FIG. 16E displays the same cropped and magnified image of the graphical user interface of the Sum histogram overlay as that displayed in FIG. 16D, where instead different regions of interest are selected within the Sum histogram;

FIG. 17 is a flow diagram that provides more detail for the flow diagram of FIG. 9, where FIG. 17 shows a method for enabling annotations within images displayed within the windows of the tuning tool, and where the method also provides an example of the "pixel mirroring" feature of the present invention;

FIG. 18 shows a graphical user interface of the tuning tool supporting the method of FIG. 17, where the pixels of an annotation created in the Results window are simultaneously highlighted in the images of the HE and LE windows;

FIGS. 19A and 19B are flow charts for methods that further describe the "pixel mirroring" feature, where FIG. 19A shows a method for displaying highlighted versions of pixels within the images of the HE, LE, and Histogram windows in response to operator selection of pixels within the image of the Results window, and where FIG. 19B shows a method for displaying highlighted versions of pixels within the image of the LE window in response to operator indication of pixels within the image of the HE window;

FIG. 20A shows a graphical user interface of the tuning tool that provides another example of the "pixel mirroring" feature;

FIGS. 20B-1 and 20B-2 show cropped and magnified images of the HE window and LE window of the graphical user interface of the tuning tool, respectfully, where the figures provide yet another example of the "pixel mirroring" feature;

FIG. 21 is a flow diagram that provides more detail for the flow diagram of FIG. 9 for creating regions of interest within the histogram(s) of the Histogram window;

FIG. 22A-22C show cropped images of the graphical user interface of the tuning tool that include magnified views of the Histogram window, where rectangular, circular, and polygonal regions of interest, respectively, are selected within an exemplary slice histogram;

FIG. 23 is a flow chart that provides more detail for the flow diagram of FIG. 9 for a gradient suppression method that reduces the effect of unwanted pixels included within the selected regions of interest upon the histograms(s);

FIG. 24A shows an image of the graphical user interface of the tuning tool that includes an exemplary slice histogram including artifacts from edges of elements in the sample, and where the slice histogram includes pixels of energy curves for different elements, and where selection of a region of interest that includes overlapping pixels of the energy curves creates unwanted results in a synthetic slice generated from a selected region of interest within the slice histogram;

FIG. 24B shows an image of the graphical user interface of the tuning tool that illustrates the result of applying the gradient suppression method of FIG. 23 to the slice histogram of FIG. 24A, to remove edge effect artifacts from the slice histogram of FIG. 24A and to remove unwanted results from the synthetic slice generated from operator selected regions of interest within the slice histogram;

FIG. 25 shows a cropped and magnified version of the histogram control window displayed in FIG. 24A and FIG. 24B;

FIG. 26 is a flow chart that provides more detail for the flow diagram of FIG. 9 for a region integration method that assigns labels associated with different elements of the sample to points within the slice histogram, where locations of the points are the average value of slices of the elements in the slice histogram; and FIGS. 27A and 27B show images of the graphical user interface of the tuning tool to illustrate the operation of the region integration method of FIG. 26.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms of the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

FIG. 1 is a schematic diagram of a lens-based x-ray imaging microscope system 100 ("lens-based system").

The lens-based system 100 has an x-ray source system 102 that generates an x-ray beam 103, a filter changer mechanism 106 with a filter wheel 104 for filtering the x-ray beam 103, and a rotation stage 110 with sample holder 112 for holding the sample 114. A condenser 108 placed between the x-ray source system 102 and the sample 114 concentrates and/or focuses the x-ray beam 103 onto the sample 114.

The lens-based system 100 also has a detector system 118, and an objective lens 116 placed between the sample 114 and the detector system 118. When the sample 114 is exposed to the x-ray beam 103, the sample 114 absorbs and transmits x-ray photons associated with the x-ray beam 103. The x-ray photons transmitted through the sample form an attenuated x-ray beam 105, which the objective lens 116 images onto the detector system 118.

The detector system 118 creates an image representation, in pixels, of the x-ray photons from the attenuated x-ray beam 105 that interact with the detector system 118.

FIG. 2 is a schematic diagram of a projection-based x-ray imaging microscope system 200 ("projection-based system") according to another embodiment of the present invention. The projection-based system 200 is similar in structure to the lens-based system 100 and has nearly identical behavior but is typically lower performance in terms of magnification levels.

The projection-based system 200 eliminates the objective lens 116 and possibly the condenser 108 of the lens-based system 100. Otherwise, the projection-based system 200 has the same components as the lens-based system 100, and operators utilize the projection-based system 200 and its components in a similar fashion to the lens-based system 100 for creating x-ray projections and reconstructed tomographic volume data sets of the sample 114.

The projection-based system 200 does not rely on lenses to create a transmission image of the sample 114. Instead it creates a point projection image of the sample 114 by utilizing a small x-ray source spot of the x-ray source 102 projected on the detector system 118. The magnification is achieved by positioning the sample 114 close to the x-ray source 102, in which case the resolution of the projection based system 200 is limited by the spot size of the x-ray source. A magnified projection image of the sample 114 is formed on the detector system 118 with a magnification that is equal to the ratio of the source-to-sample distance 202 and the source-to-detector distance 204. Another way to achieve high resolution in the projection-based system 200 is to employ a very high resolution detector system 118 and to position the sample 114 close to the detector, in which case the resolution of the x-ray image is limited b the resolution of the detector system 114.

For adjusting the magnification of the image, the operator utilizes the user interface applications 124 on the computer system 124 to adjust the source-to-sample distance 202 and the source-to-detector distance 204. The operator adjusts these distances, and achieves the desired magnification, by moving the rotation stage 100 via the controller 122. The x-ray detector system 118 also provides the ability to adjust the field of view on the sample by changing the pixel size within the x-ray detector system 118, according to some implementations.

The computer system 124 of systems 100, 200 also has an image processor 120, a controller 122 such as a central processing unit and, and user interface applications 126 that execute on the controller 122 and/or the image processor 120. A display device 136 connected to the computer system 124 displays information and graphical user interfaces from the user interface applications 126. The computer system 124 further loads information from, and saves information to, a database or other datastore 150 connected to the computer system 124. The controller 122 has a controller interface 130 that allows an operator to control and manage components in the systems 100, 200 under software control via the computer system 124.

Operators utilize the user interface applications 126 that execute on the controller 122 and/or the image processor 124 to configure and manage components in the systems 100, 200 via the controller 122. User interface applications 126 include a scout and scan application 132 and a multi energy (DE) image parameter tuning tool 134, also known as the tuning tool. The controller 122 controls components that have a controller interface 130. Components that have a controller interface 130 include the image processor 120, the detector system 118, the rotation stage 110, the x-ray source system 102, and the filter changer mechanism 106, in one implementation.

The dual energy templates 133 provide the settings between the low-energy and high-energy scans required by the image optimization method 900 of FIG. 9, for example, while allowing the operator to choose scanning parameters and other settings specific to the low-energy and high-energy scans. In other examples, the templates provide the settings for the capture of volumes under other sets of conditions such as volumes captured with absorption versus phase contrast imaging, with a dry versus wet sample, or volumes captured for a sample with and without contrast agent or with different contrast agents.

Via the user interface applications 126, operators can create tomographic volume data sets of the sample, and then execute image optimization operations upon the tomographic volume data sets to reveal information concerning elemental features of the sample. The tomographic volume data sets are created according to the preprocessing method of the sample described in FIG. 9, and the image optimization operations executed upon the tomographic volume data sets are described according to the image optimization method of FIG. 10.

For selection of scanning parameters, the operator typically uses the scout and scan application 132 to configure an x-ray voltage setting and exposure time on the x-ray source system 102, and a filter setting of the filter wheel 104 of the filter changer mechanism 106. The operator also selects other settings such as imaging geometry (distances between source and sample and between the sample and the detector), the field of view of the x-ray beam 103 incident upon the sample 114, the number of x-ray projection images to create for the sample 114, and the angles to rotate the rotation stage 110 for rotating the sample 114 in the x-ray beam 103, for example.

In the multi-energy x-ray imaging of the sample 114, the operator performs at least a low-energy scan and a high-energy scan of the sample 114. The operator chooses scanning parameters associated with known x-ray absorption coefficients for compounds in the sample 114 for the low-energy and high-energy scans.

Operators utilize a number of techniques to generate the multi-energy, such as high and low energy x-ray beams, for the two scans. In one example, the x-ray source system 102 generates the low-energy x-ray beam using a low energy x-ray source and generates the high-energy x-ray beam using a high energy x-ray source. In another example, the x-ray source system generates the low-energy x-ray beam using a low energy setting for an x-ray source and generates the high-energy x-ray beam using a high energy setting of the x-ray source system. In other examples the filters are used so that the x-ray source system generates the low-energy x-ray beam using a low energy filter for an x-ray source and generates the high-energy x-ray beam using a high energy filter of the x-ray source. In still a further example, different x-ray source anode targets are used so that the x-ray source system generates the low-energy x-ray beam using a low energy anode target for an x-ray source and generates the high-energy x-ray beam using a high energy anode target of the x-ray source. The x-ray source system can generate the low-energy x-ray beam using a low energy exposure time for an x-ray source and generate the high-energy x-ray beam using a high energy exposure of the x-ray source. In general, the low-energy exposure times and high-energy exposure times are different from each other and are chosen to produce datasets with sufficient signal-to-noise ratio. Additionally, the multiple energy scans can even occur simultaneously, using multiple detectors with different energy filters.

Some settings, such as the scanning parameters and the number of projections for each scan, can vary between the low-energy and high-energy scans. Certain settings, however, such as the field of view and the start and end angles, should be identical or at least overlapping for the low-energy and high-energy scans. These settings are helpful for subsequent alignment and registration of the low-energy and high energy reconstructed tomographic data sets created by their respective scans. This is an important for the image optimization method of FIG. 10, discussed in the detailed description associated with FIG. 9 appearing later in this document.

The scout and scan application 132 has one or more dual energy templates 133. The scout and scan application 132 provides different dual energy templates 133 depending on the types of the sample 114. The dual energy templates 133 provide the same settings between the low-energy and high-energy scans required by the image optimization method 900 of FIG. 9, while allowing the operator to choose scanning parameters and other settings specific to the low-energy and high-energy scans.

Using the dual energy templates 133, the operator defines the same field of view and the same start and end angles for the low-energy and high-energy scans. The operator then defines the scanning parameters associated with the low-energy and high-energy scans, and defines other settings that can vary between the scans, such as the number of projections. The dual energy templates 133 then provide the configuration to perform the low-energy and high-energy scans of the sample 114.

During a scan, the image processor 120 receives and processes each projection from the detector system 118, in one example, although the controller 122 could process the projections in other examples. The scout and scan application 132 saves the projections from the image processor 120 to later generate a reconstructed tomographic volume data set of the sample 114. The computer system 124 saves the tomographic data sets from each scan, and their associated scanning parameters and settings, to local storage on the computer system 124, or to the database or datastore 150. The computer system saves a low-energy tomographic volume data set 152 for the low-energy scan, and a high-energy (HE) tomographic volume data set 154 for the high-energy scan, to local storage or to the database 150 after their calculation. The computer system also includes a noise reduction filter 161.

The operator uses the tuning tool 134 for optimizing image display parameters such as the image contrast of the images that are generated of the sample 114, in one example. Using the tuning tool 134, the operator loads the LE tomographic volume data set 152 and HE tomographic volume data set 154. The operator then often selects a slice within the datasets, and selects information for optimizing the image display parameters, such as image contrast, of the selected slice. The optimized selected slice is also known as a synthetic slice, or a synthetic mask slice if a "mask view" of the image processing result is selected by the user. The operator then applies this information to optimize the image display parameters and create a combined or synthetic volume data set 156. Metadata such as the slice number 408 for each selected slice 431, 432, names of the LE and HE volume datasets 152, 154 from which the slices 431, 432 are selected, and names of histograms 429 and synthetic slices 460 generated from each selected slice 431, 432 are saved to a slice selection history log 159 within the database 150.

The operator can execute additional image processing operations upon the LE and HE volume data sets 152, 154 prior to and during creation of the synthetic slice/synthetic mask slice to improve the imaging parameters of the combined or synthetic volume data set 156. Prior to creation of the synthetic slice, in one example, the operator can execute filtering operations upon the LE volume data set 152 and the HE volume data set 154 to reduce noise in the images (e.g. improve the signal to noise ratio in the images 152, 154) prior to creating the combined volume data set 156. This is described in more detail in steps 930 through 934 of the image optimization method of FIG. 9. In another example, the operator can improve alignment between the voxels of the volume data sets 152, 154 by creating new "subpixel aligned" versions of the LE and HE volume data sets 152, 154 prior to registering the voxels of the volume data sets 152, 154 with each other and in magnification. This process is also known as subpixel registration of the LE and HE volume data sets 152, 154 and is described in more detail in step 960 of the image optimization method of FIG. 9 and in the method of FIG. 12.

Additional image processing operations during creation of the synthetic slice also provide the ability to improve the image contrast of the combined volume data set 156 created from the synthetic slice. In one example, statistically enhanced histograms (e.g. Sum and Average histograms) can reveal different distribution information about trace elements and volumetric structures within the sample 114 than that provided by the standard or single slice histogram of LE versus HE absorption values. This is described in more detail in step 990 of the image optimization method of FIG. 9 and in the method of FIG. 15. In another example, operators can select multiple regions of interest within the histograms during creation of the synthetic slice, where the regions of interest include and/or intersect multiple pixels within the histograms. This is described in more detail in step 1010 of the image optimization method of FIG. 9 and in the method of FIG. 21. In yet another example, an operator can suppress errors associated with edge pixels of elements in the histograms via the gradient suppression method of step 1040 within the method of FIG. 9 and in the method of FIG. 23. In still yet another example, an operator can use the region integration method of step 1060 within the method of FIG. 9 and described in the method of FIG. 26 to annotate the histogram and the image of the combined volume data set 156 displayed in the tuning tool 134 with visual labels associated with elemental composition of the sample.

Because the combined volume data set 156 contains slices with optimized image contrast, the combined volume data set 156 is also referred to as an optimized combined volume data set. Once the operator has created the combined volume data set 156, the operator optionally uses the tuning tool 134 to calculate optimum single-scan parameters 158 from the scanning parameters associated with the creation of the combined volume data set 156. This is especially useful if the operator intends to perform runs against several samples to produce the same approximate imaging parameter results. In this way, the operator can apply the optimum single-scan parameters 158 to the imaging system 100, 200 to perform a subsequent single-energy scan of the same sample 114, or of a new sample with similar elemental composition.

The calculation of optimal single-scan parameters is discussed in more detail in the detailed description associated with method 1010 of FIG. 9 and FIG. 21, appearing later in this document.

Figure 3:
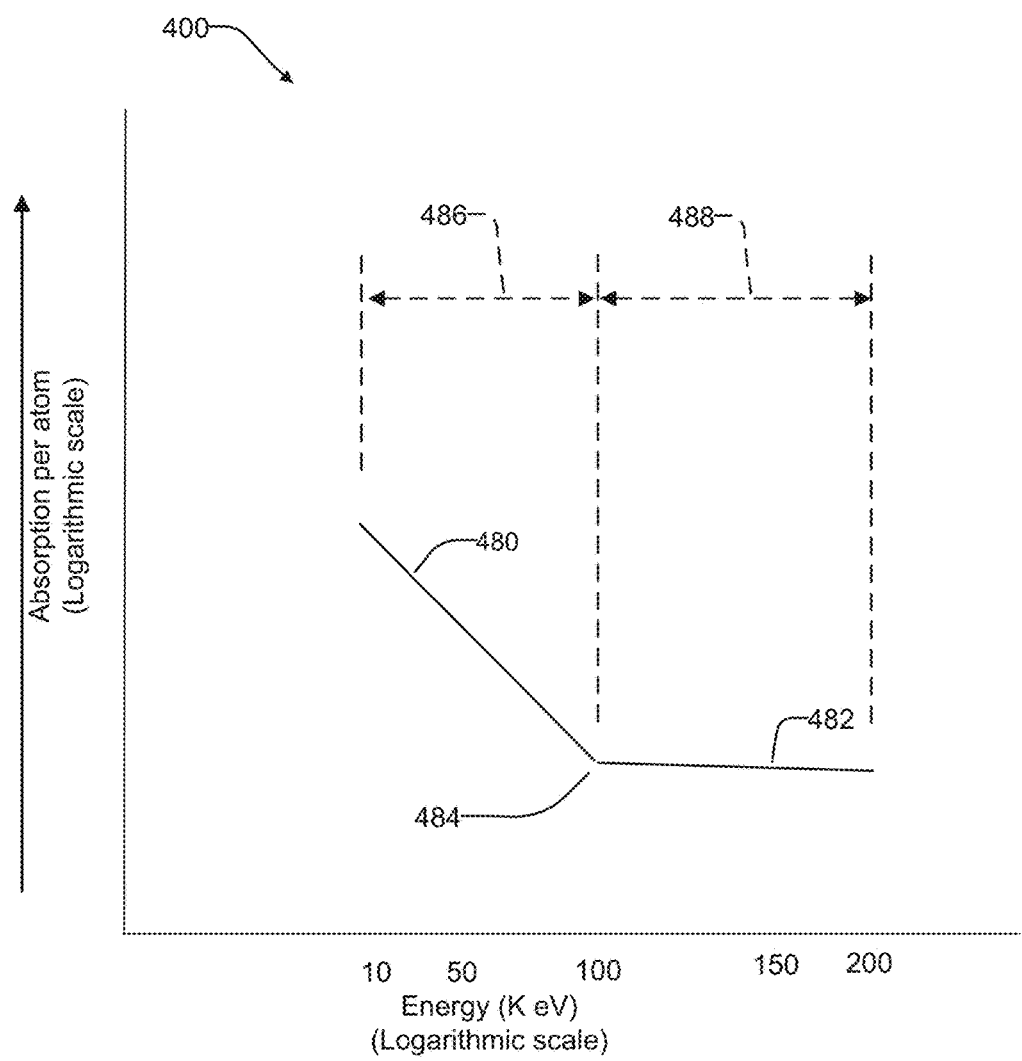
FIG. 3 is a typical x-ray absorption versus x-ray energy curve for low-Z elements such as Calcium (Z=20) that provides a rationale for utilizing dual-energy x-ray imaging of a sample to optimize imaging parameters and isolate properties within the sample.

FIG. 3 is a typical x-ray absorption versus x-ray energy plot 400 ("absorption plot") for low-Z elements such as Calcium (Z=20) that provides a rationale for utilizing dual-energy x-ray imaging of a sample to isolate properties within the sample. Both axes are plotted using a logarithmic scale. Dual-energy x-ray imaging of a sample utilizes the crossover in absorption and scattering behavior when a sample 114 is irradiated with low-energy and high-energy x-rays.

Low-Z elements typically include Hydrogen (H=1) to Iron (Fe=26), and high-Z elements are elements whose atomic numbers are larger than Iron. With respect to dual-energy x-ray imaging, low-Z elements have different absorption plots 400 than high-Z elements.

The absorption plots 400 of low-Z elements have a LE absorption section 480 and a HE absorption section 482, separated by a knee or inflection point 484. The LE absorption section 480 is associated with applied x-ray energy in the LE scan range 486, and the HE absorption section 482 is associated with applied x-ray energy in the HE scan range 488.

For a given x-ray energy and element with atomic number Z, the LE absorption section 480 scales inversely with $Z^4$ over the LE scan range 486, and the HE absorption section 482 scales inversely linearly with Z over the HE scan range 488. The x-ray absorption in the LE absorption section 480 is typically attributable to absorption associated with the photoelectric effect, whereas the x-ray absorption in the HE absorption section 482 is typically attributable to Compton scattering.

For all Z, the x-ray energy associated with the knee 484 of their absorption plots 400 increases with increasing Z. The absorption plots 400 for high-Z elements have a less-discernible knee compared to that of low-Z elements. Their LE scan ranges 486 and HE scan ranges 488 increase with increasing Z, and K-edge absorption transitions become more of a factor. However, the DE x-ray imaging techniques also apply to high-Z elements, such as Gold and Iodine, by using scanning parameters and filters specific to each element that limit or utilize the effect of K-edges in their absorption plots 400.

FIG. 4 illustrates the graphical user interface 500 of the tuning tool 134 that would be displayed on the display device 136, for example. The tuning tool 134 has a high energy window 404 for selection and display of a slice from a high-energy tomographic volume data set 154 of a sample, and a low energy window 406 for selection and display of a slice from a low-energy tomographic volume data set 152 of the same sample. The high-energy tomographic volume data set 154 and the low-energy tomographic volume data set 152 were generated using the x-ray imaging systems in FIG. 1 and FIG. 2 and in accordance with the image preprocessing method of FIG. 8, the description of which appears later in this document.

In other examples, window 404 displays a slice from a tomographic volume data set that was collected under a different set of conditions than the slice displayed in window 406 and its corresponding volume data set. For example, in another example, the first tomographic volume data set 154 was collected with absorption contrast, from dry sample or from a sample with no contrast agent. On the other hand, second tomographic volume data set 152 was collected with phase contrast, from a wet sample, or from a sample with contrast agent, respectively.

The high energy (HE) window 404 has a high energy tomographic volume data set selector 430, and the low energy (LE) window 406 has a low energy tomographic volume data set selector 434. The operator uses the high energy tomographic volume data set selector 430 to open a file browser dialog for selection of a HE tomographic volume data set 154 on the computer system 124 or on the database 150. The operator uses the low energy tomographic volume data set selector 434 to open a file browser dialog for selection of a low energy tomographic volume data set 152 on the computer system 124 or on the database 150.

The tuning tool 134 also has a slice selection window 408, a 2-D histogram window 410, a results window 412 that displays a synthetic or optimized slice image 460, and a log window 414. The results window provides spatial image analysis of the sample 114. The slice selection window 408 has an interactive graphic 423 for enabling an operator to select a slice from the low energy tomographic volume data set 152 and the HE tomographic volume data set 154. The interactive graphic 423 has a slice selection display 421. In examples, the slice selection display 421 is a graphic such as an ellipse or an animated image associated with the selected slice. The slice selection window 408 has a slice selector slider bar 420, a slice number indicator 418, and an animation tool 771.

The 2-D histogram window 410 includes a histogram 429. The histogram 429 shows voxel or pixel intensities resulting from the plot of the pixel intensities for the LE slice 431 versus the pixel intensities of the HE slice 432, in accordance with the plot of FIG. 3. The 2D. Histogram window 410 provides statistical analysis of the sample 114. An operator uses the 2-D histogram window 410 to interactively determine the mixing parameters of the LE slice 432 and HE slice 431. The tuning tool 134 generates a slice histogram 429 from the HE and LE volume datasets 154, 152 in response to operator selection of the histogram button 781.

By default, the histogram 429 generated in response to selection of the histogram button 781 is a "single" or slice histogram associated with the single slice selected in the slice selection window 408. Alternate statistical versions of the histograms can be created from the slice histogram 429. In one example, an "Average Histogram" is created in response to operator selection of the "Avg" button 772, where each point within the average histogram is the averaged value of the points in the single or slice histogram across a specified range of slices. In another example, a "Sum Histogram" is created in response to operator selection of the "Sum" button 770, where each point within the sum histogram is the sum of the values of the points in the single histogram across a specified range of slices. More details concerning the creation of the average histogram and the sum histogram are included in the description that accompanies the methods of FIG. 9 and FIG. 15, which appear later in this document.

The operator interactively determines the mixing parameters of the LE slice 432 and HE slice 431 by selecting a region of interest 527 within the histogram 429. In one example, the region of interest (ROI) 527 is a pivot point 427 and angle within the 2-D histogram 429. The operator uses ROI selectors 442 to select different region of interest 527 types. Each region of interest 527 includes and/or intersects at least one pixel within the histogram 429. The ROI selectors 442 include a crosshair ROI selector 442-1 for enabling the user to select a pivot point 427 and angle within the histogram 429, a rectangle ROI selector 442-2 for enabling the user to draw a rectangle upon the histogram 429, a circle ROI selector 442-3 for enabling a user to draw a circle upon the histogram 429, and a polygon ROI selector 442-4 for enabling a user to draw a polygon shape upon the histogram 429. The pixels that intersect and/or are included within the one or more regions of interest 527 drawn upon the histogram are also known as ROI pixels. More details concerning the creation of the regions of interest 527 are included in the description that accompanies the method of FIG. 9 and FIG. 18, which appear later in this document.

In response to the selection of the exemplary pivot point 427 region of interest 527 and angle 424, the computer system 124 draws or renders the line 714 through the pivot point 427 at the specified angle within the 2-D histogram 429.

In general, the pivot point 427 does not affect the ratio of the low-energy and high-energy scans, but just the scaling of the output composite or synthetic slice. The slope of the line in the 2-D histogram 429 determines the mixing ratio of LE and HE slices (i.e. the coefficients that are used to combine the LE and HE data). The pivot point 427 determines an offset value. I.e.: synthetic intensity value=x*LE value+(1− x)*HE value+offset. Slope determines x and the pivot point determines offset.

The operator chooses the angle via an angle selector slider bar 422, and an angle number indicator 424 reflects the value of the angle selected in degrees. The pivot point 427 is selected by clicking on a point within the 2D histogram. The shown brightness or intensity and/or color in the 2-D histogram 429 is a measure of the number of voxels in the slice with given pixel intensity of the LE slice 432 versus HE slice 431 pixel intensities. The 2-D histogram intensity is displayed with user selectable color maps that determine the colors representing different intensities.

The 2-D histogram densities are scaled logarithmically to make sure even single pixels can be seen as points on the 2-D histogram 429 to ensure that data that corresponds to small features on the slice is still visible. The operator uses the distribution of pixels on the 2-D histogram as a starting guide to select the pivot and angle of the line 714. The results window 412 displays a synthetic slice 460 computed through settings of the line 714 in the 2-D histogram window 410. The results window also includes a mask view selector 754 for displaying a mask view of the synthetic slice 460.

In other examples, the volume datasets correspond to different states of the sample. For example, the sample 114 might be scanned to generate one volume dataset and the sample 114 is then immersed in water or other wetting solution. The sample 114 is then rescanned using the same parameters when wet. In this case, the histogram 429 will indicate the regions which were once dry and then wet, those regions that did not change will be on a straight line through the 2D histogram 429, and regions that changed will not appear on this same line. The pivot point and/or ROI tools are then used to visualize and/or create a mask image of the regions that underwent changes in the dry/wet transition.

The log window 414 displays log information 415 associated with the operations of the tuning tool 134. The log window 414 also has a log button 561 for enabling the display of log information 415 in the log window 414. The tuning tool 134 also has an exit button 496 for exiting the tuning tool 134.

Located between the Results window 412 and the Log window 414 are a number of controls for manipulating image parameters created by the tuning tool 134. An annotation palette 560 enables statistical operations, and zooming in/out of a selected window, in examples. User selection of the histogram button 781 causes the tool to create a slice histogram 429 from the HE and LE volume datasets 154, 152. A histogram control button 791 invokes the histogram control screen 794 for controlling aspects of an associated histogram 429. A noise reduction filter selector 762 enables filtering of the HE and LE volume data sets 154,152 by directing the tuning tool 134 to pass the HE and LE volume data sets 154, 152 through the noise reduction filter 161 in response to operator selection of the noise reduction filter selector 762. Zoom control 766 provides the ability to control zoom functions upon the synthetic slice 460. CPU core selector 768 provides the ability to select a range of CPU cores for sharing image processing tasks associated with the creation and optimization of the synthetic slice 460 and the combined tomographic volume dataset 156 generated from the synthetic slice 460. Annotation button 793 enables the creation of annotations within the images displayed within the windows of the tuning tool.

A number of selectors or buttons are specific to operations associated with images within the results window 412. The integrate regions button 759 and input labeled volume buttons 753 are used in conjunction with the region integration function of FIG. 9 step 1060 and FIG. 26. The mask view 754 checkbox, when selected, enables calculation and display of a mask view of the synthetic slice 460.

Once the operator has selected the high energy, or first, tomographic volume data set 154 and the low-energy, or second, tomographic volume data set 152, the computer system 124 auto-aligns, registers, and scales the high energy tomographic volume data set 154 and the low-energy tomographic volume data set 152 with each other, and in magnification, in response to the selections.

The operator then uses the slice selection window 408 to select a slice within the HE tomographic volume data set 154 and the LE tomographic volume data set 152. Using the slice selector slider bar 420, with the aid of the interactive graphic 423, the operator selects a slice, and the slice selection display 421 of the interactive graphic provides a visual indicator of the selected slice relative to the total number of slices available. The slice number indicator 418 also displays the slice number of the selected slice.

The selected slice is an abstraction or device used by the tuning tool 134 to enable the user to select a common slice within the high energy tomographic volume data set 154 and the low-energy tomographic volume data set 152. The computer system 124 uses the information associated with the user selected slice to compute the 2-D histogram 429 of high-energy pixel intensity versus low-energy pixel intensity values for the selected slice. The points displayed on the 2-D histogram 429 form visually-distinct clusters of pixel densities associated with elements in the sample for the selected slice. Then, in one example, the operator selects a pivot point 427 region of interest 527 and angle within the histogram 429, and the computer system 124 computes the synthetic slice image 460 using the information associated with the point 427 and angle 424 selections. This is discussed in more detail in the description that accompanies FIG. 9, appearing later in this document.

When the operator has selected a slice in the slice selection window 408, the high energy window 404 displays a high-energy ("HE") slice 431 from the high-energy tomographic volume data set 154 associated with the slice selection, and the low energy window 406 displays a low-energy ("LE") slice 432 of the low-energy tomographic volume data set 152 associated with the slice selection. After the slice is selected, the operator can select the histogram button 781. In response, the computer system 124 creates the histogram 429, and the 2-D histogram window 410 displays the histogram 429.

The 2-D histogram window 410 has an angle selection slider bar 422, and an angle number indicator 424. When the 2-D histogram window 410 displays the histogram 429, the operator selects a region of interest 527, such as a pivot point 427 within the histogram 429 for image contrast optimization of the selected slice. In the example, the operator selects the crosshair ROI selector 442-1 for creating the pivot point 427 region of interest 527. When the operator has selected the pivot point 427 region of interest 527, the angle selection slider bar 422 becomes operable. Using the angle selection slider bar 422, the operator selects an angle within the histogram 429, and the angle number indicator 424 displays the angle, in degrees, in response to the angle selection. Angle selector buttons 428-2 and 428-1 additionally provide the ability to increment and decrement the angle, respectively, for finer control over the angle than that provided b e angle selection slider bar 422.

For the exemplary pivot point 427 region of interest 527, the computer system 124 draws a ratio calculation line 714 through the operator-selected point of interest 427 and angle in the histogram 429. The ratio calculation line 714 is a visual aid to the operator to display the ratio between the high-energy pixel intensity versus the low-energy pixel intensity information that the computer system 124 will use from the 2-D histogram 429 when optimizing the selected slice. The results window 412 displays the synthetic slice 460 that the computer system 124 calculates in response to the operator-selected point of interest 427 and angle in the 2-D histogram 429.

In a continuous fashion, whenever the operator selects a different slice in the slice selection window 408, the high energy window 404 updates the display of the high-energy slice 431, and the low energy window 406 updates the display of the low-energy slice 432, in response to the slice selection. In a similar fashion, in response to operator selection of the histogram button 781, the computer system 124 computes a new histogram 429 for the selected slice, and the 2-D histogram window 410 displays the 2-D histogram 429, and the results window 412 displays a synthetic slice 460 in response to the operator-selected point of interest 427 and angle in the 2-D histogram 429.

The synthetic slice 460 is an image parameter-optimized slice. Often the image contrast or false applied colors are optimized to enable visual discrimination of elements of interest from uninteresting elements. Once the operator is satisfied with the synthetic slice 460, the operator selects the save button 463 of the results window 412 to apply the image contrast information associated with the synthetic slice 460 to all slices in the high energy tomographic volume data set 154 and the low-energy tomographic volume data set 152. This creates a new, combined tomographic volume data set. Because the combined volume data set is generated using contrast information associated with the synthetic slice 460, the combined volume data set is also known as an optimized combined tomographic volume data set 156. The computer system 124 saves the optimized combined tomographic volume data set 156 to local storage, or to the database 150.

Figure 5A:
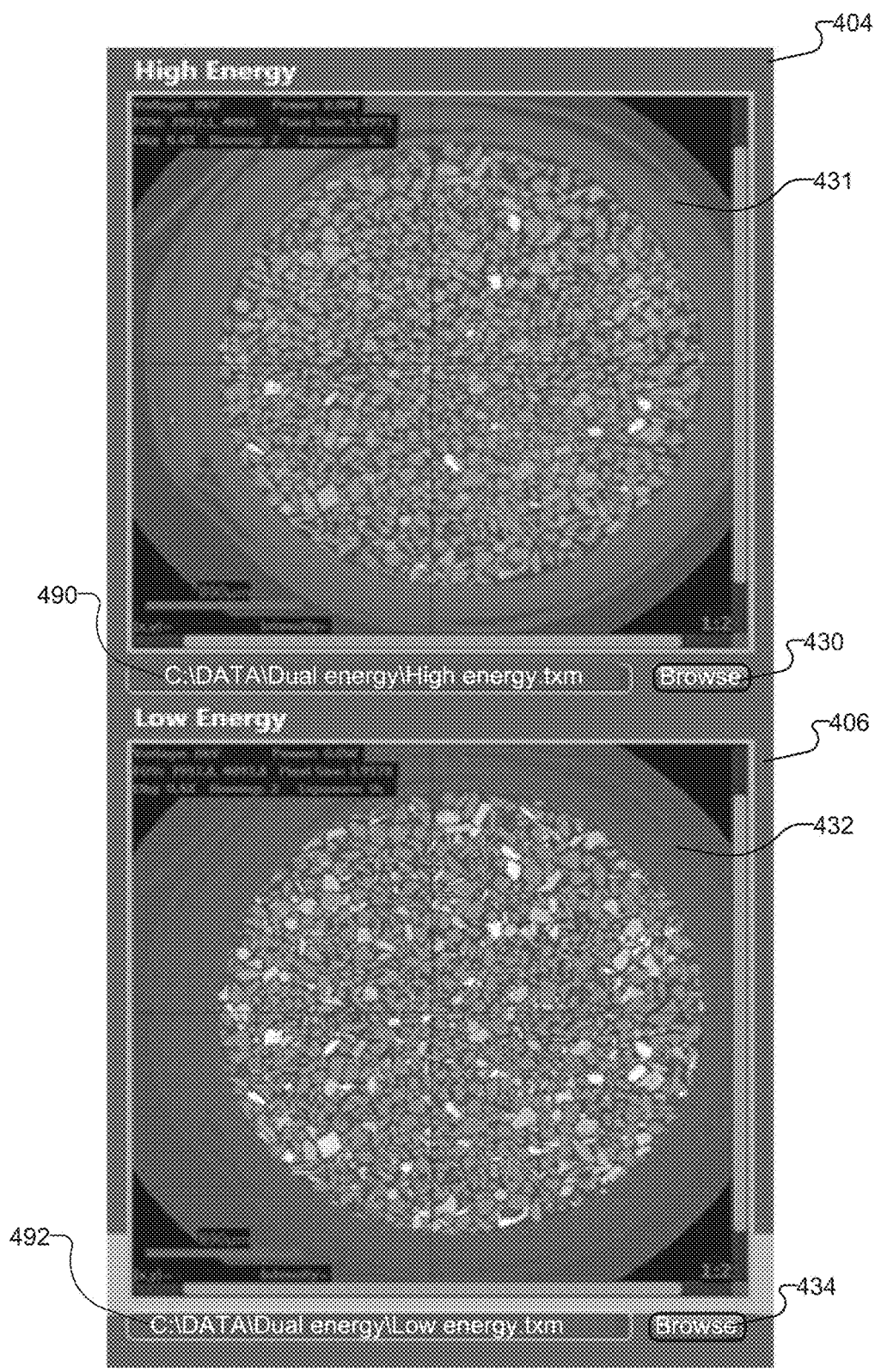
FIG. 5A shows a cropped image of the graphical user interface of the tuning tool of FIG. 4 that includes a magnified view of Slice Selection and 2D Histogram windows for displaying more detail associated with the windows.

FIG. 5A is a cropped and magnified view of the LE window 406 and LE window 404 of the DE tuning tool 134 in FIG. 4. The high energy window 404 also has a high energy filename indicator 490 that displays the filename associated with the selected high energy tomographic volume data set 154. The high energy window 404 also displays high-energy scanning parameters 502 overlaid upon the high energy slice 431.

The low energy window 406 also has a low energy filename indicator 492 that displays the filename associated with the selected low energy tomographic volume data set 152. The low energy window 406 also displays high-energy scanning parameters 504 overlaid upon the low energy slice 432.

Figure 5B:
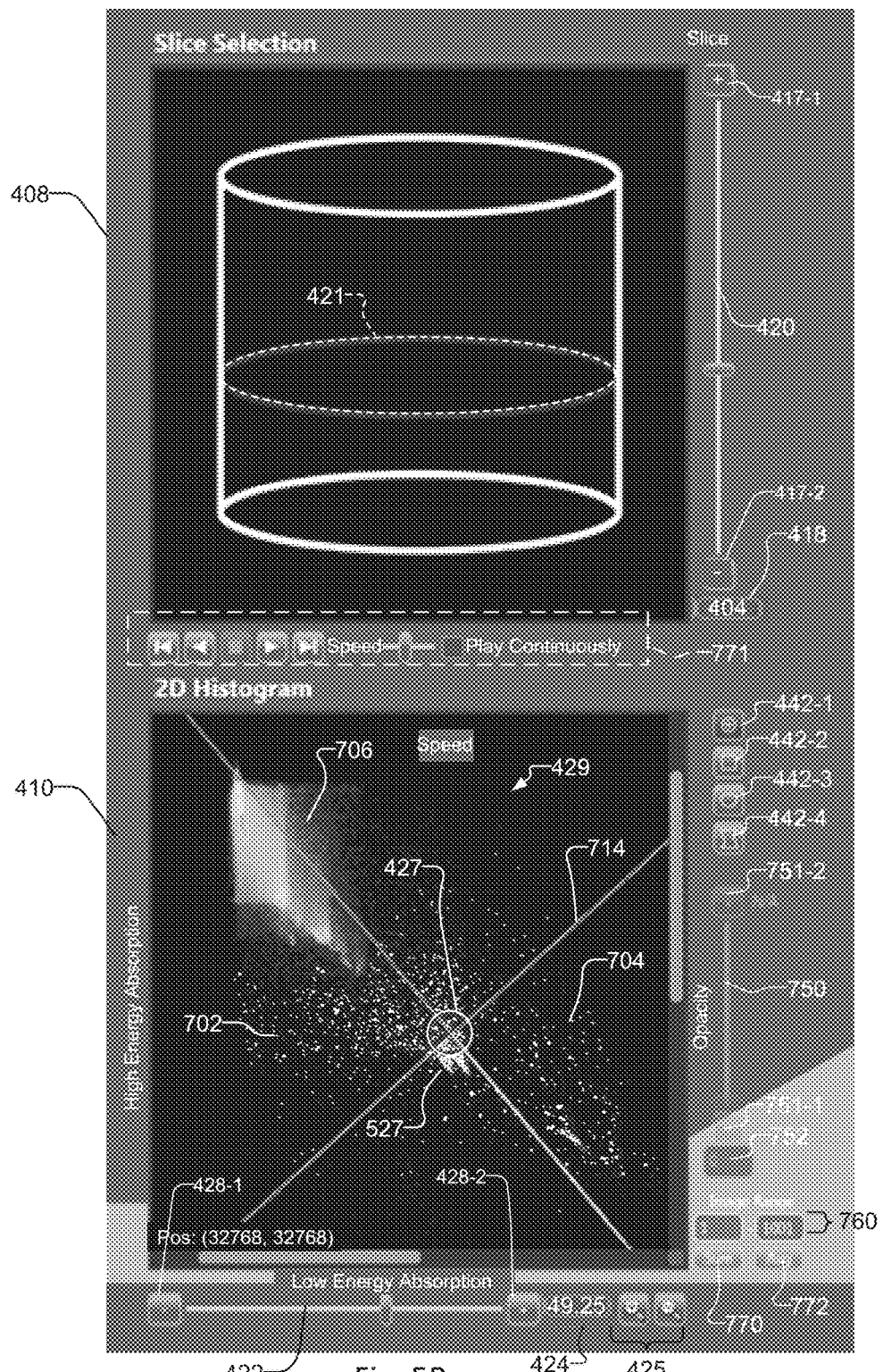
FIG. 5B shows a cropped image of the graphical user interface of the tuning tool of FIG. 4 that includes a magnified view of the High Energy and Low Energy windows for displaying more detail associated with the windows.

FIG. 5B is a cropped and magnified view of the slice selection window 408 and the histogram window 410 of the dual energy contrast tuning tool 134 in FIG. 4. The slice selection window 408 also has slice selection buttons 417-1 and 417-2 that increment and decrement, respectively, the slice selection. The number of the selected slice displayed on the slice number indicator 418 updates in response to the selection, the slice selection display 421 of the interactive graphic 423 updates in response to the selection, and the slice selection slider bar 420 updates in response to the selection.

In addition, animation tool 771 includes controls for presenting a sequence of historical images within the windows of the tuning tool 134. The historical images are associated with each slice selected by the operator in the slice selection window 408. The historical images are retrieved from the slice selection history log 159 from database 150. Controls of the animation tool 771 provide the ability to stop, rewind, fast-forward, playback, and adjust playback speed of the images displayed in the windows of the tuning tool 134.

By default, a slice histogram 429 is created and displayed in response to the slice selection in the slice selection window 408. In addition, however, the operator can create different statistical representations of the slice histogram, also known as sum and average histograms. Sum histogram selector 770 and average histogram selector 772 are used to create the sum and average histograms, respectively. An operator selects a range of slices from which to calculate the Sum and Average histograms via the image range selector 760.

When a sum and/or average histogram is created, an opacity slider 750 is enabled. The opacity slider 750 and its opacity increment 751-2 and decrement 751-1 tools overlay the Sum and/or average histograms upon the default single histogram, with an opacity percentage indicated by the opacity value 752. Creating an overlay of the sum and/or average histograms with varying levels of transparency/opacity upon the single histogram 429 can reveal different information associated with spatial distribution of elements within the sample 114. Image range selector 760 provides the ability to select a range of slices for creating the sum and/or average histograms 429.

Angle selector buttons 428-2 and 428-1 increment and decrement, respectively, the selected angle in the histogram 429 in response to selection of the crosshair ROI selector 442-1. The angle displayed on the angle number indicator 424 updates in response to the selection, and the angle selection slider bar 422 updates in response to the selection. The histogram window 410 also has zoom in/out buttons 425 for magnifying portions of the histogram 429 displayed in the histogram window 410. This allows the operator to more easily visualize individual points within the histogram 429 in the histogram 429 for selecting regions of interest 527 within the histogram 429.

Figure 5C:
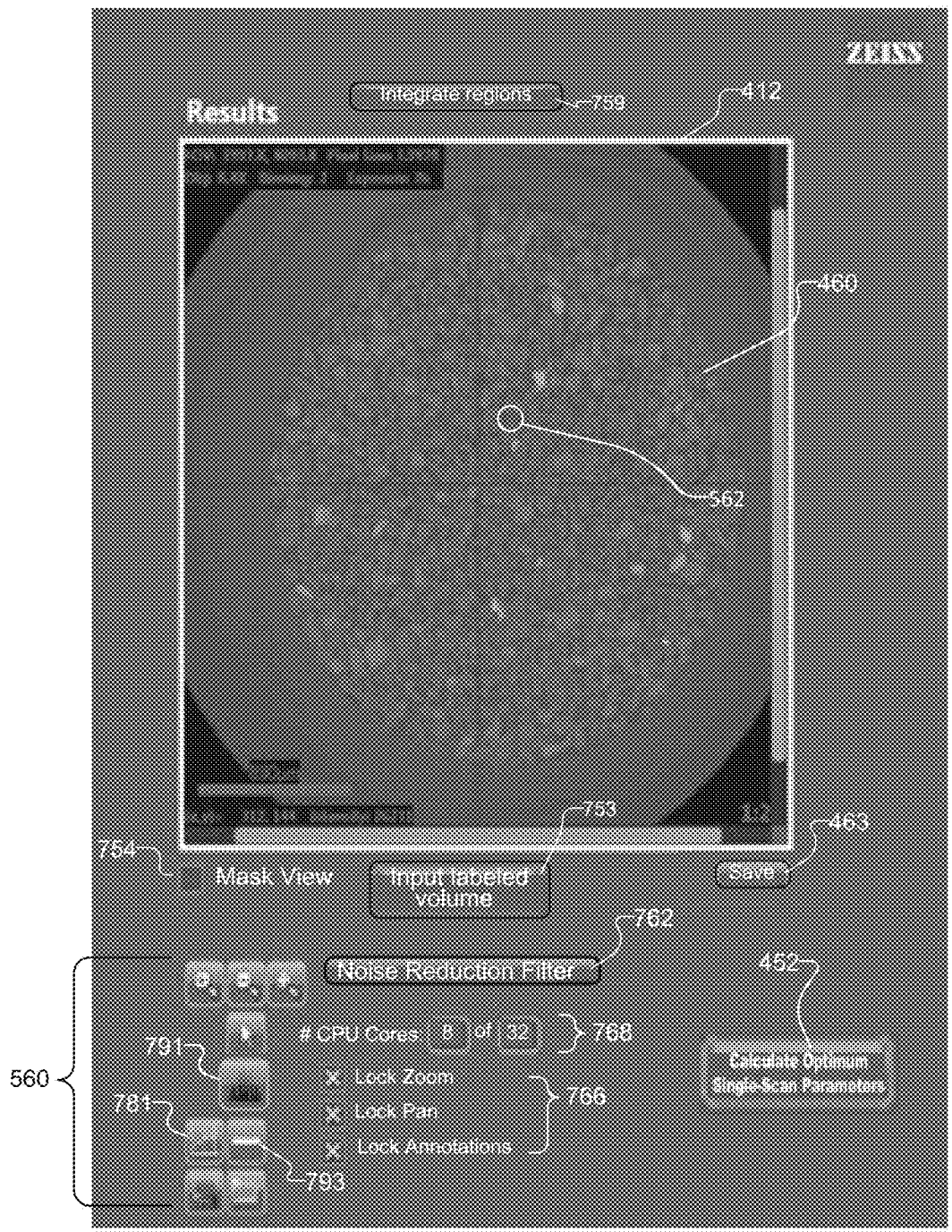
FIG. 5C shows a cropped image of the graphical user interface of the tuning tool of FIG. 4 that includes a magnified view of a Results window of FIG. 4 for displaying more detail associated with the window.

FIG. 5C is a cropped and magnified version of the Results window 412 of the tuning tool 134. After the operator creates the synthetic slice 460, the results window 412 displays the synthetic slice 412 associated with the optimization actions the operator performs within the histogram 429 in the histogram window 410. In addition, the results window 412 enables the user to select an optimized point 562 on the synthetic slice 460. Using the information associated with the optimized point 562, the computer system 124 creates optimum single-scanning parameters that the operator can apply to the same sample, or to a new sample with similar elemental composition.

When the operator selects the optimized point 562 on the synthetic slice 460, the tuning tool 134 enables selection of a "create optimum single scan parameters button" 452. The computer system 124 creates or calculates the optimum single scanning parameters associated with the optimized point 562 in response to the selection. The computer computes the scan settings for the optimum single scan to approximate the contrast in the optimized point 562 as well as possible. This is accomplished by comparing transmission values through the optimized point 562 in the LE and HE data sets and picking the optimized single scan values from a look up table.

FIG. 6A schematically illustrates an exemplary 2-D histogram 429, here a slice histogram, of high-energy x-ray absorption versus low-energy x-ray pixel intensities for a sample 114 having two constituents with different effective atomic number Z in addition to air. The 2-D histogram 429 displays information associated with three visually-distinct clusters of pixel intensities associated with x-ray absorption of three materials; an air pixel intensity cluster 706, a low-Z element pixel intensity cluster 702, and a high-Z element pixel intensity cluster 704.

Via the crosshair ROI selector 424-1, in one example, the operator selects a pivot point 427 and angle within the 2-D histogram 429, and the computer system 124 draws the ratio calculation line 714 through the pivot point 427 and angle selection indicated by the angle number indicator 424. The ratio calculation line 714 provides the ratio of high-energy to low-energy pixel intensity for the computer system 124 to use when creating the synthetic slice 460 for the operator-selected slice in the slice selection window 408. The operator uses the pivot point 427 and angle selection to isolate properties in the sample 114.

In the example, the operator wishes to provide separation between a low-Z element associated with the low-Z pixel intensity cluster 702, and a high-Z element associated with the high-Z element pixel intensity cluster 704. Each point on the pixel intensity clusters is a voxel 712.

The color of the points on the 2-D histogram 429 is a measure of how many voxels are in this bin (i.e. which voxels have the same LE and the same HE x-ray pixel intensity values). The 2-D histogram window 410 uses an offset logarithmic scale when displaying the 2-D histogram 429 to make sure even single pixels show up in the 2-D histogram 429 as recognizable points.

The computer system 124 calculates the synthetic slice 460 from the pivot point 427 and angle selection within the 2-D histogram 429. Specifically, the computer system 124 iterates over all voxels 712 in the 2-D histogram 429, and calculates voxel offset 716, or distance between the voxel 712 and the ratio calculation line 714 in the 2-D histogram 429, for each voxel 712.

The voxel offset 716 is counted positive if the voxel 712 lies on one side of the ratio calculation line 714, and negative if the voxel 712 lies on the opposite side of the ratio calculation line 714. From the set of voxel offsets 716, the computer system 4 creates the synthetic slice 460.

When the computer system 124 saves the synthetic slice 460, the computer system 124 also saves other related information, including the 2-D histogram 429, a binary mask image containing 0 and 1 values, where 0 and 1 represent the separation of voxels from the line (on side or the other), a registered LE image multiplied with the binary mask, a registered HE image multiplied with the binary mask, and the high energy tomographic volume data set 154 and the low-energy tomographic volume data set 152.

These additional datasets are also known as associated tomographic data sets, because they are associated with the creation of and manipulation upon the optimized combined tomographic volume data set 156. An operator uses these additional datasets in subsequent image analysis to, in one example, isolate one material from the optimized combined tomographic volume data set 156.

FIG. 6B schematically illustrates an exemplary 2-D histogram 429 of the same sample as that shown in FIG. 6A. In contrast to FIG. 6A, however, an operator has selected multiple circular regions of interest 527-1 and 527-2. Region of interest 527-1 includes and/or intersects with pixels within the histogram 429 associated with the low-Z element pixel intensity cluster 702, and region of interest 527-2 includes and/or intersects with pixels within the histogram 429 associated with the high-Z element pixel intensity cluster 704. The pixels that intersect and/or are included within the region of interest 527-1 and 527-2, also known as ROI pixels, are used b the computer system 124 to create the synthetic slice 460.

FIG. 7A shows a mask view of the same synthetic slice 460 as that created and displayed in the exemplary DE tuning tool 134 of FIG. 4. The operator selects the mask view of the synthetic slice 460 via the mask view selector 754. The mask view selector 754 selects between mask view and "standard" view of synthetic slice. Typically, the mask view is created by setting the histogram pixel maximum and minimum values to the same single value, so pixels with values above the single value show as white, and pixels below this value show as black in the image displayed in the Results Window 412. In one example, for a pivot point 427 region of interest 527 associated with selection of the crosshair ROI selector 442, the pixel values 'above' the pivot point are above this single value and are therefore rendered as white, and the pixel values below the value for the pivot point 427 are rendered as black. For all non-crosspoint regions of interest 527, all pixels within the ROI(s) (e.g. ROI pixels) are above this single value and are rendered as white in the image displayed in the results window 412, and all pixels located outside the ROI(s) are rendered as black in the image displayed in the results window 412.

FIG. 7B shows the same histogram 429 of LE/HE absorption values as that created and displayed in the exemplary tuning tool 134 of FIG. 7A. Two points labeled 712-1 and 712-2 within the histogram 429 are intersected by the pivot point 427 region of interest 527. In response, the mask view of the synthetic slice 460 in the Results window 412 includes an additional white region, indicated by reference 783, as compared to the image displayed in the Results Window 412 of FIG. 7A.

FIG. 7C shows the same histogram 429 of LE/HE absorption values as that created and displayed in the exemplary tuning tool 134 of FIG. 7A. In contrast, however, no region of interest 527 is selected by the operator within the histogram 429. The position of the histogram points on a horizontal line within the histogram 429 indicates physical differences between separate elements or compounds of the sample, not just differences in density between the same element or compound.

FIG. 7D shows the same histogram 429 of LE/HE absorption values as that created and displayed in the exemplary tuning tool 134 of FIG. 7A. In contrast, however, a circular region of interest 527 has been selected within the histogram 429. In response to selection of the region of interest, the mask view of the synthetic slice 460 in the Results window 412 includes an additional white region, indicated by reference 783, than the image displayed in the Results window 412 of FIG. 7A.

FIG. 7E the same histogram 429 of LE/HE absorption values as that created and displayed in the exemplary tuning tool 134 of FIG. 7A. While a circular region of interest 527 has been selected within the histogram 429, as in FIG. 7D, the region of interest 527 has been selected in a different portion of the histogram 429. In contrast, however, a circular region of interest 527 has been selected within the histogram 429. In response to selection of the region of interest, the mask view of the synthetic slice 460 in the Results Window 412 includes white regions indicated by reference 783-1 and 783-2 in the image displayed in the Results window 412.

FIG. 8 shows a method for data acquisition and preprocessing of images of the sample created by the x-ray imaging system 100/200. The images created by this method are intermediate images of the sample for subsequent image reconstruction and optimization via the method of FIG. 9.

According to step 902, the operator determines the x-ray tomography settings for low-energy ("LE") scan and ("HE") high-energy scan based on estimated composition of the sample. In other examples, these settings are determined automatically by the computer system 124, or the computer system provides suggested settings to the operator. In step 910, the operator selects a filter and/or exposure time for LE scan and specifies the LE voltage setting on x-ray source system. In step 912, the system 100/200 acquires a tomographic data set (projections) at LE settings for a volume of interest of the sample. Then, in step 914, the x-ray imaging system 100/200 generates the LE tomographic volume data set 152 from the LE projections.

In a similar fashion, the x-ray imaging system 100/200 performs a high-energy scan of the same sample. In step 915, the operator selects a filter and/or exposure time for HE scan and specifies an HE voltage setting on the x-ray source system 102. In step 916, the x-ray imaging system 100/200 acquires the tomographic data set (projections) at HE settings for same volume of interest of the sample as that selected for the LE settings. In step 918, the x-ray imaging system generates the HE tomographic volume data set 154 from the HE projections. In step 919, the system 100/200 saves the HE volume data set 152 and the LE volume data sets 154.

For the previous steps, the system 100/200 either performs the HE and LE scans separately, or uses the scout and scan application 132 to perform the scans sequentially.

In step 920, the operator opens the DE tuning tool 134, and in step 922 loads the LE volume data set 152 and the HE volume data set 154. In step 923, the computer system aligns and registers the LE and HD tomographic volume data sets 154/152 with each other and in magnification to achieve pixel-by-pixel registration.

FIG. 9 is a flow diagram showing the operation of the user interface of the tuning tool 134 that operates on the tomographic volume data sets created according to the method of FIG. 8. The method begins at step 925.

In step 930, the tuning tool 134 then detects operator selection of the Noise Reduction Filter selector 762 for filleting the currently loaded LE and HE volume data sets 154, 152. In response to selection, the tuning tool displays the Noise Reduction Filter Window 600, also known as the Noise Reduction Filter screen. Filleting of the HE and LE volume data sets 154/152 is required or useful when there are errant pixels indicative of noise within the HE and LE data sets 154/152 themselves. The operator can additionally and iteratively select regions of interest 527 and create synthetic slices 460 from the one or more regions of interest 527, and examine the synthetic slices 460 for indicia of noise.

FIG. 10 shows the Noise Reduction Filter screen 600. The Noise Reduction Filter screen 600 includes a low energy filename selector 1102 for selecting a LE volume data set 152, and the name of the selected LE volume dataset is displayed in the Low energy filename display 1104. The operator can specify a standard deviation/noise value 1106 and number of iterations 1108 of filtering to apply to the selected LE volume data set 152.

In a similar fashion, the Noise Reduction Filter screen 600 includes a high energy filename selector 1120 for selecting a HE volume data set 154, and the name of the selected HE volume dataset is displayed in the High energy filename display 1122. The operator can specify a standard deviation/noise value 1124 and number of iterations 1126 of filtering to apply to the selected HE volume data set 152.

The Noise Reduction Filter screen 600 also includes a CPU core selector 1128 for selecting a range of CPU cores for processing the filtering operations, a status window 1130, and action buttons 1128 (e.g. Run Filter, Abort, and Exit). In response to selecting the Run Filter action button 1128, the noise reduction filter 161 is applied to the LE and HE volume data sets 152/154 to create filtered versions of the LE and HE volume data sets 152/154. In one example, the noise reduction filter 161 executes a non local means (NLM) filtering operation upon the LE and HE volume data sets 152/154.

Returning to FIG. 9, in step 932, the tuning tool 134 receives operator selections for filtering operations in the Noise Reduction Filter screen 600. In step 934, in response to selection of the "Run filter" button, the tuning tool 134 applies the noise reduction filter 161 to the HE and/or LE tomographic volume data sets 152/154, which filters the high energy slices 431 of the HE tomographic volume data set 154 and/or the low-energy slices 432 of the LE tomographic volume data set 152. The filtering can be applied iteratively (e.g. twice in succession) if desired.

In step 936, the tuning tool 134 determines if the operator has invoked controls within the animation tool 771 for historical display of tuning tool images. If step 936 is true, the method transitions to step 940. Otherwise, the method transitions back to step 925.

In step 940, the tuning tool 134 retrieves the slice selection history log from the database 150 and present images in the tuning tool windows in response to animation tool control selection by the operator.

FIG. 11 provides more detail for step 940 of FIG. 9 for the animation tool 771.

The animation tool 771 enables tuning tool 134 to present historical versions of the images within the windows of the user interface in a sequence. The historical versions of the images are saved to and retrieved from the slice selection history log 159.

According to step 938, the tuning tool 134 retrieves the slice selection history log 159, where the slice selection history log 159 includes information for each selected slice and information for other image parameters associated with each selected slice. In one implementation, the slice selection history log 159 includes records saved for specific pairs of LE and HE images 152, 154 and where the records are indexed by the slice selection number. Each record includes references to the images associated with each slice selection number. In examples, images associated with each selected slice include the LE and HE slice images 431/432, the slice selection display graphic 421, any histograms 429 (e.g. slice, average, sum, that the operator subsequently created from the selected slice, any regions of interest 527 and annotations that the operator selected within the histograms, and the synthetic slice (or its mask view) generated from the histogram(s), if applicable.

In step 944, the tuning tool 134 presents the images of the slice selection history log 159 in a sequence within the respective windows of the tuning tool 134 in accordance with the operator control selection (e.g. FF, REW, PLAY) of the animation tool 771. Other controls within the animation tool 771 include a speed selector for controlling the presentation speed of the images, a stop button, and a "play continuously" selector, in examples.

Then, in step 946, the tuning tool determines if the operator selected the Save button 463 in the Results window 412. If this statement is true, the method transitions to step 948 and otherwise waits for selection of the save button 463. In step 948, the tuning tool saves all images for the current session to the slice selection history log 159.

Returning to FIG. 9, in step 958, the tuning tool 134 determines if the operator has invoked subpixel registration upon the currently loaded LE and HE volume datasets 152, 154 respectively. If this statement is true, the method transitions to step 960. Otherwise, the method transitions to step 925.

According to step 960, the tuning tool 134 creates a filtered aligned High Energy (AHE) volume dataset and a filtered subpixel aligned Low Energy (SALE) volume dataset to improve voxel alignment between LE and HE volume data sets 152/154 during registration.

FIG. 12 provides more detail for step 960 of FIG. 9 for the subpixel registration feature. The method starts at step 1232.

In step 1234, the tuning tool 134 determines if the operator selected the Save button 463 of the Results window 412. If this statement is true, the method transitions to step 1236, where the tuning tool launches the Output Options screen 700. Otherwise, the method transitions to step 1232.

FIG. 13 shows the Output Options screen 700. The Output Options screen 700 operates upon the HE volume data set 154 and LE volume dataset 152 that are currently loaded within the HE window 404 and LE window 404, respectfully. The Output Options screen 700 specifies the filename of one or more images to create for the current HE/LE volume data sets 154/152 and executes associated background task(s) for creating the images.

The Output Options screen 700 includes a browse button 1202 for selecting the location within the database 150 to save an output file and output selectors 1204. The name and type of the output file is determined in response to selecting one or more of the output selectors 1204. The output selectors 1204 include selections for creating an aligned low energy (ALE) data set 1204-1, an aligned high energy (AHE) data set 1204-2, a subpixel aligned low energy (SALE) dataset 1204-3, a contrast combined (CC) mask 1204-4, a combined mask (CM) 1204-5, an aligned low energy with mask (ALEM) data set 1204-6, an aligned high energy with mask (AHEM) data set 1204-7, and a 2D histogram (HS2D) 1204-8. Creation of these aligned versions of the LE and HE volume data sets 152, 154 are necessary because the initial HE and LE volume data sets loaded into the HE and LE windows 406, 404 and registered with one another are cropped by the tuning tool 134 after registration.

The Output Options screen 700 also includes a slice range selector 1206, action buttons 1210 and an auto load selector checkbox 1208. The auto load selector checkbox 1208 is specific to the pixel registration process and is enabled only when the aligned high energy (AHE) dataset and subpixel aligned low energy (SALE) dataset output selectors 1204-2, 1204-3 are selected. The slice range selector 1206 selects a range of slices of the currently loaded HE/LE datasets 154/152 upon which to execute the operator selected alignment options 1204. Action buttons 1210 "save" and "cancel" execute or cancel the operations associated with any selected output selectors 1204. When the auto load selector checkbox 1208 is enabled and selected and the operator selects the save action button 1210, the tuning tool 134 saves the created ARE and SALE volume datasets 154/152 and loads the ARE volume dataset 154 and the SALE volume data set 152 within the HE/LE windows 404/406, respectively.

FIG. 14A shows an example graphical user interface of the tuning tool 134 that includes a histogram 429 created for HE/LE volume datasets 154/152, where the histogram 429 includes errant pixels 40-4. The errant pixels 40-4 are associated with alignment errors during the registration of the HE/LE volume data sets 154/152. In response to operator selection of a rectangular region of interest 527 within the histogram 429, the tuning tool 134 creates a synthetic slice 460, and a mask view of the selected slice 460 is displayed in the Results window 412. Because some of the errant pixels 40-4 in the histogram 429 are also included within the selected region of interest 527, reference 40-3 indicates that corresponding errors appear in the synthetic slice 460.

Returning to FIG. 12, step 1238, the tuning tool 134 detects selection of both the "Aligned High Energy (AHE)" and "SubPixel Aligned Low Energy (SALE)" output selectors 1204-2, 1204-3, detects selection of all slices or a slice range (e.g. via the slice range selector 1206) and detects selection of the "Load AHE and SALE datasets when done" checkbox 1208. In step 1240, the tuning tool 134 determines if the operator selected the Save action button 1210. If this statement is true, the method transitions to step 1242. Otherwise, the method transitions to step 1232.

In step 1242, the tuning tool 134 finds Fractional Offsets (by finding the registration metric at all surrounding single pixel offsets) and doing a quadratic fit and estimating the best fractional offset in the 4 dimensions XYZ and Zoom. In step 1244, the tuning tool 134 optionally adds more dimensions to the registration such as the 3 rotation axes and various distortion terms. In the case of 4 dimensions, the tool 134 rebins the data into the proper fractional amounts for the surrounding 16 (2^4) voxels such that all objects are now aligned with sub pixel accuracy, according to step 1246.

In step 1248, the tuning tool 134 optionally extends the rebinning process to include all additional distortions. As a result, in step 1250, the AHE and SALE volume datasets 154/152 are now subpixel aligned with respect to each other and saved. If the "Load AHE and SALE datasets when done" checkbox 1208 of the Output Options screen was selected, the AHE and SALE volumes 154/152 will already be loaded in the HE and LE windows 404/406.

FIG. 14B shows the result of applying the subpixel registration method of FIG. 12 to the HE/LE volume datasets 154/152 of FIG. 14A. The errant pixels 40-4 in the histogram 429 in FIG. 14B are now removed, and the synthetic slice 460 created from the selected region of interest 527 no longer includes the artifacts created from the errant pixels 40-4, indicated by reference 40-3.

Returning to FIG. 9, in step 962, the tuning tool 134 determines if the operator has invoked the histogram operation via selection of the histogram button 781. If this statement is true, the method transitions to step 990. Otherwise, the method transitions to step 925.

In step 990, the tuning tool 134 creates and displays one or more histograms 429 (e.g. Single, Sum, and/or Average) and optionally superimposes them upon one another to highlight or reveal points of interest within the histogram(s) 429.

FIG. 15 provides more detail for FIG. 9 and step 990 for creation and display of Sum and Average histograms created from the single slice histogram 429.

In step 1034, the tuning tool 134 renders and displays the standard slice histogram 429 of HE versus LE absorption data in the Histogram window 410. Then, the tuning tool 134 determines if the operator has selected the "Sum" 772 button or the "Avg" button in steps 1036 and 1038, respectively. If step 1036 is true, the method transitions to step 1040 to continue creation of a Sum histogram, otherwise the method transitions to step 1050 to end processing. If step 1038 is true, the method transitions to step 1044 to continue creation of an Average histogram, otherwise the method transitions to step 1050 to end processing.

In step 1044, the tuning tool 134 renders and displays an Average histogram in the 2D Histogram window 410, where the value of each point plotted on the Average Histogram 429 is the resulting average of each point in the slice histogram 429 calculated across a specified range of slices.

FIG. 16A shows an exemplary Average Histogram 429. The histogram 429 is created by first creating a default or slice histogram 429. Then, the operator selects the 'Avg' button 772 over a selected image range 760 of slices to create the Average Histogram 429. The average histogram 429 is useful for identifying volumes associated with different elements of the sample 114 that may have not been apparent in the standard histogram 429, in one example.

Returning to FIG. 15, in step 1040, the tuning tool 134 renders and displays a Sum histogram in the 2D Histogram window 410, where the value of each point plotted on the Sum Histogram 429 is the resulting sum of each point in the slice histogram 429 calculated across a specified range of slices.

FIG. 16C shows an exemplary Sum Histogram 429. The histogram 429 is created by first creating a default or slice histogram 429. Then, the operator selects the 'Sum' button 772 over a selected image range 760 of slices to create the Sum Histogram 429. The sum histogram 429 is useful for identifying trace elements of the sample 114 that may have not been apparent in the standard histogram 429.

Returning to FIG. 15, upon completion of both steps 1040 and 1044, the method transitions to step 1046.

In step 1046, the tuning tool 134 detects if the Opacity slider bar 750 or increment/decrement selectors 751-2, 751-1 have been selected by the operator for a specified slice range. If this statement is true, the method transitions to step 1048. Otherwise, the method transitions to step 1050 to end processing.

In step 1048, the tuning tool 134 displays the Average Histogram and/or Sum Histogram as an overlay upon the slice histogram 429 with the operator specified opacity selection and over specified slice selection range to highlight and/or reveal points of interest within the histograms. Note that any image annotations created within the histograms will also fade in and out along with the histogram display 429 in response to the opacity selection. The method then transitions to step 1050 to end processing.

FIGS. 16B and 16D show exemplary overlays of the Average and Sum histograms, respectively, created in response to different opacity selection levels of the opacity slider bar 750.

FIG. 16E shows the same exemplary overlay of the Sum histogram as that displayed in FIG. 16D with instead different regions of interest 527 selected within the histogram (s) 429.

Returning to FIG. 9 and step 992, the tuning tool 134 determines if the operator has invoked the annotation function via selection of the annotation button 793. If this statement is true, the method transitions to step 1000.

In step 1000, the tuning tool 134 enables annotations within the images in the tuning tool windows (e.g. LE, HE Results, and Histogram windows).

FIG. 17 provides more detail for FIG. 9 step 1000 for enabling annotations within the images displayed within the windows of the tuning tool 134. The method starts at step 1702.

In step 1704, the tuning tool 134 enables operator creation of annotations within the images of the current tuning tool window (e.g. within the synthetic slice 460 of the Results window 412). In step 1706, the tuning tool 134 checks if an annotation has been created within the synthetic slice 460 displayed in the Results window 412. If this statement is true, the method transitions to step 1708, otherwise the method waits for an indication of operator annotation creation.

In step 1708, in response to the annotation, the tuning tool 134 displays highlighted versions of corresponding pixels within the images displayed in the other tuning tool windows (e.g. LE, HE, and histogram windows 404,406, 410), where the highlighted pixels are rendered to be visually distinct from pixels in the image that are not associated with the annotation.

FIG. 18 provides an example of the annotation feature indicated in FIG. 9 step 1000 and also shows an example of the pixel mirroring feature. In the example, an operator creates an annotation 790-1 associated with pixels in the mask view of the synthetic slice 460. In response, annotation 790-2 that corresponds with the same pixels in the HE slice image 431 is displayed, and annotation 790-3 that corresponds with the same pixels in the LE slice image 432 is displayed.

Returning to FIG. 9 step 1002, in response to operator selection, annotation, magnification, and/or indication of pixels within an image displayed within one tuning tool window, the selection, annotation, magnification, and/or indication of corresponding pixels in the images is mirrored and displayed in other tuning tool windows.

FIG. 19A provides more detail for step 1002 in FIG. 9 for the pixel mirroring feature.

FIG. 19A starts at step 1720. In step 1722, the tuning tool 134 tests if pixels were selected and optional magnification was selected within images of currently selected tuning tool window (e.g. within a synthetic slice 460 displayed in the Results window 412). If this statement is true, the method transitions to step 1724. Otherwise, the method continues to wait for operator selection and/or magnification of pixels within the synthetic image 460 displayed in the results window 412.

In step 1724, in response to selection and optional magnification of pixels within images of current tuning tool window, the highlighted versions of corresponding pixels within the images displayed in the other tuning tool windows (e.g. LE, HE, and histogram windows) are displayed. The highlighted pixels are rendered to be visually distinct from pixels in the image that are not associated with the selection and optional magnification.

FIG. 20A shows an example of a graphical user interface of the tuning tool illustrating the pixel mirroring feature and supports the method of FIG. 19A.

In FIG. 20A, an operator selects pixels of a region of interest 527 within the histogram 429 displayed within the 2D Histogram window 410 and adjusts the magnification of a mask view of the synthetic slice 460 in the Results window 412. In response to increasing the magnification of the synthetic slice 460 in the Results window, the corresponding slice images 431, 432 of the HE and LE windows 404,406 are displayed with the same magnification. For example, the operator increases the magnification of the mask view of the synthetic slice 460 to enlarge pixels associated with a region 790-1 in the mask view of the synthetic slice 460. In response, the corresponding pixels of region 790-2 and 790-3 in the HE/LE images 431/432 of the HE and LE windows 404/406 are displayed with the same magnification.

FIG. 19B also provides more detail for step 1002 in FIG. 9. In step 1732, the tuning tool 134 tests if pixels were indicated within image of currently selected tuning tool window (e.g. within a HE image 432 displayed in the HE window 406). If this statement is true, the method transitions to step 1734. Otherwise, the method continues to wait for operator indication of pixels within the synthetic image 460 displayed in the results window 412. In examples, indication of pixels includes a "hover" operation upon a pixel via a pointing device such as a computer mouse or touchscreen swipe, where an indication can reveal information associated with a pixel without selecting that pixel.

In step 1734, in response to indication of pixels within image of current tuning tool window (e.g. HE window 4060), the tool displays highlighted versions of corresponding pixels within the images displayed in the other tuning tool windows (e.g. LE, Results, and 2D histogram windows 404, 412, 410), where the highlighted pixels are rendered to be visually distinct from pixels in the images that are not associated with the indication.

FIGS. 20B-1 and 20B-2 show yet another example of the "pixel mirroring" feature associated with the display of images of the sample in the tuning tool 134, where FIGS. 20B-1 and 20B-2 are cropped and magnified versions of the HE window 404 and LE window 406, respectively. In the example, the operator uses a highlighting tool of the tuning tool 134 to highlight specific pixels in the HE image 431 of FIG. 20B-1. The highlighted pixels are grouped in clusters or highlighted regions 499-1 and 499-2.

In response to indication and highlighting of the pixels in the highlighted regions 499-1 and 499-2 of the HE image 431, corresponding pixels within the LE image 432 of FIG. 20B-2 are highlighted to display associated highlighted regions 499-1 and 499-2 in the LE image 432.

Returning to FIG. 9 and step 1004, the tuning tool 13 determines if an operator has invoked an ROI selector 442. If this statement is true, the method transitions to step 1010.

In step 1010, the tuning tool 134 enables operator definition of one or more regions of interest 527 within the histograms 429, generates a synthetic slice 460 from the selected regions of interest 527, and generates a combined tomographic volume data set 156 from the synthetic slice 460.

The tuning tool 134 includes multiple windows (e.g. LE, HE, 2D Histogram, and Results windows 406,404,410, and 412, respectfully) that each display different images of the sample 114. In response to user operations upon the pixels within an image displayed in a tuning tool window, the tuning tool highlights the pixels associated with the user operation by changing the appearance of the pixels to be visually distinct from pixels in the image that were not subject to the user operations. Examples of user operations upon the pixels within the images that cause the tuning tool 134 to highlight those pixels in response include selection of pixels, selection and magnification of pixels, drawing regions of interest 527 that include one or more pixels, indication of the pixels (e.g. touchscreen swipe and/or computer mouse hover operations upon the pixels), and drawing annotations around the pixels. This capability is also referred to as "pixel mirroring."

Then, in response to the tuning tool 134 highlighting pixels of the images displayed in one of the windows or views, the user interface simultaneously highlights the corresponding pixels in the images displayed in the other windows.

FIG. 21 provides more detail for FIG. 9 and step 1010 for enabling definition of one or more regions of interest 527 within the histogram(s) 527. The method starts at step 1802.

In step 1804, the tuning tool 134 determines if the ROI selector 442 selected b operator is the crosshair ROI selector 442-1 (e.g. pivot point 427 and angle 424). If this statement is true, the method transitions to step 1808. Otherwise, the method transitions to step 1816 to process selections associated with the other ROI selectors 442-2 through 442-3.

FIG. 22A-22C show cropped versions of the tuning tool 134 that include magnified views of the Histogram window 429. Different exemplary regions of interest 527 are selected in each of the figures.

FIG. 22A shows a magnified view of a histogram 429 that includes a rectangular region of interest 527-1. The operator selects the region of interest 527-1 by selecting the rectangle ROI selector 442-2. Inset drawing 501-1 provides a further magnified view of region of interest 527-1. In response to the selection, the operator can "drag and drop" a rectangular region of interest 527 within the histogram 429 and adjust the region of interest 527 to include a desired set of ROI pixels.

In a similar vein, FIGS. 22B and 22C include magnified views of circular/elliptical and polygon regions of interest 527-2 and 527-3, respectfully. The circular/elliptical region of interest 527 is enabled by selecting the circular ROI selector 442-3 and the polygon region of interest 527 is enabled by selecting the polygon ROI selector 442-4. Inset drawings 501-2 and 501-3 provide further magnified views of region of interest 527-2 and 527-3, respectfully.

Returning to FIG. 21 and step 1808, in response to operator selection of one or more points 427 and angle selections through the pivot point(s) within histogram (s), identify all pixels in histogram that intersect with pivot points as ROI pixels and create a synthetic slice 460 from the ROI pixels.

In step 1810, the tuning tool 134 displays the created synthetic slice 460 or mask slice in the Results window 412, and for the ROI pixels of the created slice 460, the tuning tool 134 displays the corresponding pixels in the images 431/432 displayed in the LE/HIE windows 404/406 in a visually distinct manner. This is yet another example of the "pixel mirroring" aspect of the tuning tool 134.

In step 1812, the tuning tool detects if there has been a change to the location of the current pivot point selected within the histogram. If this statement is true, the method transitions back to step 1808 to process changes to the existing crosshair ROI 527. Otherwise, the method transitions to step 1814 to determine if more crosshair ROIs have been selected via the crosshair ROI selector 442-1. If this statement is true, the method transitions back to step 1808 to process creation of the new crosshair ROIs 527. Otherwise, the method transitions to step 1824.

Returning to the path of FIG. 21 for processing ROI selectors 442-2 through 442-4, the method processes step 1816. In step 1816, in response to operator selection of non-crosshair ROI selectors 442-2 through 442-4 (e.g. rectangle, circle, and polygon, respectfully) and placement of regions of interest 527 within histogram(s) or within images displayed in HE/LE windows 406/404, all pixels included within all selected regions of interest 527 are identified as ROI pixels and a synthetic slice 460 is created from the ROI pixels.

In step 1818, the tuning tool 134 displays the created synthetic slice 460 or mask slice in the Results window 412, and for the ROI pixels of the created slice 460, the tuning tool 134 displays the corresponding pixels in the images 431/432 displayed in the LE/HE windows 404/406 in a visually distinct manner. This is yet another example of the "pixel mirroring" aspect of the tuning tool 134.

In step 1820, the tuning tool detects if there has been a change to the location of the current region of interest 527 selected within the histogram. If this statement is true, the method transitions back to step 1816 to process changes to the existing region of interest 527. Otherwise, the method transitions to step 1822 to determine if more non-crosshair ROIs have been selected. If this statement is true, the method transitions back to step 1816 to process creation of the new non-crosshair ROIs 527. Otherwise, the method transitions to step 1824.

In step 1824, the tuning tool 134 applies the crosshair/Pivot Point region(s) of interest 527 and/or the non-crosshair ROI(s) 527 to all slices in the currently loaded LE and HE volume data sets 154/152 to create a synthetic slice 460, creates an optimized tomographic volume dataset 156 from the synthetic slice 460, and saves the optimized combined tomographic volume data set 156 and any images, masks, and annotations created in above process for further image viewing and processing.

In step 1826, in response to operator selection of a point on synthetic slice 460, the image contrast associated with the selected point is determined. Then, in step 1828, the tuning tool 134 tests if the operator has selected the "Calculate Optimum Single Scan Parameters" button 492. If this statement is true, the method transitions to step 1830 to compute optimal single scan settings and perform an optimal scan of the sample. Otherwise, the method ends in step 1832.

Returning to FIG. 9 and step 1012, the tuning tool 134 determines if the operator has invoked the gradient suppression function via the histogram control button 791. If this statement is true, the method transitions to step 1040.

FIG. 23 provides more detail for FIG. 9 and step 1040 for the gradient suppression feature. This feature enables operators to remove voxels from the histogram 429 that exceed defined spatial gradient thresholds.

In step 2202, in response to operator selection of the image within the HE or LE windows 406,404 followed by operator selection of the histogram control button 791, the tuning tool 134 displays the histogram control screen 494, where the histogram control screen 494 dictates the operations upon the pixels of the selected images of the HE or LE windows 406,404. Selection of the tuning tool window 406,404 defines a context for operations to be executed upon the selected tuning tool window 406,404. For example, selection of the HE image 431 prior to selection of the histogram control button 791 enables the gradient threshold function provided by the histogram control screen 494 to operate only upon pixels within the histograms 429 associated with the HE image 431. Note that the histogram window 429 can be conveniently moved next to the window including the tuning tool image that the operator defined as the context for subsequent gradient suppression operations.

FIG. 24A includes a slice histogram 429 that includes pixel artifacts. The slice histogram 429 contains all points including those on the edges of objects where the CT numbers are falling off to zero and where there are high CT number gradients. This situation can introduce artifacts during rendering of the slice histogram 429.

In FIG. 24A, the operator selects a region of interest 527 to include ROI pixels associated with element "A" only. These pixels are included within the low energy cluster 704 of the histogram 429. Due to artifacts in the histogram 429 and the potential for pixels of different elements to overlap within the histogram, however, unwanted pixels associated with element "B" are included in the synthetic slice 460 rendered from the selected regions of interest 527.

One type of artifact associated with the pixels in the slice histogram 429 is due to the effect of edges of the elements in the sample. Edge pixels associated with edges of elements in the sample can produce unwanted "tail" artifacts that points towards the 2D histogram values of the surrounding materials because the edge pixels are a mixture of the two in the histogram 429. While most of the pixels are clearly or sharply defined, which represent the main peak(s) of a resolved solid substance, the edge pixels are more blurry. Suppressing the effect of the "tail" artifacts is a preferred way to resolve the pure solid substances of the sample.

More importantly, pixels associated with one element can overlap with pixels of a different element in the histogram 429. This usually occurs when the tail pixels of one substance overlap with the tail pixels of another substance. Typically, the tail pixels of a higher CT substance are overlapped by pixels associated with the main peak of a lower CT substance. Therefore, if one tries to select the lower Z substance by selecting a region of interest 527 that includes pixels of the lower Z substance, unwanted edge pixels or "tail" pixels of the higher Z substance will also be included as ROI pixels in the selected region of interest 527.

To resolve these problems, the operator first selects the LE image 432 image within the LE window 406 to define the context for subsequent histogram manipulations. Then, the operator selects the histogram control button 791 to launch the histogram control screen 794.

FIG. 25 shows a cropped and magnified version of the histogram control screen 794. In another example, the histogram control screen 794 can be displayed as a new mode of the normal histogram 429. The histogram control screen 794 displays an auto-ranged, energy specific histogram 798 that includes only energy absorption values from the slice histogram 429 associated with the current tuning tool window context. Control buttons 796 enable an operator to modify the range and appearance of the energy specific histogram 798. The histogram control screen 794 also includes a gradient option button 711 for enabling the gradient suppression feature, also known as gradient mode of the histogram control screen 794. In FIG. 25, the exemplary energy specific histogram 798 image displayed in the histogram control screen 794 is the slice histogram 429 of the LE image 431 of FIG. 24A with its range of the gradients automatically set to full.

Returning to FIG. 23, in step 2204, the tuning tool 134 detects operator selection of the gradient control button 711 within the histogram control screen 794. According to step 2206, in response to the operator selection of the gradient control button 711, the tuning tool 134 renders an energy specific histogram 798 within the histogram control screen 794. The pixels of the energy specific histogram 798 are produced from the local values of the gradient near each pixel (e.g. gradient values) within the slice histogram 429.

The gradient value is chosen by one of the common techniques using the nearest neighbor pixels of the ROI pixels. In examples, the techniques include sqrt((left−right)^2+(updown)^2) and max(abs(middle−anyneighbor)). For the latter technique, the gradient is the absolute value of the absolute change between all neighboring pixels and each ROI pixel in each selected region of interest 527. By selecting a maximum gradient range or threshold within the energy specific histogram 798, unwanted pixels associated with tail edges of the higher Z substance can be suppressed and the histogram(s) 429 displayed within the 2D Histogram window 410 can be iteratively refined in this manner to include smaller spots without tails. In examples, the operator can select a range of acceptable gradients by dragging a user input device (e.g. computer mouse, finger swipe) over the intended range within the energy specific histogram 798, which resets its scale.

Returning to FIG. 23 step 2208, the tuning tool 134 presents the energy specific histogram 798 within the histogram control screen 794 using the auto-ranging feature of the histogram control screen 794 to enable the energy specific histogram 798 to self-adapt to the scale of the data.

According to step 2210, in response to operator selection of a range of gradient values within the energy specific histogram 798, the tuning tool 134 rescales the energy specific histogram 798 to include only the pixels within the operator selected range of gradient values.

In step 2214, also in response to the operator selection of the range of gradient values within the energy specific histogram 798, the tuning tool 798 recomputes the slice histogram 429 to exclude any points not within the selected gradient range. Separate gradient ranges can exist for the pixels of the LE and HE images 431, 432. If any gradient is out of range, any associated point(s) are excluded from the slice histogram 429.

In step 2216, the tuning tool 134 detects if any additional operator gradient range selections have been indicated by the operator. If this statement is true, the method transitions to step 2210 to enable additional gradient range selections (or enable modification of existing gradient range selections). Otherwise, the method transitions to 2218 to end processing.

FIG. 24B shows the result of applying the gradient suppression method of FIG. 23 to the histogram 429 of FIG. 24A. In response to operator selection of gradient threshold values within the LE energy specific histogram 498 that exclude overlapping HE energy pixels within the slice histogram 429, tail pixels of element "B" that appeared in the slice histogram 429 of FIG. 24A are now suppressed in FIG. 24B and are no longer included within the selected region of interest 527. The unwanted pixels associated with element "B" of the sample also no longer appear in the mask view of the synthetic slice 460 in the Results window 412 of FIG. 24B, where the tuning tool 134 recomputes the synthetic slice 460 from the updated slice histogram 429.

Returning to FIG. 9, in step 1042, the tuning tool 134 determines if the operator has invoked the region integration function via the "integrate regions" button 759 of the Results window 412 for a labeled High Resolution (HiRes) volume dataset 154. If this statement is true, the method transitions to step 1060. Otherwise, the method transitions to step 952.

In step 1060, the tuning tool 134 executes a region integration function upon the histogram(s) 429 to plot points in the histogram(s) 429 for each label included within the labeled HiRes volume data set 154, where the values of the points in the histogram(s) 429 are the average HE/LE values for each labeled region in the labeled HiRes volume data set 154.

FIG. 26 provides more detail for FIG. 9 step 1060 for the region integration feature.

Besides the LE and HE volume data sets 154/152, a third, optimized High Resolution image is acquired, also known as a HiRes volume data set. Typically, the HiRes volume data set 154 is created by placing the sample closer to the x-ray source 102 during the preprocessing method of FIG. 8 in order to increase the geometric magnification. This is co-aligned typically to the LE volume data set 152. The aligned HiRes volume data set 154 is then saved with the normal SAVE action 1210 from the Output options screen 700.

The HiRes volume dataset 154 is then loaded via the HE volume data set selector 430 into the HE window 404. The operator then loads the ALE (or SALE) volume data set into the LE window 406, and creates an aligned HiRes image.

The Aligned HiRes image is then segmented using available image segmentation techniques. Image segmentation techniques include using mean CT values, applying Watershed transforms, and machine learning to segment (e.g. identify) different elements or regions within the sample. Once the various regions are satisfactorily identified and labeled, a label mask including the labels is created which remains aligned to the LE data. The resultant volume data set is also known as a labeled HiRes volume dataset 154.

For each labeled region in the Results window 412, the HE and LE CT values are averaged to one single value for each label, and a single point is entered on the slice histogram 429. Indication of the points (e.g. via a mouse hover or touchscreen swipe operation) displays the label number for each histogram point. In this way, highly accurate 2D positions can be obtained for each substance. In particular, the Z effective can be more accurately determined even if the density varies over the integrated region.

In step 2402, the tuning tool 134 enables the operator to select whether to externally label the high quality LE image (e.g. ALE, SALE) and/or additional High Resolution High Signal to Noise image (HiRes volume data set).

In step 2404, the tuning tool 134 outputs the aligned AHE and ALE (or SALE) volume data sets and in response to operator selection of a HiRes image in the HE window 412, the tuning tool aligns the HiRes volume dataset against the ALE/SALE volume data sets and outputs an aligned High-Res volume data set.

FIG. 27A shows the rendering of the aligned HiRes volume data set from the HiRes volume dataset and a high resolution LE volume dataset 152, such as the Ale or SALE volume data sets 152. The tool loads the HiRes volume dataset into the HE window 404 via the Input Labeled Volume button 153, loads an LE volume data set such as the ALE or SALE volume data sets into the LE window via the low energy tomographic volume data set selector 434, and creates an aligned HiRes volume data set in accordance with step 2404 of FIG. 26.

Returning to FIG. 23 and step 2406, tuning tool segments and labels regions of the sample 114 in the aligned HiRes volume data set using either internal or external tools to create an aligned labeled HiRes volume data set, where the labeled volume contains unique integers for each identified region and remains registered to the ALE and AHE images.

In step 2410, the tuning tool 134 then reads in the triplet of files: AHE, (ALE or SALE), and labeled HiRes volume data set, where the labeled HiRes volume data set is loaded in response to operator selection of the "Input labeled volume" button followed by the name of the labeled HiRes volume data set. To load the labelled HiRes volume data set, the operator selects the Input Labeled Volume selector 753 in FIG. 27A. In response, a file browser/selector (TODO: reference number) appears beneath the Results window 412.

In step 2412, once the three files are read in and the Region integration function, and in response to operator selection of the "Integrate Regions" button of the Results window, the normal display of the slice histogram 429 in the 2D Histogram window 410 is either switched off or set as a layer with variable opacity, in examples. In the latter implementation, the display of the slice histogram 429 functions in a similar fashion as that provided by the overlays of Sum and/or Average histograms upon the slice histogram 429.

In step 2414, the tuning tool 134 calculates a histogram coordinate for each unique label in the labeled HiRes volume data set. This is done by computing the average HE value and average LE value for all voxels with that label in the slice histogram 429 of the 2D histogram window 210.

In step 2416, the tuning tool 134 places and displays a cross mark 52 or other graphical identifier upon locations within the 2D histogram window 410 for each label. In examples, the cross marks can be color coded or have associated numeric labels displayed adjacent to the cross marks.

In step 2418, in response to operator "zoom in" selection of the labeled HiRes volume data set, the tuning tool 134 display the HiRes volume data set to reveal improved 2D placement and resolution than that provided by the normal 2D analysis. The tool then enables the operator to zoom in and examine the 2D placement with more resolution than the normal 2D analysis provided by the prior steps of the method of FIG. 9.

Finally, in step 2420, in response to operator selection of the annotation tools 560, the tuning tool 134 can selectively mask the labeled regions within annotation areas.

FIG. 24B shows the result of applying the region integration method of FIG. 26 to the labeled HiRes volume data set loaded within FIG. 27A. Regions 52-1 and 52-2 in the Results window 412 and the histogram 429 indicate label values 5 and 7, respectively.

While this invention has been particularly shown and described with references to preferred embodiments thereof, it will be understood by those skilled in the art that various changes in form and details may be made therein without departing from the scope of the invention encompassed by the appended claims. For example, while the exemplary microscopy systems are imaging systems, the disclosed tool could also be used with scanning microscopy systems.

What is claimed is:

1. A user interface displayed on a display device of an x-ray imaging microscopy system, the user interface enabling creation of two-dimensional histograms of energy pixel intensity values for a first reconstructed tomographic volume data set and a second reconstructed tomographic volume data set of a sample, the histograms being displayed on the display device, wherein the displayed histograms include:

a slice histogram rendered from a common slice selected among slices of the first reconstructed tomographic volume data set and of the second reconstructed tomographic volume data set;

a sum histogram, where values of points plotted on the sum histogram are the resulting sum of the corresponding points across a user-specified slice selection of the slices; or an average histogram, where values of points on the average histogram are the average of the corresponding points across a user-specified slice selection of the slices; and wherein the sum histogram or the average histogram are overlaid upon the slice histogram to reveal volumes within the sample.

2. A method for displaying information from an x-ray imaging microscopy system by combining a first reconstructed tomographic volume data set with a second reconstructed tomographic volume data set, which were taken under different conditions with the x-ray imaging microscopy system, comprising:

displaying slices of first tomographic volume data set and of a second tomographic volume data set on a display device for the x-ray imaging microscopy system;

selecting a common slice among slices of the reconstructed tomographic volume data sets;

creating a two-dimensional histogram of pixel intensity values for the selected slice in both tomographic volume data sets, the two-dimensional histogram being displayed on the display device;

selecting one or more regions of interest (ROI) within the two-dimensional histogram;

creating a synthetic slice by combining of both corresponding slices of the first and second tomographic volume data sets taking into account the selected regions of interest, the synthetic slice being displayed on the display device; and creating a combined reconstructed volume data set from the synthetic slices;

wherein creating the two-dimensional histogram comprises creating a sum histogram, where values of the points are the resulting sum of the corresponding pixels across the selected slices.

3. The method according to claim 2, wherein creating the two-dimensional histogram comprises creating an average histogram, where values of the points are the resulting sum divided by the number of slices selected of the corresponding pixels across the selected slices.

* * * * *